US008466197B2

(12) United States Patent
Cesar Castro Palomino Laria et al.

(10) Patent No.: US 8,466,197 B2
(45) Date of Patent: *Jun. 18, 2013

(54) THIOCARBONATES AS ANTI-INFLAMMATORY AND ANTIOXIDANT COMPOUNDS USEFUL FOR TREATING METABOLIC DISORDERS

(75) Inventors: Julio Cesar Castro Palomino Laria, Premia de Mar (ES); Luc Marti Clauzel, Barcelona (ES); Antonio Zorzano Olarte, Barcelona (ES); Silvia Garcia Vicente, Sant Feliu de Llobregat (ES); Alec Mian, Barcelona (ES)

(73) Assignee: Genmedica Therapeutics SL, Barcelona (ES)

( * ) Notice: Subject to any disclaimer, the term of this patent is extended or adjusted under 35 U.S.C. 154(b) by 0 days.

This patent is subject to a terminal disclaimer.

(21) Appl. No.: 13/235,031

(22) Filed: Sep. 16, 2011

(65) Prior Publication Data

US 2012/0149769 A1    Jun. 14, 2012

Related U.S. Application Data

(60) Provisional application No. 61/423,026, filed on Dec. 14, 2010, provisional application No. 61/423,010, filed on Dec. 14, 2010.

(51) Int. Cl.
*A61K 31/265* (2006.01)
*C07C 329/06* (2006.01)

(52) U.S. Cl.
USPC ........................................ 514/512; 558/248

(58) Field of Classification Search
USPC ............. 514/562, 538, 512; 562/426; 560/16; 558/248
See application file for complete search history.

(56) References Cited

U.S. PATENT DOCUMENTS

| | | | |
|---|---|---|---|
| 4,181,719 A | 1/1980 | Margetts et al. | |
| 4,563,443 A | 1/1986 | Gobetti | |
| 4,567,163 A | 1/1986 | Ponchiroli | |
| 5,061,710 A | 10/1991 | Haslanger | |
| 5,610,180 A | 3/1997 | Fariss | |
| 5,656,620 A | 8/1997 | Ismail | |
| 5,972,986 A | 10/1999 | Seibert et al. | |
| 6,008,249 A | 12/1999 | Gajdos et al. | |
| 6,013,663 A | 1/2000 | Fujita et al. | |
| 6,121,319 A | 9/2000 | Somers | |
| 6,201,028 B1 | 3/2001 | Shiff et al. | |
| 6,258,848 B1 | 7/2001 | Fantus | |
| 6,309,663 B1 | 10/2001 | Patel et al. | |
| 6,313,164 B1 | 11/2001 | Fujita | |
| 6,355,666 B1 | 3/2002 | Lai et al. | |
| 6,365,176 B1 | 4/2002 | Bell et al. | |
| 6,369,098 B1 | 4/2002 | Pershadsingh et al. | |
| 6,429,223 B1 | 8/2002 | Lai et al. | |
| 6,566,401 B2 | 5/2003 | Herzenberg et al. | |
| 6,646,013 B1 | 11/2003 | Barker et al. | |
| 6,649,591 B2 | 11/2003 | Lai | |
| 6,669,955 B2 | 12/2003 | Chungi et al. | |
| 6,852,760 B1 | 2/2005 | Fine et al. | |
| 6,852,878 B2 | 2/2005 | Meng et al. | |
| 6,896,899 B2 | 5/2005 | Demopolos et al. | |
| 6,909,012 B2 | 6/2005 | Hung | |
| 6,914,075 B2 | 7/2005 | Nakano et al. | |
| 7,078,064 B2 | 7/2006 | Zabrecky | |
| 7,118,762 B2 | 10/2006 | Byrd | |
| 7,122,537 B2 | 10/2006 | Malfroy-Camine et al. | |
| 7,148,211 B2 | 12/2006 | Mazess et al. | |
| 7,241,461 B2 | 7/2007 | Myhill et al. | |
| 7,271,274 B2 | 9/2007 | Meng et al. | |
| 7,345,178 B2 | 3/2008 | Nunes et al. | |
| 7,371,895 B2 | 5/2008 | Meng | |
| 7,375,252 B2 | 5/2008 | Meng | |
| 7,378,412 B2 | 5/2008 | Del Soldato | |
| 7,378,437 B2 | 5/2008 | Soldato | |
| 7,417,034 B2 | 8/2008 | Susilo | |
| 7,666,898 B2 | 2/2010 | Chang | |
| 8,093,292 B2 | 1/2012 | Pacioretty | |
| 2001/0051184 A1 | 12/2001 | Heng | |
| 2002/0037855 A1 | 3/2002 | Stanislaus | |
| 2002/0098247 A1 | 7/2002 | Komorowski et al. | |
| 2002/0155163 A1 | 10/2002 | Benjamin et al. | |

(Continued)

FOREIGN PATENT DOCUMENTS

CN    1439632    9/2003
DE    4327462    2/1995

(Continued)

OTHER PUBLICATIONS

Bailey et al., "The Reduction of Experimentally Induced Inflammation by Sulfhydryl Compounds." Biochemical Pharmacology, 1967, 16:1175-1182.

Kopke et al., "Reduction of noise-induced hearing loss using L-NAC and salicylate in the chinchilla." Hearing Research, 2000, 149: 138-146.

Kowluru et al., "Abnormalities of retinal metabolism in diabetes and experimental galactosemia: VII. Effect of long-term administration of antioxidants on the development of retinopathy." Diabetes, 2001, 50: 1938-1942.

Xiao et al., "Oral taurine but not N-acetylcysteine ameliorates NEFA-Induced Impairment in insulin sensitivity and beta cell function in obese and overweight, non-diabetic men." Diabetologia, 2008, 51: 139-146.

(Continued)

*Primary Examiner* — Kristin Bianchi
(74) *Attorney, Agent, or Firm* — McDonnell Boehnen Hulbert & Berghoff LLP

(57) ABSTRACT

The invention is directed to thiocarbonate compounds of Formula (I)-(III) and methods of treating atherosclerosis, neuropathy, nephropathy, retinopathy, inflammatory disorders, COPD, cardiovascular diseases, metabolic disorders, type I diabetes mellitus, type II diabetes mellitus, LADA, Wolfram Syndrome 1, Wolcott-Rallison syndrome, metabolic syndrome, dyslipidemia, hyperglycemia, or insulin resistance. The compounds of the invention are also useful for protecting pancreatic beta-cells and for reducing free fatty acids, triglycerides, advanced glycated end products, ROS, lipid peroxidation, tissue and plasma TNFalpha and IL6 levels, or for delaying or preventing cardiovascular complications associated with atherosclerosis.

41 Claims, 13 Drawing Sheets

U.S. PATENT DOCUMENTS

| | | | |
|---|---|---|---|
| 2003/0088111 A1 | 5/2003 | Lai | |
| 2003/0100486 A1 | 5/2003 | Ridker et al. | |
| 2003/0119909 A1 | 6/2003 | Stanislaus | |
| 2003/0191064 A1 | 10/2003 | Kopke | |
| 2003/0220468 A1 | 11/2003 | Lai | |
| 2004/0023290 A1 | 2/2004 | Griffin et al. | |
| 2004/0023890 A1 | 2/2004 | Soldato | |
| 2004/0097593 A1 | 5/2004 | Neogi | |
| 2004/0106591 A1 | 6/2004 | Pacioretty et al. | |
| 2004/0146551 A1 | 7/2004 | Mannino et al. | |
| 2005/0008690 A1 | 1/2005 | Miller | |
| 2005/0019399 A1 | 1/2005 | Fischer | |
| 2005/0020654 A1 | 1/2005 | Pershadsingh et al. | |
| 2005/0143356 A1 | 6/2005 | Breyer | |
| 2005/0271661 A1 | 12/2005 | Manivasakam et al. | |
| 2006/0041009 A1 | 2/2006 | Soto Peredo | |
| 2006/0069161 A1 | 3/2006 | Lee et al. | |
| 2006/0135460 A1 | 6/2006 | Widder et al. | |
| 2006/0135489 A1 | 6/2006 | Matuszczak et al. | |
| 2006/0160867 A1 | 7/2006 | Freedman | |
| 2006/0166901 A1 | 7/2006 | Yu | |
| 2006/0172012 A1 | 8/2006 | Finley et al. | |
| 2006/0241017 A1 | 10/2006 | Chandran | |
| 2006/0270635 A1 | 11/2006 | Wallace et al. | |
| 2006/0276416 A1 | 12/2006 | Sinclair et al. | |
| 2007/0042062 A1 | 2/2007 | Pushpangadan et al. | |
| 2007/0149466 A1 | 6/2007 | Milburn et al. | |
| 2007/0231273 A1 | 10/2007 | Wu | |
| 2007/0248590 A1 | 10/2007 | Milne et al. | |
| 2007/0248705 A1 | 10/2007 | Shimura et al. | |
| 2007/0254055 A1 | 11/2007 | Meydani | |
| 2008/0015251 A1 | 1/2008 | Tirosh et al. | |
| 2008/0033027 A1 | 2/2008 | Bascomb et al. | |
| 2008/0038316 A1 | 2/2008 | Wong et al. | |
| 2008/0044399 A1 | 2/2008 | Levy | |
| 2008/0114065 A1 | 5/2008 | Pacioretty et al. | |
| 2008/0118584 A1 | 5/2008 | Olalde Rangel | |
| 2008/0139525 A1 | 6/2008 | Loscalzo | |
| 2008/0176822 A1 | 7/2008 | Chen | |
| 2008/0213319 A1 | 9/2008 | Kang et al. | |
| 2008/0213785 A1 | 9/2008 | Levy | |
| 2008/0220092 A1 | 9/2008 | Dipierro et al. | |
| 2008/0234380 A1 | 9/2008 | Shapiro | |
| 2009/0018136 A1 | 1/2009 | Oppenheimer et al. | |
| 2009/0036516 A1 | 2/2009 | Scherrer et al. | |
| 2009/0169497 A1 | 7/2009 | Horwitz | |
| 2009/0215852 A1 | 8/2009 | Bascomb | |
| 2009/0234011 A1 | 9/2009 | Goldstein | |
| 2009/0325975 A1 | 12/2009 | Buschmann | |
| 2010/0234452 A1* | 9/2010 | Mian et al. | 514/440 |

FOREIGN PATENT DOCUMENTS

| | | |
|---|---|---|
| EP | 0052910 | 6/1982 |
| EP | 0080229 | 6/1983 |
| EP | 0 103 320 | 3/1984 |
| EP | 0 144 519 | 6/1985 |
| EP | 0144519 | 6/1985 |
| EP | 0255164 | 2/1988 |
| EP | 1184366 | 3/2002 |
| EP | 1 219 304 | 7/2002 |
| EP | 1219304 | 7/2002 |
| EP | 1767219 | 3/2007 |
| ES | 549540 | 9/1986 |
| ES | 554853 | 11/1987 |
| FR | 2 550 530 | 2/1985 |
| FR | 2835433 | 8/2003 |
| JP | 43003293 | 2/1968 |
| JP | 56018952 | 2/1981 |
| RU | 2054936 | 2/1996 |
| WO | WO9747270 | 12/1997 |
| WO | WO 98/43630 | 10/1998 |
| WO | WO0061549 | 10/2000 |
| WO | WO0200167 | 1/2002 |
| WO | WO0204434 | 1/2002 |
| WO | WO 02/30866 | 4/2002 |
| WO | WO 02/30867 | 4/2002 |
| WO | WO0236202 | 5/2002 |
| WO | WO 2004/096256 | 11/2004 |
| WO | 2005/032505 | 4/2005 |
| WO | WO2005032505 | 4/2005 |
| WO | 2005/065667 | 7/2005 |
| WO | WO 2005/112949 | 12/2005 |
| WO | WO 2006/037623 | 4/2006 |
| WO | 2006/066894 | 6/2006 |
| WO | WO2006066894 | 6/2006 |
| WO | WO 2007/011958 | 1/2007 |
| WO | 2007/063095 | 6/2007 |
| WO | WO2007063095 | 6/2007 |
| WO | WO2007117048 | 10/2007 |
| WO | 2007/127913 | 11/2007 |
| WO | WO2007127913 | 11/2007 |
| WO | 2008/012603 | 1/2008 |
| WO | WO2008012603 | 1/2008 |
| WO | 2008/089212 | 7/2008 |
| WO | 2009/089011 | 7/2009 |
| WO | WO2009108297 | 9/2009 |
| WO | WO2009124371 | 10/2009 |
| WO | 2009/138437 | 11/2009 |
| WO | WO2009137827 | 11/2009 |
| WO | WO2009138437 | 11/2009 |

OTHER PUBLICATIONS

Xie et al., "Salicylic Acid Induces Rapid Inhibition of Mitochondrial Electron Transport and Oxidative Phosphorylation in Tobacco Cells." Plant Physiology, 1999, 120: 217-225.

Dannan H. et al.: "S-Acylation of cysteine by 0-acetylsalicylic anhydride: A possible mechanism for aspirin hypersensitivity?" Journal of Pharmaceutical Sciences 1986 US, vol. 75, No. 11, 1986, pp. 1081-1084.

Anonymous, "G-201—Salnacedin (197388)." Prous Science Integrity (Drug Data Report), 1994, URL http://integrity.prous.com/integrity/servlet/xmlxsl/pk_ref_list.xml_related_ref_to?p_id197388&_p_origen=PRO&p_tsearch=#link, retrieved on Jul. 13, 2009.

Nomura et al., "Design, synthesis, and evaluation of substituted phenylpropanoic acid derivatives as human peroxisome proliferator activated receptor activators. Discovery of potent and human peroxisome proliferator activated receptor alpha subtype-selective activators." J. Med. Chem., 2003, 46(17): 3581-99.

Tsunoda et al., "KRP-101: A potent PPAR alpha agonist ameliorates fat-induced insulin resistance with suppression of adiposity in dogs." Diabetes, 2007, 56(Suppl. 1): A137-8.

Oskay et al., "Analgesic and anti-inflammatory effects of some benzanilides." Journal of Pharmaceutical Sciences, 1989, 78(6): 460-1.

Netea et al., "The effect of salicylates on insulin sensitivity." J. Clin. Invest., 2001, 108(11): 1723-4.

Fernandez-Real et al., "Salicylates increase insulin secretion in healthy obese subjects." Journal of Clinical Endocrinology and Metabolism, 2008, 93(7): 2523-30.

Zu et al., "Salicylate blocks lipolytic actions of tumor necrosis factor-alpha in primary rat adipocytes." Molecular Pharmacology, 2008, 73(1): 215-23.

Moller et al., "Novel 5-aminosalicylic acid NSAID conjugates: synthesis; pharmacological and toxicological properties." Eur. J. Med. Chem., 1989, 24(5): 463-9.

Hideaki et al., "Beneficial effects of antioxidants in diabetes: Possible protection of pancreatic beta-cells against glucose toxicity," Diabetes, vol. 48, No. 12, Dec. 1999, pp. 2398-2406.

Winiarska et al, "Hypoglycaemic, antioxidative and nephroprotective effects of taurine in alloxan diabetic rabbits," Biochimie, Masson, Paris, FR (Feb. 1, 2009), vol. 91, No. 2, pp. 261-270.

Arany et al, "Taurine supplement in early life altered islet morphology, decreased insulitis and delayed the onset of diabetes in non-obese diabetic mice," Diabetologia, vol. 47, No. 10, Oct. 2004, pp. 1831-1837.

Gorogawa et al, "Probucol preserves pancreatic beta-cell function through reduction of oxidative stress in type 2 diabetes," Diabetes Research and Clinical Practice, vol. 57, No. 1, Jul. 2002, pp. 1-10.

Yan et al, "The study of insulin resistance and leptin resistance on the model of simplicity obesity rats by curcumin," Zhonghua Yufang Yixue Zazhi, Zhonghua Yixuehu, Beijing, CN, vol. 42, No. 11, (Nov. 1, 2008), pp. 818-822.

Maedler et al, "Pioglitazone and sodium salicylate protect human beta-cells against glucose- and IL-beta-induced apoptosis and impaired function," Diabetes, vol. 53, No. Suppl. 2, (Jun. 2004), p. A376.

Bundesverband Der Pharmazeutischen Industrie: "Rote Liste 2004," Jan. 1, 2004, Editio Cantor Verlag Aulendorf, pp. 05420-05433 Aspirin plus C etc.

Efrati et al, "N-acetylcysteine attenuates NSAID-induced rat renal failure by restoring intrarenal prostaglandin synthesis," Nephrol Dial Transplant (2007) 22:1873-1881.

Hsu et al, "Five Cysteine-Containing Compounds Delay Diabetic Deterioration in Balb/cA Mice," 2004, Journal of Nutrition, vol. 134, pp. 3245-3249.

Riess et al, "Pharmacokinetics and metabolism of the antiinflammatory agent voltaren," Scandinavian Journal of Rheumatology, Supplement (1978), 22(Diclofenac Sodium: Antirheum., Anti-Inflammatory, Analg. Agent), 17-29.

Stierlin et al, Biotransformation of diclofenac sodium (Voltaren) in animals and in man. I. Isolation and identification of principal metabolites, Xenobiotica (1979), 9(10), 601-10.

Tsuchiya et al, "Disposition and enterohepatic circulation of diclofenac in dogs," Arzneimittel-Forschung (1980) 30 (10) 1650-3.

Baillie et al, "Taurine conjugation of ibuprofen in humans and in rat liver in vitro. Relationship to metabolic chiral inversion," J Pharmacol Exp Ther, Jun. 1994, 269:1166-1175.

Araya et al, "The Novel Formulation Design of Self-emulsifying Drug Delivery Systems (SEDDS) Type O/W Microemulsion III: The Permeation Mechanism of a Poorly Water Soluble Drug Entrapped O/W Microemulsion in Rat Isolated Intestinal Membrane by the Ussing Chamber Method," Drug Metab. Pharmacokinet. 21(1) 45:53 (2006).

Hoffer et al, "N-Acetylcysteine enhances the action of anti-inflammatory drugs as suppressors of prostaglandin production in monocytes," Mediators of Inflammation, 11, 321-323 (2002).

International Search Report for PCT/EP2010/053419 filed Mar. 16, 2010.

International Search Report for PCT/EP2010/053418 filed Mar. 16, 2010.

International Search Report for PCT/EP2011/072819 filed Dec. 14, 2011.

CAS Registry No. 87573-01-1, STN Entry Date Nov. 16, 1984.

* cited by examiner

THIOCARBONATES AS ANTI-INFLAMMATORY AND ANTIOXIDANT COMPOUNDS USEFUL FOR TREATING METABOLIC DISORDERS

CROSS-REFERENCE TO RELATED APPLICATIONS

This application claims benefit of U.S. Provisional Application Ser. No. 61/423,023, filed Dec. 14, 2010, and U.S. Provisional Application Ser. No. 61/423,010, filed Dec. 14, 2010, both of which are incorporated by reference herein in their entirety.

BACKGROUND

Oxidative stress and inflammation are implicated in the pathogenesis of metabolic diseases, diabetes, obesity, dyslipidemia and their associated cardiovascular complications. For example, oxidative stress is a common pathogenic factor leading to insulin resistance, beta-cell dysfunction, impaired glucose tolerance, and type 2 diabetes mellitus. With regard to inflammation, clinical studies suggest that acute hyperglycemia results in elevated levels of circulating inflammatory cytokines such as TNFalpha, IL6, and IL18.

During hyperglycemia and/or hyperlipidemia, mitochondria generate cellular energy through TCA cycle activity and the associated electron transport chain of the inner mitochondrial membrane. However, while mitochondria generate elevated ATP production, mitochondria can also generate significant reactive oxygen species (ROS) and reactive nitrogen species (RNS). Cells are equipped with several antioxidant enzymes to neutralize ROS and RNS. For example, superoxide anions are enzymatically converted to hydrogen peroxide by a manganese superoxide dismutase (MnSOD) within mitochondria. Hydrogen peroxide can then be rapidly removed by the mitochondrial enzyme glutathione (GSH) peroxidase. A further antioxidant enzyme, catalase, is the hydrogen peroxide detoxifying enzyme founded exclusively in peroxisomes. Glutathione (GSH) is probably the most important defense with which the cell is equipped, for scavenging ROS generated by mitochondria metabolism and excess free radicals produced secondary to hyperglycemia and hyperlipidemia.

However, while cells have a number of available anti-oxidant mechanisms, damage most likely occurs when the ROS is excessive and/or anti-oxidant pathways are overwhelmed as is frequently the case in diabetes. In human diabetic patients, the levels of antioxidant enzymes responsible for scavenging free radicals are diminished. Glutathione pools become depleted in diabetics following frequent and severe hyperglycemic episodes. It is now widely accepted that overproduction of reactive oxygen species (ROS) contributes to cell and tissue dysfunction and damage caused by glucolipotoxicity in diabetes, insulin resistance, and obesity.

In particular, compared to several other cells of the body, pancreatic beta-cells have relatively low levels of free radical detoxification and redox regulating enzymes such as superoxide dismutase, glutathione peroxidase, catalase and thioredoxin. The consequence of limited scavenging systems is that ROS concentration in beta-cells may increase rapidly, damaging the beta-cells. Thus, under hyperglycemic conditions, the production of ROS, and subsequent oxidative stress, contributes to beta-cell deterioration observed in type 2 diabetes.

ROS is also considered a strong stimulus for the release of cytokines and increased superoxide can promote inflammation through NF-kB activation. Thus the role of oxidative stress and associated activation of NF-kB leading to chronic inflammation and insulin resistance is essential in the processes implicated in the pathogenesis of diabetes and its progression. Administration of glutathione, a powerful antioxidant, completely suppresses cytokine elevation, providing further support that an oxidative stress mechanism mediates the inflammatory effects of hyperglycemia in humans.

Salicylates, or aspirin-like drugs, are some of the most commonly used anti-inflammatory agents. For more than two decades, the anti-inflammatory properties of aspirin have been almost exclusively attributed to blocking prostaglandin synthesis via inhibition of cyclo-oxygenase activity. Recently, aspirin and sodium salicylate have been found to inhibit the activation of the transcription factor NF-kB. High doses of salicylate are thought to inhibit NF-kB and its upstream activator, the IKB kinase beta (IKKbeta).

Also, high doses of salicylic acid lower blood glucose levels. Recent studies report that diabetic animals given salicylates or salsalate showed a decrease in IKKbeta activity, accompanied by improvement in insulin resistance. High doses of Salicylate (120 mg/kg/day) administered by subcutaneous infusion in Zucker fa/fa rats or ob/ob mice for 3-4 weeks exhibited anti-diabetic effects, reduction in fasting blood glucose, and glucose tolerance improvement. Beneficial effects of high doses of salicylic acid have been recently reported in human diabetic patients treated with 4.5 g/day of salsalate. However, at this high dose, side effects, such as tinnitus, are enhanced by 66% and the long-term risk of gastric bleeding and ulceration is also increased.

Thus, there remains a need in the art for compounds for treating metabolic disorders by way of ameliorating the inflammatory and oxidative processes associated with such disorders, particularly diabetes.

SUMMARY OF THE INVENTION

The invention provides compounds of Formula (I)-(III), as defined herein. In another aspect, the invention provides pharmaceutical compositions comprised of a compound of Formula (I)-(III) and at least one pharmaceutically acceptable carrier. The compounds of Formula (I)-(III) and the pharmaceutical compositions comprised of Formula (I)-(III) and at least one pharmaceutically acceptable carrier are useful for treating atherosclerosis, neuropathy, nephropathy, retinopathy, inflammatory disorders, Chronic Obstructive Pulmonary Disease (COPD), cardiovascular diseases, metabolic disorders, type I diabetes mellitus, type II diabetes mellitus, Latent Autoimmune Diabetes of Adulthood (LADA), Wolfram Syndrome 1, Wolcott-Rallison syndrome, metabolic syndrome, dyslipidemia, hyperglycemia, or insulin resistance. The compounds and pharmaceutical compositions of the invention are useful for protecting pancreatic beta-cells, preventing their impairment or failure and subsequent lower insulin secretion. Also, the compounds and pharmaceutical compositions of the invention are also useful for reducing free fatty acids (FFA), triglycerides, advanced glycated end products (AGEs), ROS, lipid peroxidation, tissue and plasma TNFalpha and IL6 levels, or for delaying or preventing cardiovascular complications associated with atherosclerosis.

In another aspect, the invention provides methods for treating atherosclerosis, neuropathy, nephropathy, retinopathy, inflammatory disorders, Chronic Obstructive Pulmonary Disease (COPD), cardiovascular diseases, metabolic disorders, type I diabetes mellitus, type II diabetes mellitus, Latent Autoimmune Diabetes of Adulthood (LADA), Wolfram Syndrome 1, Wolcott-Rallison syndrome, metabolic syndrome, dyslipidemia, hyperglycemia, or insulin resistance in a mammal or human patient comprising administering to the mammal or human patient in need of such treatment a therapeutically effective amount of a compound of Formula (I)-(III) or a pharmaceutical composition comprised of a compound of Formula (I)-(III) and at least one pharmaceutically acceptable carrier. The invention also provides methods for reducing free fatty acids (FFA), triglycerides, advanced glycated end products (AGEs), ROS, lipid peroxidation, tissue and plasma TNFalpha and IL6 levels, or for delaying or preventing cardiovascular complications associated with atherosclerosis in a mammal or human patient comprising administering to the mammal or human patient in need of such treatment a therapeutically effective amount of a compound of Formula (I)-(III) or a pharmaceutical composition comprised of a compound of Formula (I)-(III) and at least one pharmaceutically acceptable carrier. Also, the invention provides methods for protecting pancreatic beta-cells, preventing their impairment or failure and subsequent lower insulin secretion in a mammal or human patient comprising administering to the mammal or human patient in need of such treatment a therapeutically effective amount of a compound of Formula (I)-(III) or a pharmaceutical composition comprised of a compound of Formula (I)-(III) and at least one pharmaceutically acceptable carrier.

In another aspect, the invention provides uses for compounds of Formula (I)-(III), or pharmaceutical compositions comprised of a compound of Formula (I)-(III) and at least one pharmaceutically acceptable carrier, for preparing, or for the manufacture of, a medicament for treating atherosclerosis, neuropathy, nephropathy, retinopathy, inflammatory disorders, Chronic Obstructive Pulmonary Disease (COPD), cardiovascular diseases, metabolic disorders, type I diabetes mellitus, type II diabetes mellitus, Latent Autoimmune Diabetes of Adulthood (LADA), Wolfram Syndrome 1, Wolcott-Rallison syndrome, metabolic syndrome, dyslipidemia, hyperglycemia, or insulin resistance in a mammal or human patient. The invention also provides uses for compounds of Formula (I)-(III), or pharmaceutical compositions comprised of a compound of Formula (I)-(III) and at least one pharmaceutically acceptable carrier, for preparing, or for the manufacture of, a medicament for reducing free fatty acids (FFA), triglycerides, advanced glycated end products (AGEs), ROS, lipid peroxidation, tissue and plasma TNFalpha and IL6 levels, or for delaying or preventing cardiovascular complications associated with atherosclerosis in a mammal or human patient. The invention also provides uses for compounds of Formula (I)-(III), or pharmaceutical compositions comprised of a compound of Formula (I)-(III) and at least one pharmaceutically acceptable carrier, for preparing, or for the manufacture of, a medicament for protecting pancreatic beta-cells, preventing their impairment or failure and subsequent lower insulin secretion in a mammal or human patient.

BRIEF DESCRIPTION OF THE DRAWING

The results set forth herein, and the properties and characteristics of the conjugates provided by the invention, can be advantageously understood with regard to the drawings. In each of the drawings comprising bar graphs, the legends identify the bars in left-to-right order.

DETAILED DESCRIPTION

Figure 1:
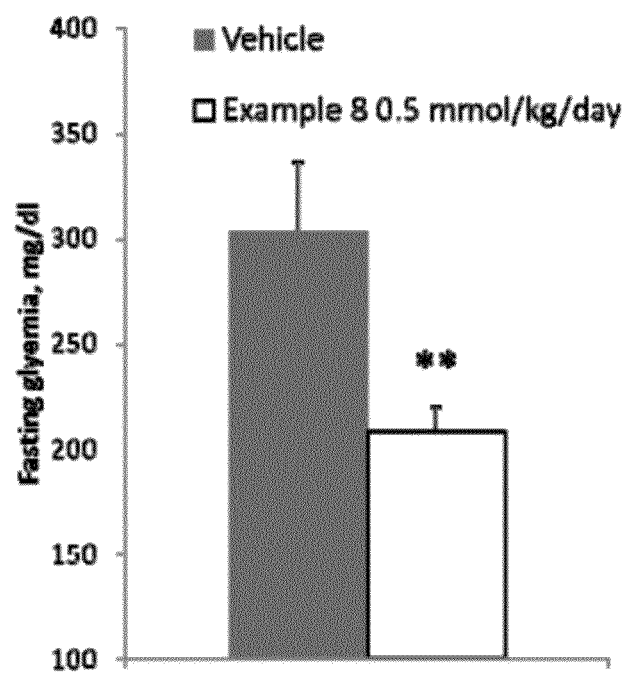
FIG. 1 is a histogram showing the antidiabetic effect of a compound of the invention identified in the figure legend in db/db mice.

In one aspect, the invention provides compounds of Formula (I)

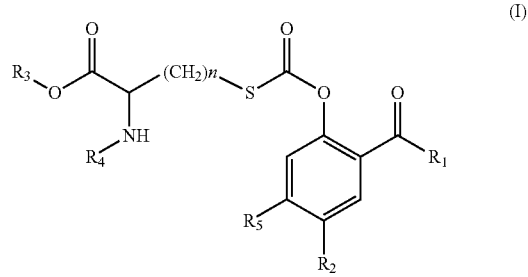

or a pharmaceutically acceptable salt thereof, wherein
n is 1 or 2;
$R_1$ is $OR_6$ or $NR_6R_7$;
$R_2$ is H or 2,4-difluorophenyl;
$R_3$ is H or $(C_1$-$C_6)$alkyl;
$R_4$ is H or acetyl;
$R_5$ is H or trifluoromethyl;
$R_6$ and $R_7$ are independently H, $(C_1$-$C_6)$alkyl, $(C_3$-$C_8)$cycloalkyl, or $(C_3$-$C_8)$cycloalkyl$(C_1$-$C_6)$alkyl, wherein the $(C_1$-$C_6)$alkyl, $(C_3$-$C_8)$cycloalkyl, and $(C_3$-$C_8)$cycloalkyl$(C_1$-$C_6)$alkyl are independently optionally substituted with 1, 2, 3, or 4 substituents that are independently $(C_1$-$C_6)$alkoxy, $(C_1$-$C_6)$alkoxy$(C_1$-$C_6)$alkyl, $(C_1$-$C_6)$alkoxycarbonyl, $(C_1$-$C_6)$alkylthio, halogen, hydroxy, hydroxycarbonyl, $NZ_1Z_2$, or phenyl, wherein the phenyl is optionally substituted with 1, 2, 3, 4, or 5 halogens, and each $Z_1$ and $Z_2$ is independently H or $(C_1$-$C_6)$alkyl; or $R_6$ and $R_7$ together with the nitrogen atom to which they are attached form azetidine, pyrrolidine, piperidine, piperazine, N-methylpiperazine, morpholine, or azepane.

In certain embodiments of the compounds of Formula (I), $R_6$ is $(C_3$-$C_6)$alkyl, $(C_3$-$C_8)$cycloalkyl, $(C_3$-$C_8)$cycloalkyl$(C_1$-$C_6)$alkyl, or aryl$(C_1$-$C_6)$alkyl, wherein the alkyl, cycloalkyl, and aryl groups are independently optionally substituted with 1, 2, 3, or 4 substituents that are independently $(C_1$-$C_6)$alkoxy, $(C_1$-$C_6)$alkoxy$(C_1$-$C_6)$alkyl, $(C_1$-$C_6)$alkoxycarbonyl, $(C_1$-$C_6)$alkylthio, halogen, hydroxy, hydroxycarbonyl, $NZ_1Z_2$, or phenyl, wherein the phenyl is optionally substituted with 1, 2, 3, 4, or 5 halogens; or $R_6$ and $R_7$ together with the nitrogen atom to which they are attached form azetidine, pyrrolidine, piperidine, piperazine, N-methylpiperazine, morpholine, or azepane. For example, in one embodiment of the compounds of Formula (I), $R_6$ is $(C_3$-$C_6)$alkyl or optionally-substituted benzyl.

In other embodiments of the compounds of Formula (I), $R_6$ is H or $(C_1$-$C_6)$alkyl.

In certain embodiments of the compounds of Formula (I) as described above, $R_1$ is $OR_6$. For example, in one embodiment, $R_1$ is methoxy, ethoxy or hydroxy. In another embodiment, $R_1$ is n-propyloxy, i-propyloxy, t-butyoxy, benzyloxy, or 4-methoxybenzyloxy.

In certain embodiments of the compounds of Formula (I) as described above, $R_1$ is $NR_6R_7$ and $R_7$ is H, $(C_1$-$C_6)$alkyl, $(C_3$-$C_8)$cycloalkyl or $(C_3$-$C_8)$cycloalkyl$(C_1$-$C_6)$alkyl, wherein the alkyl and cycloalkyl groups are independently optionally substituted with 1, 2, 3, or 4 substituents that are independently $(C_1$-$C_6)$alkoxy, $(C_1$-$C_6)$alkoxy$(C_1$-$C_6)$alkyl, $(C_1$-$C_6)$alkoxycarbonyl, $(C_1$-$C_6)$alkylthio, halogen, hydroxy, hydroxycarbonyl, $NZ_1Z_2$, or phenyl, wherein the phenyl is optionally substituted with 1, 2, 3, 4, or 5 halogens; or $R_6$ and $R_7$ together with the nitrogen atom to which they are attached form azetidine, pyrrolidine, piperidine, piperazine, N-methylpiperazine, morpholine, or azepane. For example, in one embodiment, $R_7$ is H or $(C_1$-$C_6)$alkyl.

In certain embodiments of the compounds of Formula (I) as described above, $R_6$ and $R_7$ are independently $(C_1$-$C_6)$alkyl.

In certain embodiments of the compounds of Formula (I) as described above, $R_1$ is amino, methylamino, or dimethylamino.

In certain embodiments of the compounds of Formula (I) as described above, $R_2$ is hydrogen. In other embodiments, $R_2$ is 2,4-difluorophenyl.

In certain embodiments of the compounds of Formula (I) as described above, $R_3$ is hydrogen or methyl. For example, in one embodiment, $R_3$ is hydrogen. In another embodiment, $R_3$ is methyl.

In certain embodiments of the compounds of Formula (I) as described above, $R_4$ is acetyl. In other embodiments, $R_4$ is H.

In certain embodiments of the compounds of Formula (I) as described above, $R^5$ is hydrogen.

In certain embodiments of the compounds of Formula (I) as described above, $R_5$ is trifluoromethyl. In certain such embodiments, $R_6$ is H, methyl or ethyl.

In certain embodiments of the compounds of Formula (I) as described above, n is 1.

In certain embodiments of the compounds of Formula (I) as described above, n is 2. In certain such embodiments, $R_6$ is H, methyl or ethyl.

In various embodiments of the compounds of Formula (I), substituents and variables are selected from these particular embodiments described above, in several and various combinations thereof.

Representative compounds of Formula (I) include, but are not limited to, the compounds shown below:

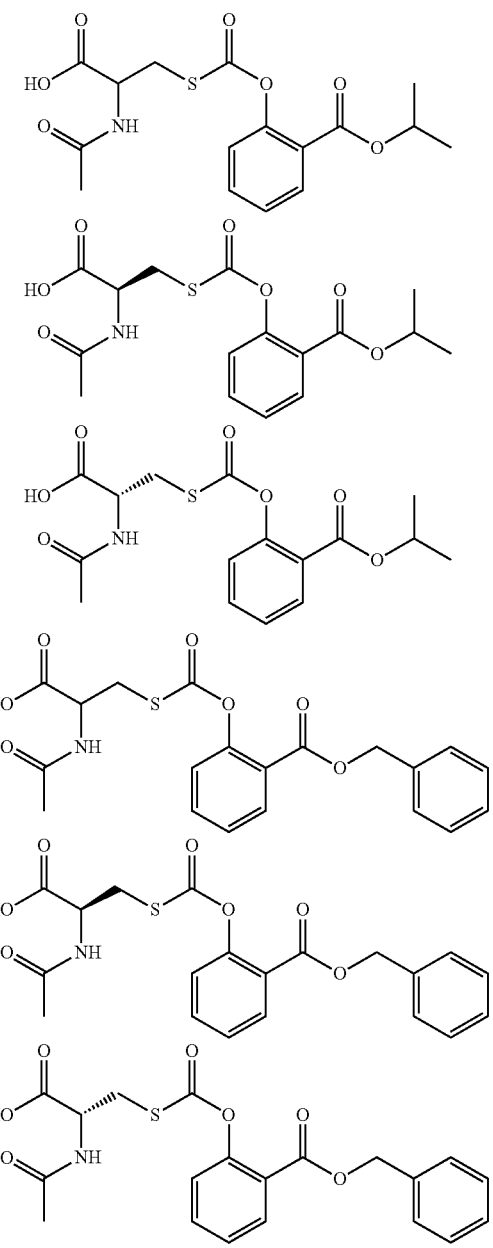

7
-continued
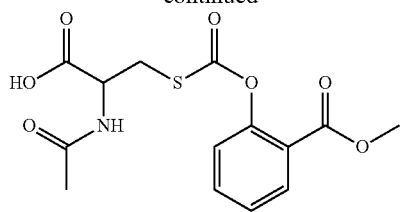
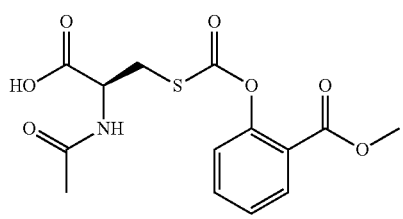
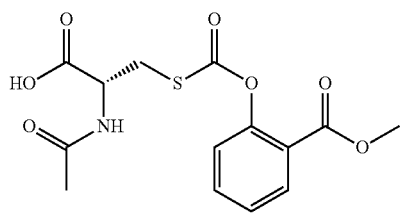
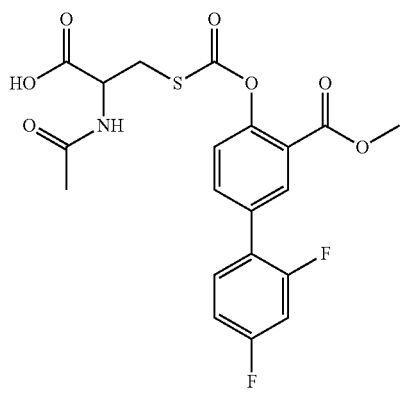
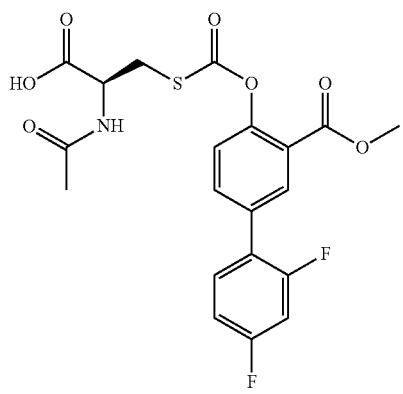
8
-continued
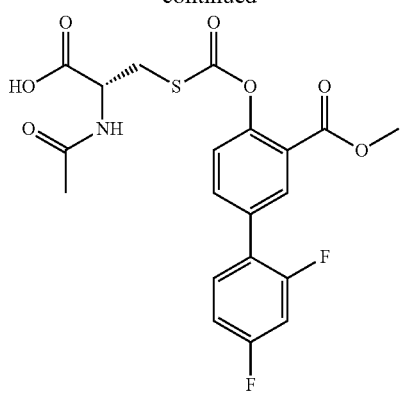
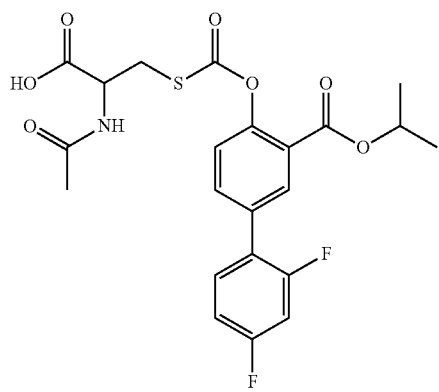
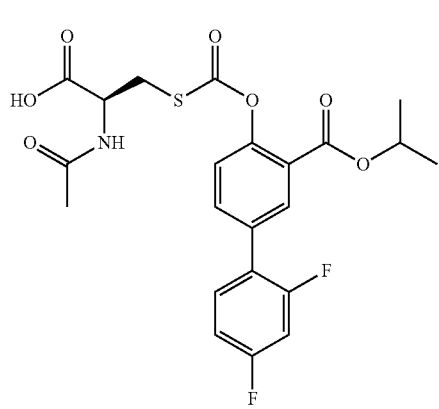
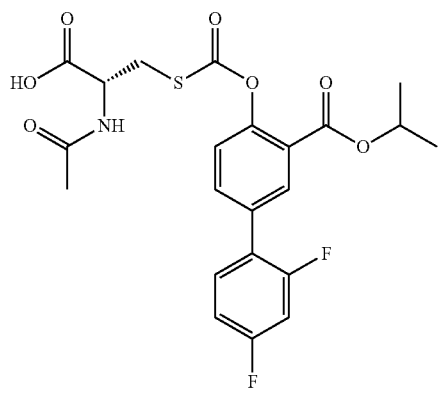

-continued
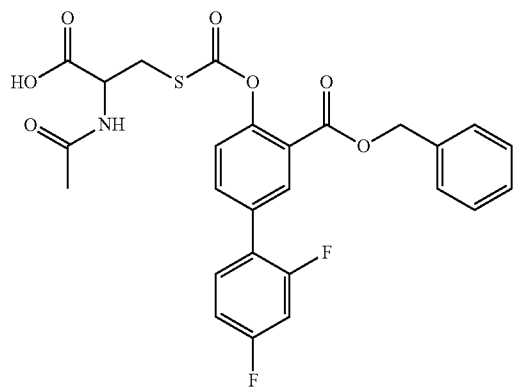
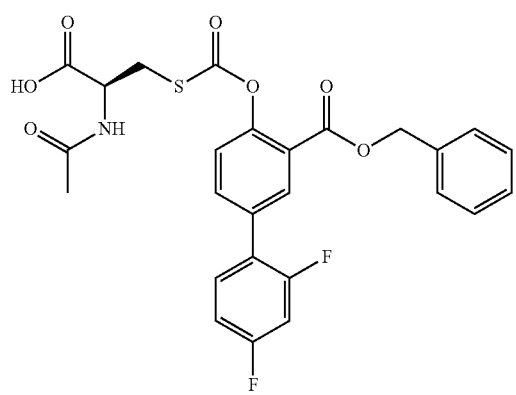
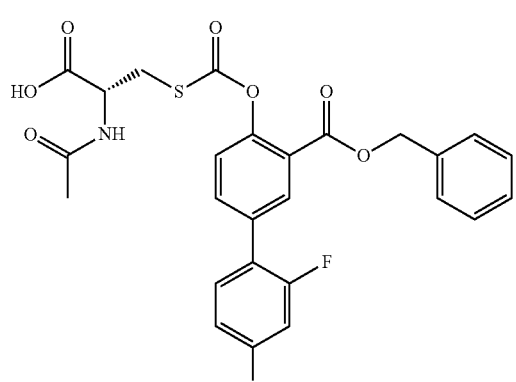
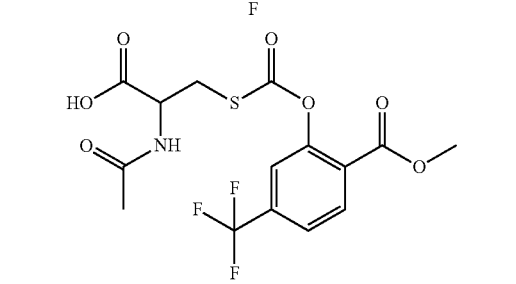
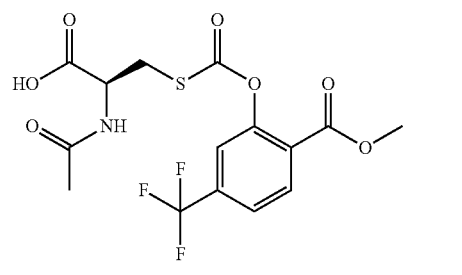
-continued
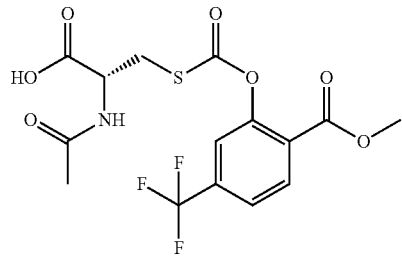
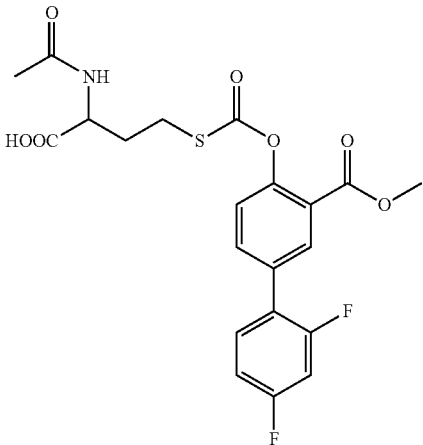
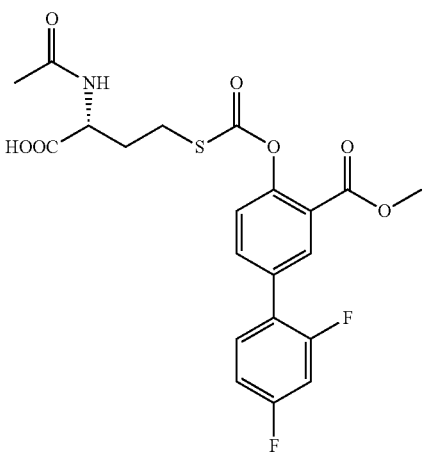
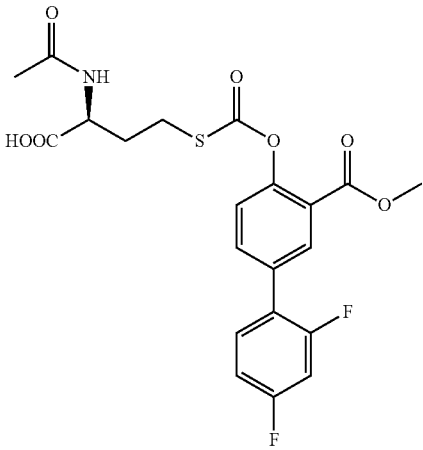

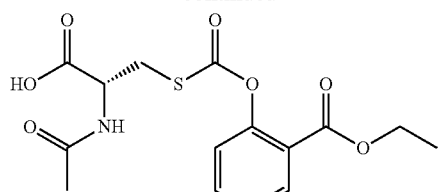
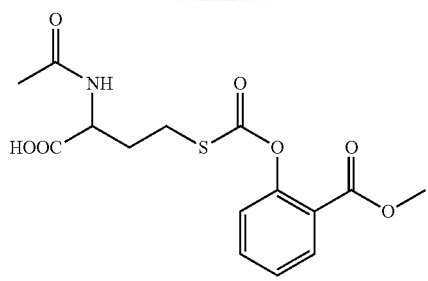
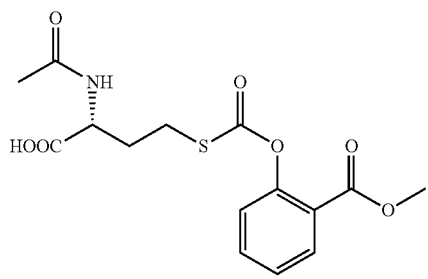
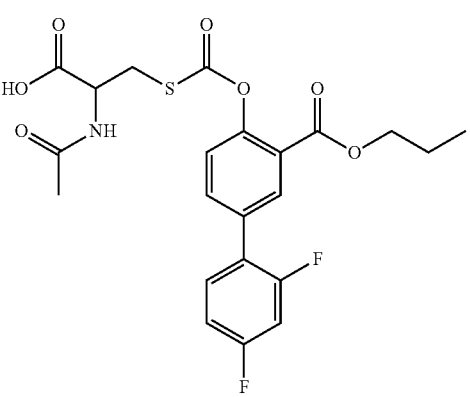
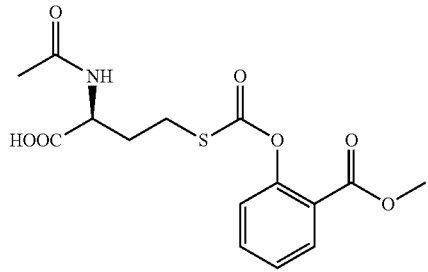
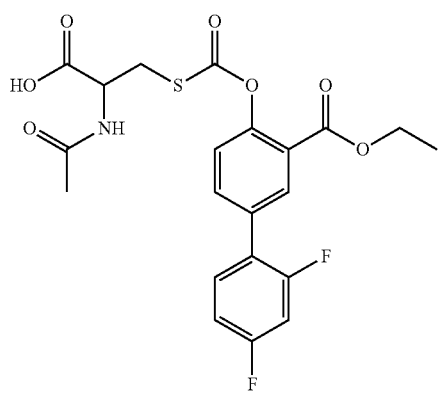
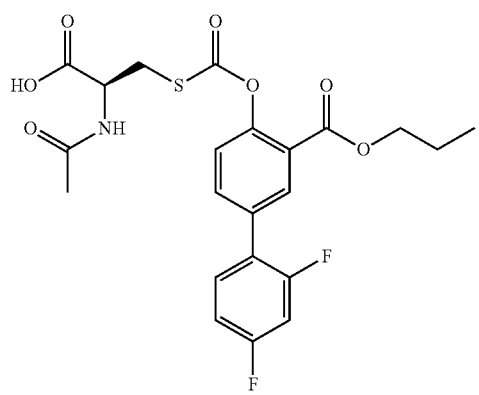
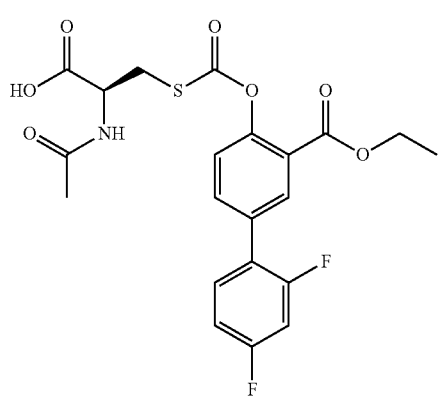
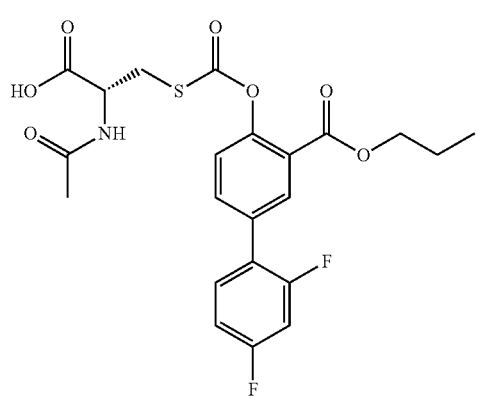

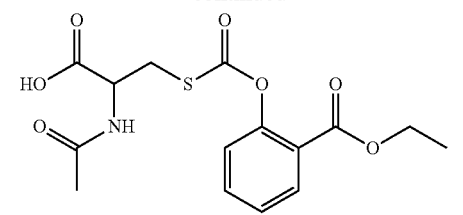
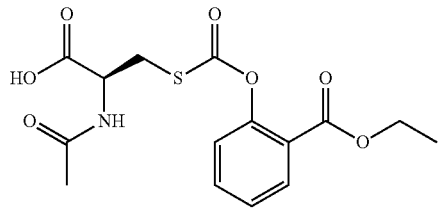
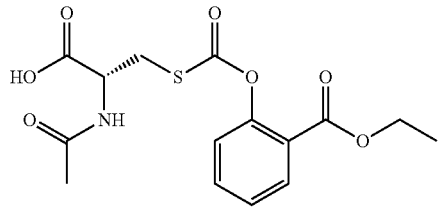
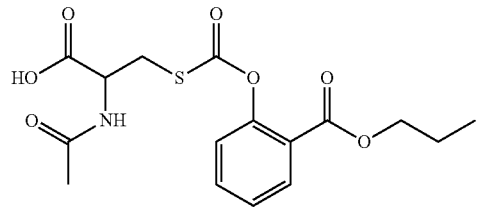
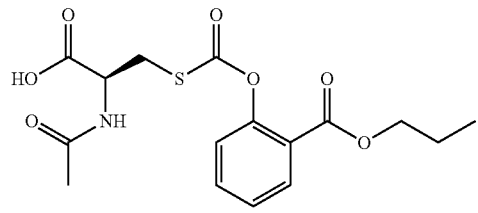
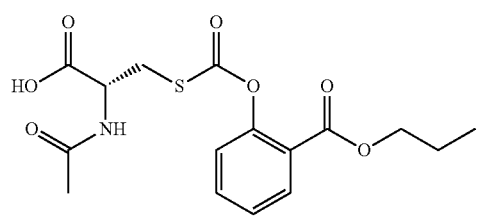
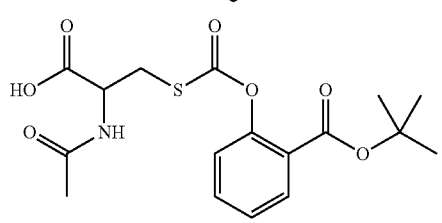
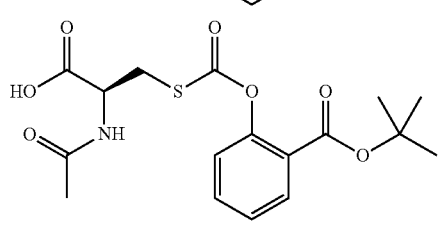
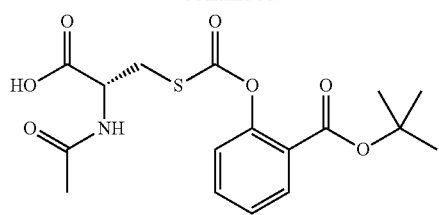
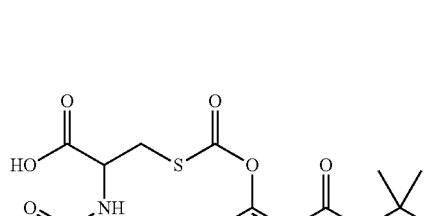
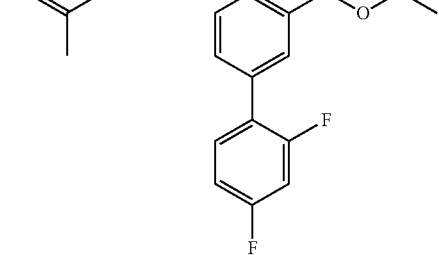
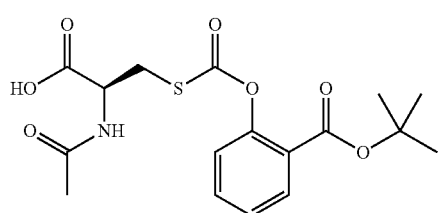
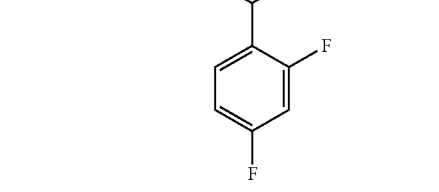
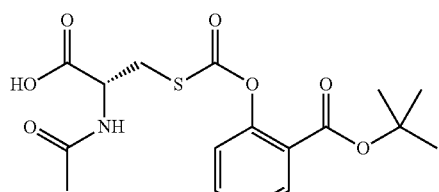
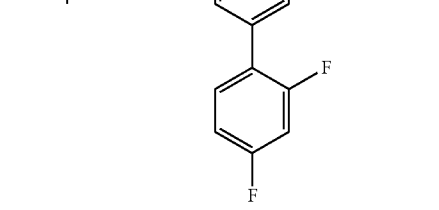

15
-continued
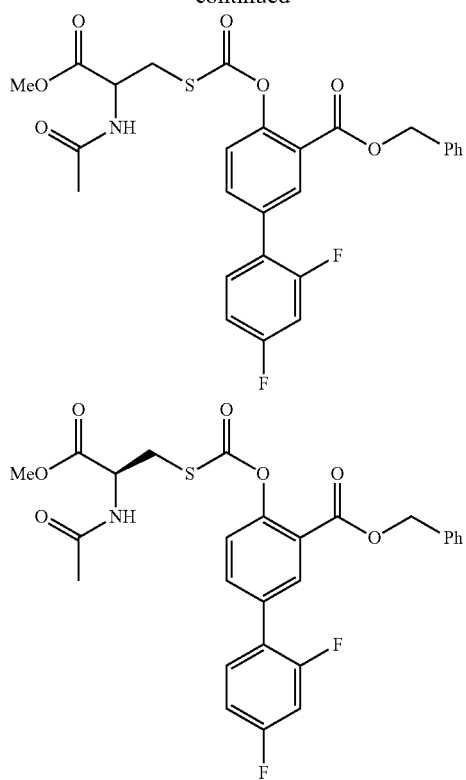
16
-continued
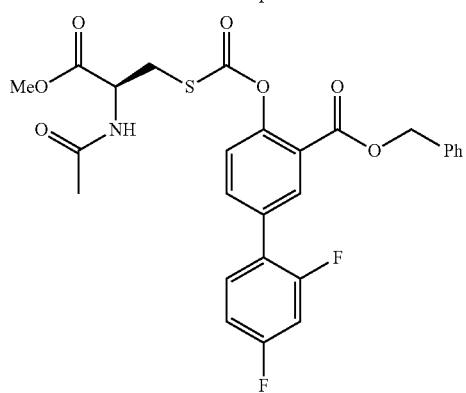

-continued

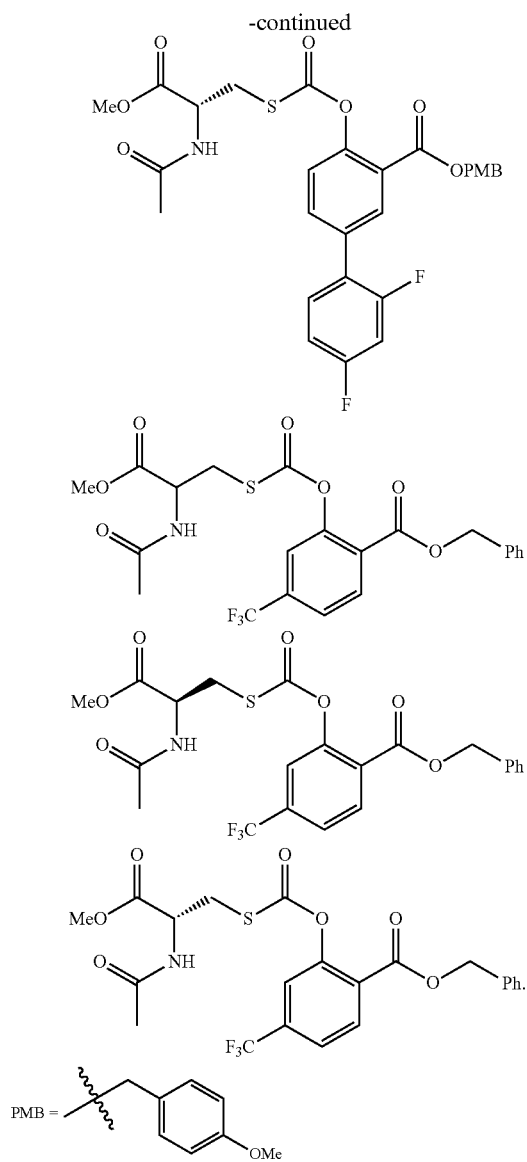

In another aspect, the invention provides pharmaceutical compositions comprised of a compound of Formula (I), as described above, and at least one pharmaceutically acceptable excipient, adjuvant, or carrier.

In another aspect, the invention provides methods for treating atherosclerosis, neuropathy, nephropathy, retinopathy, inflammatory disorders, Chronic Obstructive Pulmonary Disease, cardiovascular diseases, metabolic disorders, type I diabetes mellitus, type II diabetes mellitus, Latent Autoimmune Diabetes of Adulthood, metabolic syndrome, dyslipidemia, hyperglycemia, or insulin resistance in a mammal or human patient comprising administering to the mammal or human patient in need of such treatment a therapeutically effective amount of a compound of Formula (I), as described above, or a pharmaceutical composition including a compound of Formula (I) and at least one pharmaceutically acceptable excipient, adjuvant, or carrier.

In another aspect, the invention provides methods for treating type II diabetes mellitus, metabolic syndrome, dyslipidemia, or insulin resistance in a mammal or human patient comprising administering to the mammal or human patient in need of such treatment a therapeutically effective amount of a compound of Formula (I), as described above, or a pharmaceutical composition including a compound of Formula (I) and at least one pharmaceutically acceptable excipient, adjuvant, or carrier.

In another aspect, the invention provides methods for reducing free fatty acids, triglycerides, advanced glycated end products, ROS, lipid peroxidation, tissue and plasma TNFalpha and IL6 levels, or for delaying or preventing cardiovascular complications associated with atherosclerosis in a mammal or human patient comprising administering to the mammal or human patient in need of such treatment a therapeutically effective amount of a compound of Formula (I), as described above, or a pharmaceutical composition including a compound of Formula (I) and at least one pharmaceutically acceptable excipient, adjuvant, or carrier.

In another aspect, the invention provides methods for protecting pancreatic beta-cells, preventing their impairment or failure and subsequent lower insulin secretion, in a mammal or human patient comprising administering to the mammal or human patient in need of such treatment a therapeutically effective amount of a compound of Formula (I), as shown above, or a pharmaceutical composition including a compound of Formula (I) and at least one pharmaceutically acceptable excipient, adjuvant, or carrier.

In another aspect, the invention provides uses for compounds of Formula (I), or pharmaceutical compositions including a compound of Formula (I) and at least one pharmaceutically acceptable excipient, adjuvant, or carrier, for preparing, or for the manufacture of, a medicament for treating atherosclerosis, neuropathy, nephropathy, retinopathy, inflammatory disorders, COPD, cardiovascular diseases, metabolic disorders, type I diabetes mellitus, type II diabetes mellitus, LADA, Wolfram Syndrome 1, Wolcott-Rallison syndrome, metabolic syndrome, dyslipidemia, hyperglycemia, or insulin resistance in a mammal or human patient. The invention also provides uses for compounds of Formula (I), or pharmaceutical compositions including a compound of Formula (I) and at least one pharmaceutically acceptable excipient, adjuvant, or carrier, for preparing, or for the manufacture of, a medicament for reducing free fatty acids, triglycerides, advanced glycated end products, ROS, lipid peroxidation, tissue and plasma TNFalpha and IL6 levels, or for delaying or preventing cardiovascular complications associated with atherosclerosis in a mammal or human patient. The invention also provides uses for compounds of Formula (I), or pharmaceutical compositions including a compound of Formula (I) and at least one pharmaceutically acceptable excipient, adjuvant, or carrier, for preparing, or for the manufacture of, a medicament for protecting pancreatic beta-cells, preventing their impairment or failure and subsequent lower insulin secretion, in a mammal or human patient.

In another aspect, the invention provides compounds of Formula (II):

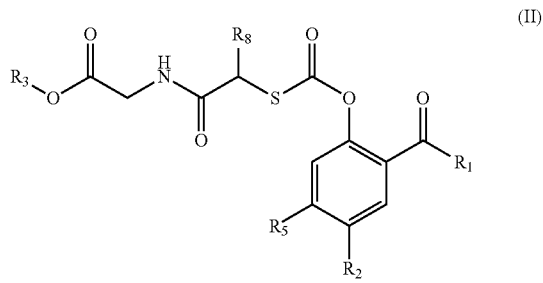

(II)

or a pharmaceutically acceptable salt thereof, wherein
$R_1$ is $OR_6$ or $NR_6R_7$;
$R_2$ is H or 2,4-difluorophenyl;
$R_3$ is H or $(C_1\text{-}C_6)$alkyl;

$R_8$ is H or $(C_1\text{-}C_6)$alkyl $R_5$ is H or trifluoromethyl;

$R_6$ and $R_7$ are independently H, $(C_1\text{-}C_6)$alkyl, $(C_3\text{-}C_8)$cycloalkyl, or $(C_3\text{-}C_8)$cycloalkyl$(C_1\text{-}C_6)$alkyl, wherein the $(C_1\text{-}C_6)$alkyl, $(C_3\text{-}C_8)$cycloalkyl, and $(C_3\text{-}C_8)$cycloalkyl$(C_1\text{-}C_6)$alkyl are independently optionally substituted with 1, 2, 3, or 4 substituents that are independently $(C_1\text{-}C_6)$alkoxy, $(C_1\text{-}C_6)$alkoxy$(C_1\text{-}C_6)$alkyl, $(C_1\text{-}C_6)$alkoxycarbonyl, $(C_1\text{-}C_6)$alkylthio, halogen, hydroxy, hydroxycarbonyl, $NZ_1Z_2$, or phenyl, wherein the phenyl is optionally substituted with 1, 2, 3, 4, or 5 halogens, and each $Z_1$ and $Z_2$ is independently H or $(C_1\text{-}C_6)$alkyl; or $R_6$ and $R_7$ together with the nitrogen atom to which they are attached form azetidine, pyrrolidine, piperidine, piperazine, N-methylpiperazine, morpholine, or azepane.

In certain embodiments of the compounds of Formula (II), $R_6$ is H or $(C_1\text{-}C_6)$alkyl. In other embodiments, $R_6$ is $(C_3\text{-}C_6)$alkyl or optionally-substituted benzyl.

In certain embodiments of the compounds of Formula (II) as described above, $R_1$ is $OR_6$. For example, in one embodiment, $R_1$ is hydroxy, methoxy, ethoxy n-propyloxy, i-propyloxy, t-butyoxy, benzyloxy, or 4-methoxybenzyloxy.

In certain embodiments of the compounds of Formula (II) as described above, $R_1$ is $NR_6R_7$ and $R_7$ is H, $(C_1\text{-}C_6)$alkyl, $(C_3\text{-}C_8)$cycloalkyl or $(C_3\text{-}C_8)$cycloalkyl$(C_1\text{-}C_6)$alkyl, wherein the alkyl and cycloalkyl groups are independently optionally substituted with 1, 2, 3, or 4 substituents that are independently $(C_1\text{-}C_6)$alkoxy, $(C_1\text{-}C_6)$alkoxy$(C_1\text{-}C_6)$alkyl, $(C_1\text{-}C_6)$alkoxycarbonyl, $(C_1\text{-}C_6)$alkylthio, halogen, hydroxy, hydroxycarbonyl, $NZ_1Z_2$, or phenyl, wherein the phenyl is optionally substituted with 1, 2, 3, 4, or 5 halogens; or $R_6$ and $R_7$ together with the nitrogen atom to which they are attached form azetidine, pyrrolidine, piperidine, piperazine, N-methylpiperazine, morpholine, or azepane. For example, in one embodiment, $R_7$ is H or $(C_1\text{-}C_6)$alkyl.

In certain embodiments of the compounds of Formula (II) as described above, $R_6$ and $R_7$ are independently H or $(C_1\text{-}C_6)$alkyl.

In certain embodiments of the compounds of Formula (II) as described above, $R_1$ is amino, methylamino, or dimethylamino.

In certain embodiments of the compounds of Formula (II) as described above, $R_2$ is hydrogen. In other embodiments, $R_2$ is 2,4-difluorophenyl.

In certain embodiments of the compounds of Formula (II) as described above, $R_3$ is hydrogen or methyl. For example, in one embodiment, $R_3$ is hydrogen. In another embodiment, $R_3$ is methyl.

In certain embodiments of the compounds of Formula (II) as described above, $R_8$ is acetyl. In other embodiments, $R_8$ is H.

In certain embodiments of the compounds of Formula (II) as described above, $R_5$ is hydrogen.

In certain embodiments of the compounds of Formula (II) as described above, $R_5$ is trifluoromethyl. In certain such embodiments, $R_6$ is H, methyl or ethyl.

In various embodiments of the compounds of Formula (II), substituents and variables are selected from these particular embodiments described above, in several and various combinations thereof.

Representative compounds of Formula (II) include, but are not limited to, the compounds shown below:

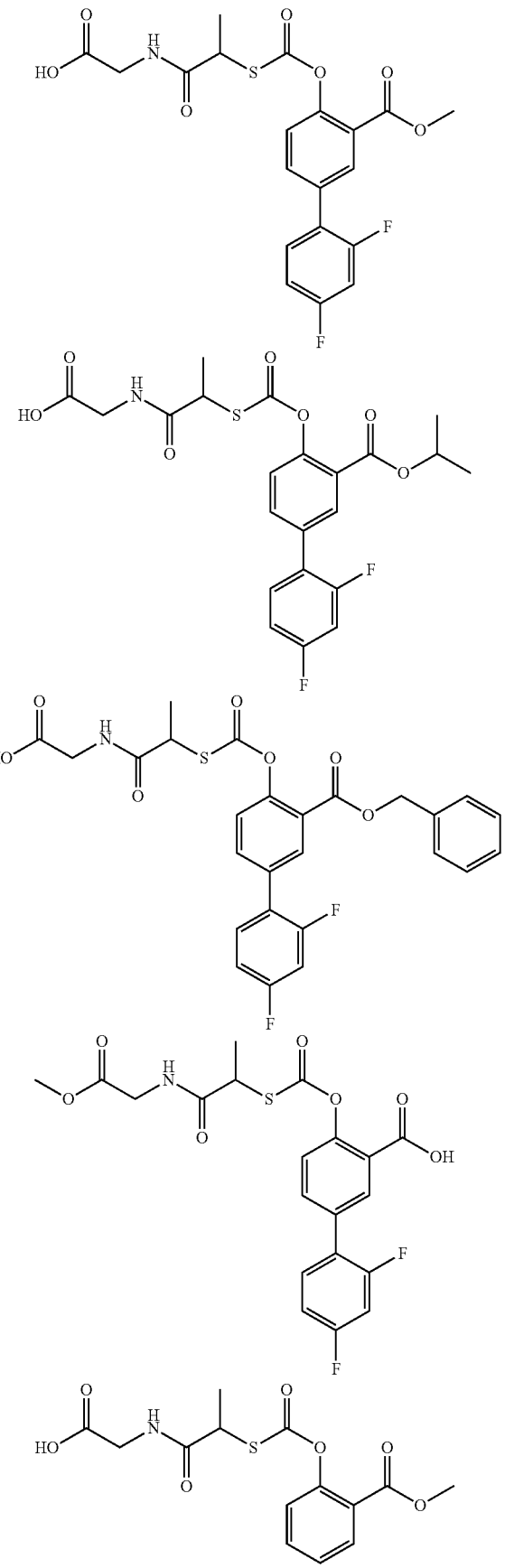

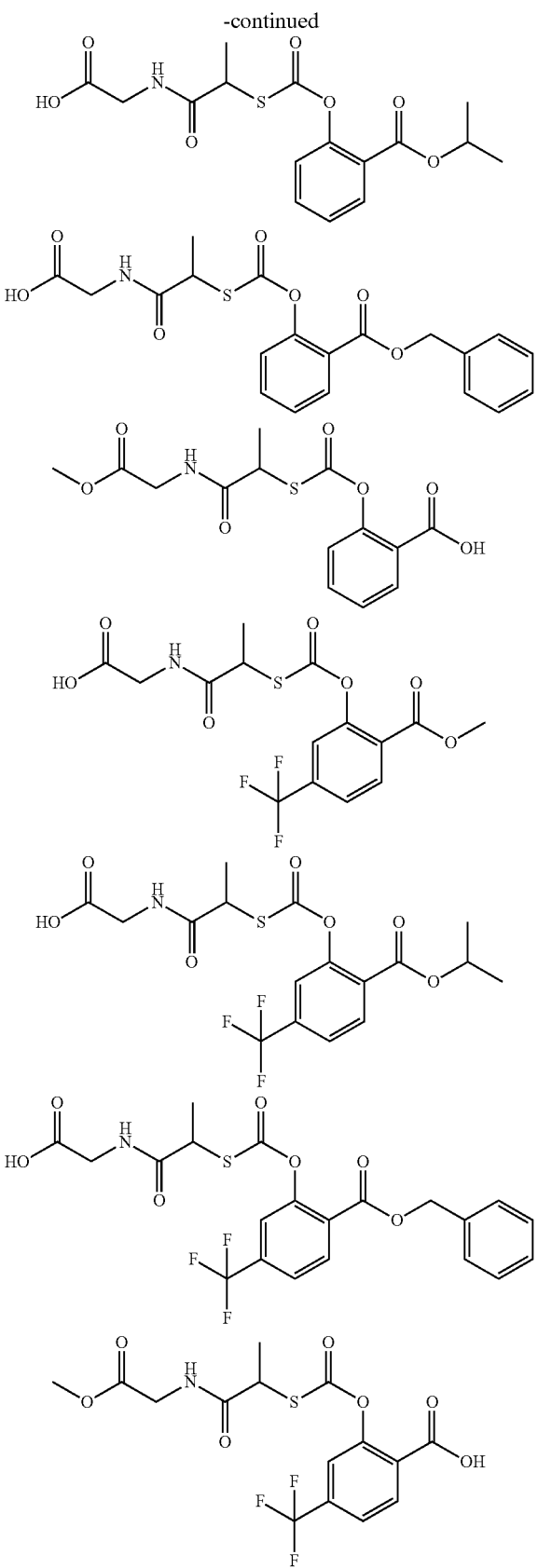

In another aspect, the invention provides pharmaceutical compositions including a compound of Formula (II), as described above, and at least one pharmaceutically acceptable excipient, adjuvant, or carrier.

In another aspect, the invention provides methods for treating atherosclerosis, neuropathy, nephropathy, retinopathy, inflammatory disorders, Chronic Obstructive Pulmonary Disease, cardiovascular diseases, metabolic disorders, type I diabetes mellitus, type II diabetes mellitus, Latent Autoimmune Diabetes of Adulthood, metabolic syndrome, dyslipidemia, hyperglycemia, or insulin resistance in a mammal or human patient comprising administering to the mammal or human patient in need of such treatment a therapeutically effective amount of a compound of Formula (II), as described above, or a pharmaceutical composition including a compound of Formula (II) and at least one pharmaceutically acceptable excipient, adjuvant, or carrier.

In another aspect, the invention provides methods for treating type II diabetes mellitus, metabolic syndrome, dyslipidemia, or insulin resistance in a mammal or human patient comprising administering to the mammal or human patient in need of such treatment a therapeutically effective amount of a compound of Formula (II), as described above, or a pharmaceutical composition including a compound of Formula (II) and at least one pharmaceutically acceptable excipient, adjuvant, or carrier.

In another aspect, the invention provides methods for reducing free fatty acids, triglycerides, advanced glycated end products, ROS, lipid peroxidation, tissue and plasma TNFalpha and IL6 levels, or for delaying or preventing cardiovascular complications associated with atherosclerosis in a mammal or human patient comprising administering to the mammal or human patient in need of such treatment a therapeutically effective amount of a compound of Formula (II), as described above, or a pharmaceutical composition including a compound of Formula (II) and at least one pharmaceutically acceptable excipient, adjuvant, or carrier.

In another aspect, the invention provides methods for protecting pancreatic beta-cells, preventing their impairment or failure and subsequent lower insulin secretion, in a mammal or human patient comprising administering to the mammal or human patient in need of such treatment a therapeutically effective amount of a compound of Formula (II), as described above, or a pharmaceutical composition including a compound of Formula (II) and at least one pharmaceutically acceptable excipient, adjuvant, or carrier.

In another aspect, the invention provides uses for compounds of Formula (II), or pharmaceutical compositions including a compound of Formula (II) and at least one pharmaceutically acceptable excipient, adjuvant, or carrier, for preparing, or for the manufacture of, a medicament for treating atherosclerosis, neuropathy, nephropathy, retinopathy, inflammatory disorders, COPD, cardiovascular diseases, metabolic disorders, type I diabetes mellitus, type II diabetes mellitus, LADA, Wolfram Syndrome 1, Wolcott-Rallison syndrome, metabolic syndrome, dyslipidemia, hyperglycemia, or insulin resistance in a mammal or human patient. The invention also provides uses for compounds of Formula (II), or pharmaceutical compositions including a compound of Formula (II) and at least one pharmaceutically acceptable excipient, adjuvant, or carrier, for preparing, or for the manufacture of, a medicament for reducing free fatty acids, triglycerides, advanced glycated end products, ROS, lipid peroxidation, tissue and plasma TNFalpha and IL6 levels, or for delaying or preventing cardiovascular complications associated with atherosclerosis in a mammal or human patient. The invention also provides uses for compounds of Formula (II), or pharmaceutical compositions including a compound of Formula (II) and at least one pharmaceutically acceptable excipient, adjuvant, or carrier, for preparing, or for the manufacture of, a medicament for protecting pancreatic beta-cells, preventing their impairment or failure and subsequent lower insulin secretion, in a mammal or human patient.

In another aspect, the invention provides compounds of Formula (III)

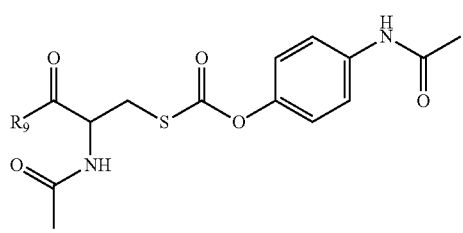

or a pharmaceutically acceptable salt thereof, wherein
$R_9$ is $OR_3$ or $NR_{10}R_{11}$;
$R_3$ is H, $(C_1-C_6)$alkyl, $(C_3-C_8)$cycloalkyl, or $(C_3-C_8)$cycloalkyl$(C_1-C_6)$alkyl, wherein the $(C_1-C_6)$alkyl, and $(C_3-C_8)$cycloalkyl, $(C_3-C_8)$cycloalkyl$(C_1-C_6)$alkyl are independently optionally substituted with 1, 2, 3, or 4 substituents that are independently $(C_1-C_6)$alkoxy, $(C_1-C_6)$alkoxy$(C_1-C_6)$alkyl, $(C_1-C_6)$alkoxycarbonyl, $(C_1-C_6)$alkylthio, halogen, hydroxy, hydroxycarbonyl, $NZ_1Z_2$, or phenyl, wherein the phenyl is optionally substituted with 1, 2, 3, 4, or 5 halogens;
$R_{10}$ and $R_{11}$ are independently H, $(C_1-C_6)$alkyl, $(C_3-C_8)$cycloalkyl, or $(C_3-C_8)$cycloalkyl$(C_1-C_6)$alkyl, wherein the $(C_1-C_6)$alkyl, $(C_3-C_8)$cycloalkyl, and $(C_3-C_8)$cycloalkyl$(C_1-C_6)$alkyl are independently optionally substituted with 1, 2, 3, or 4 substituents that are independently $(C_1-C_6)$alkoxy, $(C_1-C_6)$alkoxy$(C_1-C_6)$alkyl, $(C_1-C_6)$alkoxycarbonyl, $(C_1-C_6)$alkylthio, halogen, hydroxy, hydroxycarbonyl, $NZ_1Z_2$, or phenyl, wherein the phenyl is optionally substituted with 1, 2, 3, 4, or 5 halogens; or $R_4$ and $R_5$ together with the nitrogen atom to which they are attached form azetidine, pyrrolidine, piperidine, piperazine, N-methylpiperazine, morpholine, or azepane;
in which each $Z_1$ and $Z_2$ is independently H or $(C_1-C_6)$alkyl.

In certain embodiments of the compounds of Formula (III), $R_9$ is $OR_3$, and $R_3$ is $(C_3-C_6)$alkyl, $(C_3-C_8)$cycloalkyl, or $(C_3-C_8)$cycloalkyl$(C_1-C_6)$alkyl, wherein the alkyl and cycloalkyl groups are independently optionally substituted with 1, 2, 3, or 4 substituents that are independently $(C_1-C_6)$alkoxy, $(C_1-C_6)$alkoxy$(C_1-C_6)$alkyl, $(C_1-C_6)$alkoxycarbonyl, $(C_1-C_6)$alkylthio, halogen, hydroxy, hydroxycarbonyl, $NZ_1Z_2$, or phenyl, wherein the phenyl is optionally substituted with 1, 2, 3, 4, or 5 halogens. For example, in certain embodiments, $R_9$ is n-propyloxy, i-propyloxy, t-butyoxy, benzyloxy, or 4-methoxybenzyloxy.

In certain embodiments of the compounds of Formula (III), $R_9$ is $NR_{10}R_{11}$; and $R_{10}$ is $(C_2-C_6)$alkyl, $(C_3-C_8)$cycloalkyl, or $(C_3-C_8)$cycloalkyl$(C_1-C_6)$alkyl, wherein the alkyl and cycloalkyl groups are independently optionally substituted with 1, 2, 3, or 4 substituents that are independently $(C_1-C_6)$alkoxy, $(C_1-C_6)$alkoxy$(C_1-C_6)$alkyl, $(C_1-C_6)$alkoxycarbonyl, $(C_1-C_6)$alkylthio, halogen, hydroxy, hydroxycarbonyl, $NZ_1Z_2$, or phenyl, wherein the phenyl is optionally substituted with 1, 2, 3, 4, or 5 halogens; and $R_{11}$ is H, $(C_1-C_6)$alkyl, $(C_3-C_8)$cycloalkyl, or $(C_3-C_8)$cycloalkyl$(C_1-C_6)$alkyl, wherein the alkyl and cycloalkyl groups are independently optionally substituted with 1, 2, 3, or 4 substituents that are independently $(C_1-C_6)$alkoxy, $(C_1-C_6)$alkoxy$(C_1-C_6)$alkyl, $(C_1-C_6)$alkoxycarbonyl, $(C_1-C_6)$alkylthio, halogen, hydroxy, hydroxycarbonyl, $NZ_1Z_2$, or phenyl, wherein the phenyl is optionally substituted with 1, 2, 3, 4, or 5 halogens, or $R_{10}$ and $R_{11}$ together with the nitrogen atom to which they are attached form azetidine, pyrrolidine, piperidine, piperazine, N-methylpiperazine, morpholine, or azepane. For example, in certain such embodiments, $R_9$ is $NR_{10}R_{11}$, $R_{10}$ is $(C_2-C_6)$alkyl and $R_{11}$ is H or $(C_1-C6)$alkyl.

Representative compounds of Formula (III) include, but are not limited to, the compounds shown below:

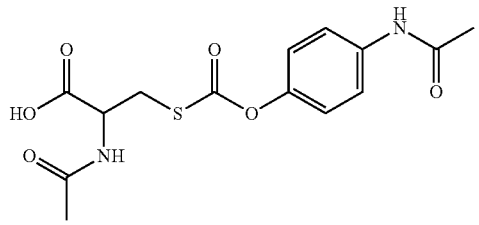

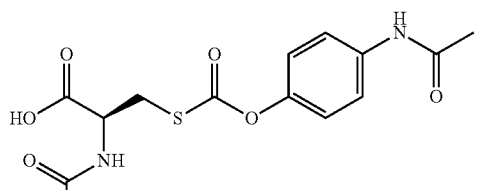

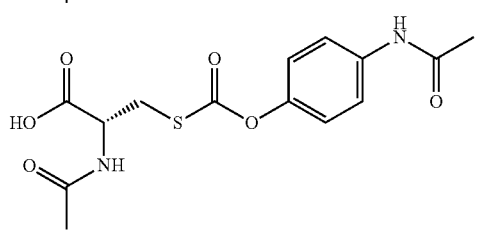

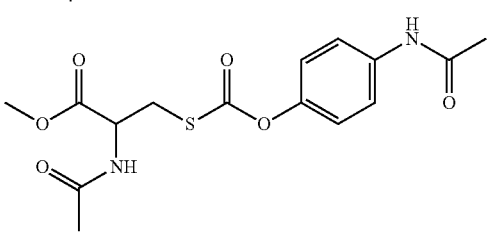

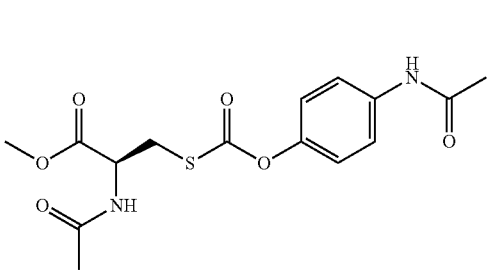

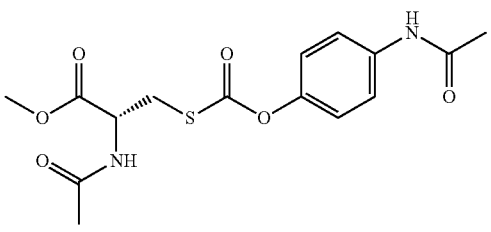

-continued

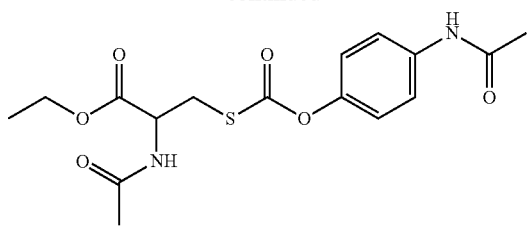

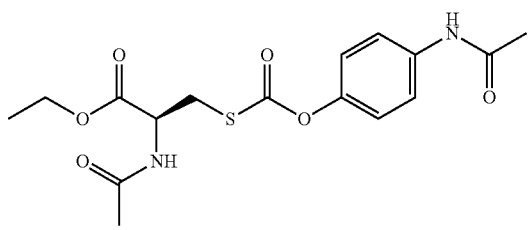

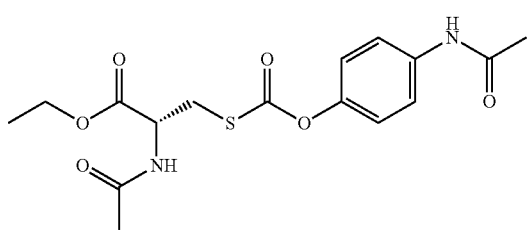

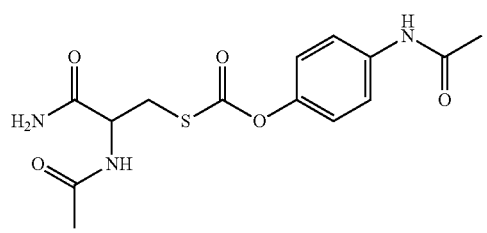

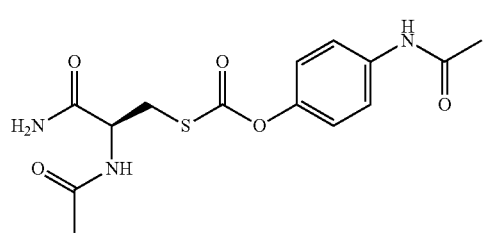

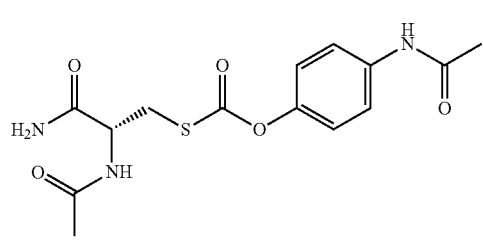

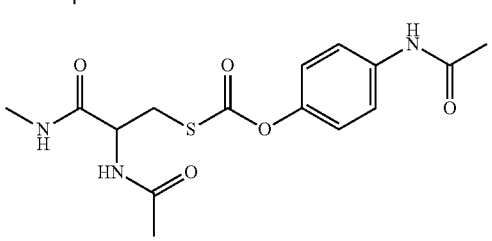

-continued

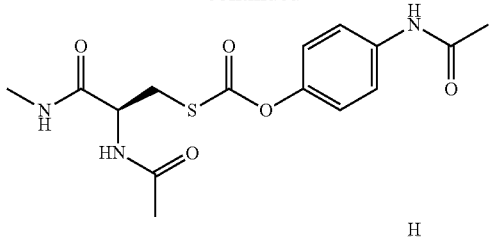

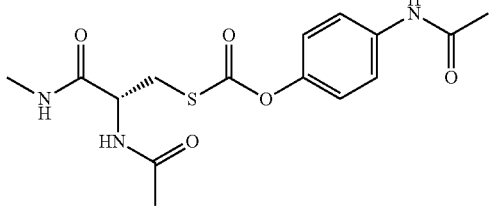

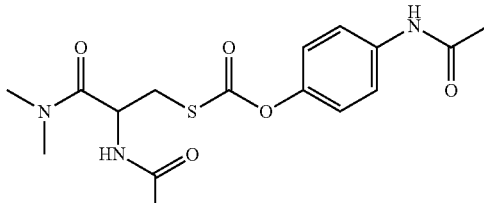

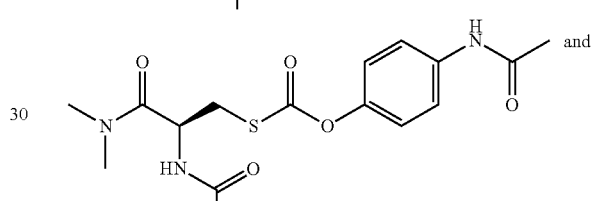

and

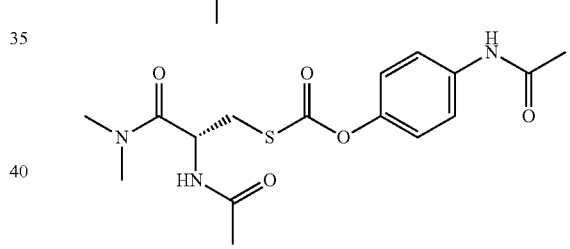

.

In another aspect, the invention provides pharmaceutical compositions including a compound of Formula (III), as described above, and at least one pharmaceutically acceptable excipient, adjuvant or carrier.

In another aspect, the invention provides methods for treating atherosclerosis, neuropathy, nephropathy, retinopathy, inflammatory disorders, Chronic Obstructive Pulmonary Disease, cardiovascular diseases, metabolic disorders, type I diabetes mellitus, type II diabetes mellitus, Latent Autoimmune Diabetes of Adulthood, metabolic syndrome, dyslipidemia, hyperglycemia, or insulin resistance in a mammal or human patient comprising administering to the mammal or human patient in need of such treatment a therapeutically effective amount of a compound of Formula (III), as described above, or a pharmaceutical composition including a compound of Formula (III) and at least one pharmaceutically acceptable excipient, adjuvant or carrier.

In another aspect, the invention provides methods for treating type II diabetes mellitus, metabolic syndrome, dyslipidemia, or insulin resistance in a mammal or human patient comprising administering to the mammal or human patient in need of such treatment a therapeutically effective amount of a compound of Formula (III), as described above, or a pharmaceutical composition including a compound of Formula (III) and at least one pharmaceutically acceptable excipient, adjuvant or carrier.

In another aspect, the invention provides methods for reducing free fatty acids, triglycerides, advanced glycated end products, ROS, lipid peroxidation, tissue and plasma TNFalpha and IL6 levels, or for delaying or preventing cardiovascular complications associated with atherosclerosis in a mammal or human patient comprising administering to the mammal or human patient in need of such treatment a therapeutically effective amount of a compound of Formula (III), as described above, or a pharmaceutical composition including a compound of Formula (III) and at least one pharmaceutically acceptable excipient, adjuvant or carrier.

In another aspect, the invention provides methods for protecting pancreatic beta-cells, preventing their impairment or failure and subsequent lower insulin secretion, in a mammal or human patient comprising administering to the mammal or human patient in need of such treatment a therapeutically effective amount of a compound of Formula (III), as described above, or a pharmaceutical composition including a compound of Formula (III) and at least one pharmaceutically acceptable excipient, adjuvant or carrier.

In another aspect, the invention provides uses for compounds of Formula (III), or pharmaceutical compositions including a compound of Formula (III) and at least one pharmaceutically acceptable excipient, adjuvant or carrier, for preparing, or for the manufacture of, a medicament for treating atherosclerosis, neuropathy, nephropathy, retinopathy, inflammatory disorders, COPD, cardiovascular diseases, metabolic disorders, type I diabetes mellitus, type II diabetes mellitus, LADA, Wolfram Syndrome 1, Wolcott-Rallison syndrome, metabolic syndrome, dyslipidemia, hyperglycemia, or insulin resistance in a mammal or human patient. The invention also provides uses for compounds of Formula (III), or pharmaceutical compositions including a compound of Formula (III) and at least one pharmaceutically acceptable excipient, adjuvant or carrier, for preparing, or for the manufacture of, a medicament for reducing free fatty acids, triglycerides, advanced glycated end products, ROS, lipid peroxidation, tissue and plasma TNFalpha and IL6 levels, or for delaying or preventing cardiovascular complications associated with atherosclerosis in a mammal or human patient. The invention also provides uses for compounds of Formula (III), or pharmaceutical compositions including a compound of Formula (III) and at least one pharmaceutically acceptable excipient, adjuvant or carrier, for preparing, or for the manufacture of, a medicament for protecting pancreatic beta-cells, preventing their impairment or failure and subsequent lower insulin secretion, in a mammal or human patient.

In another aspect, the invention provides the following compounds:

| Cpd. No. | Name |
|---|---|
| 1 | (R)-2-Acetamido-3-((2',4'-difluoro-3-(methoxycarbonyl)biphenyl-4-yloxy)carbonylthio) propanoic acid, |
| 2 | (R)-2-Acetamido-3-((2-(methoxycarbonyl)phenoxy)carbonylthio) propanoic acid, |
| 3 | (R)-2-Acetamido-3-((2',4'-difluoro-3-(benzyloxycarbonyl)biphenyl-4-yloxy)carbonylthio)propanoic acid, |
| 4 | (R)-2-Acetamido-3-((2-(benzyloxycarbonyl)phenoxy)carbonylthio) propanoic acid, |
| 5 | (+/−)-2-Acetamido-4-((2',4'-difluoro-3-(methoxycarbonyl)biphenyl-4-yloxy)carbonylthio) butanoic acid, |
| 6 | (+/−)-2-Acetamido-4-((2-(methoxycarbonyl)phenoxy)carbonylthio) butanoic acid, |
| 7 | (R)-2-Acetamido-3-((2',4'-difluoro-3-(ethoxycarbonyl)biphenyl-4-yloxy)carbonylthio) propanoic acid, |
| 8 | (R)-2-Acetamido-3-((2',4'-difluoro-3-(propoxycarbonyl)biphenyl-4-yloxy)carbonylthio) propanoic acid, |
| 9 | (R)-2-Acetamido-3-((2',4'-difluoro-3-(isopropoxycarbonyl)biphenyl-4-yloxy)carbonylthio) propanoic acid, |
| 10 | (R)-2-Acetamido-3-((2-(ethoxycarbonyl)phenoxy)carbonylthio) propanoic acid, |
| 11 | (R)-2-Acetamido-3-((2-(propoxycarbonyl)phenoxy)carbonylthio) propanoic acid, |
| 12 | (R)-2-Acetamido-3-((2-(isopropoxycarbonyl)phenoxy)carbonylthio) propanoic acid, |
| 13 | (R)-2-Acetamido-3-((2-(tert-butoxycarbonyl)phenoxy)carbonylthio) propanoic acid, |
| 14 | (R)-2-Acetamido-3-((3-(tert-butoxycarbonyl)-2',4'-difluorobiphenyl-4-yloxy)carbonylthio)propanoic acid, |
| 15 | (R)-Benzyl 4-((2-acetamido-3-methoxy-3-oxopropylthio)carbonyloxy)-2',4'-difluoro biphenyl-3-carboxylate, |
| 16 | (R)-tert-Butyl 4-((2-acetamido-3-methoxy-3-oxopropylthio)carbonyloxy)-2',4'-difluoro biphenyl-3-carboxylate, |
| 17 | (R)-2-Acetamido-3-((2',4'-difluoro-3-((4-methoxybenzyloxy)carbonyl)biphenyl-4-yloxy)carbonylthio)propanoic acid, |
| 18 | 2-(2-((2',4'-Difluoro-3-(methoxycarbonyl)biphenyl-4-yloxy)carbonylthio)propanamido)acetic acid, and |
| 19 | (R)-2-Acetamido-3-((2-(benzyloxycarbonyl)-5-(trifluoromethyl)phenoxy)carbonylthio)propanoic acid, | and pharmaceutically acceptable salts thereof.

In another aspect, the invention provides the following compounds:

| Cpd. No. | Name |
|---|---|
| 3 | (R)-2-Acetamido-3-((2',4'-difluoro-3-(benzyloxycarbonyl)biphenyl-4-yloxy)carbonylthio)propanoic acid, |
| 4 | (R)-2-Acetamido-3-((2-(benzyloxycarbonyl)phenoxy)carbonylthio) propanoic acid, |
| 5 | (+/−)-2-Acetamido-4-((2',4'-difluoro-3-(methoxycarbonyl)biphenyl-4-yloxy)carbonylthio) butanoic acid, |
| 6 | (+/−)-2-Acetamido-4-((2-(methoxycarbonyl)phenoxy)carbonylthio)butanoic acid, |
| 8 | (R)-2-Acetamido-3-((2',4'-difluoro-3-(propoxycarbonyl)biphenyl-4-yloxy)carbonylthio) propanoic acid, |
| 9 | (R)-2-Acetamido-3-((2',4'-difluoro-3-(isopropoxycarbonyl)biphenyl-4-yloxy)carbonylthio) propanoic acid, |
| 11 | (R)-2-Acetamido-3-((2-(propoxycarbonyl)phenoxy)carbonylthio) propanoic acid, |
| 12 | (R)-2-Acetamido-3-((2-(isopropoxycarbonyl)phenoxy)carbonylthio) propanoic acid, |
| 13 | (R)-2-Acetamido-3-((2-(tert-butoxycarbonyl)phenoxy)carbonylthio) propanoic acid, |
| 14 | (R)-2-Acetamido-3-((3-(tert-butoxycarbonyl)-2',4'-difluorobiphenyl-4-yloxy)carbonylthio)propanoic acid, |
| 15 | (R)-Benzyl 4-((2-acetamido-3-methoxy-3-oxopropylthio)carbonyloxy)-2',4'-difluoro biphenyl-3-carboxylate, |
| 16 | (R)-tert-Butyl 4-((2-acetamido-3-methoxy-3-oxopropylthio)carbonyloxy)-2',4'-difluoro biphenyl-3-carboxylate, |
| 17 | (R)-2-Acetamido-3-((2',4'-difluoro-3-((4-methoxybenzyloxy)carbonyl) biphenyl-4-yloxy)carbonylthio)propanoic acid, |
| 18 | 2-(2-((2',4'-Difluoro-3-(methoxycarbonyl)biphenyl-4-yloxy)carbonylthio)propanamido)acetic acid, and |
| 19 | (R)-2-Acetamido-3-((2-(benzyloxycarbonyl)-5-(trifluoromethyl)phenoxy)carbonylthio)propanoic acid, | and pharmaceutically acceptable salts thereof.

In another aspect, the invention provides pharmaceutical compositions including one or more of compounds 1-19, as described above, and at least one pharmaceutically acceptable excipient, adjuvant or carrier.

In another aspect, the invention provides methods for treating atherosclerosis, neuropathy, nephropathy, retinopathy, inflammatory disorders, Chronic Obstructive Pulmonary Disease, cardiovascular diseases, metabolic disorders, type I diabetes mellitus, type II diabetes mellitus, Latent Autoimmune Diabetes of Adulthood, metabolic syndrome, dyslipidemia, hyperglycemia, or insulin resistance in a mammal or human patient comprising administering to the mammal or human patient in need of such treatment a therapeutically effective amount of one or more of compounds 1-19, as described above, or a pharmaceutical composition including one or more of compounds 1-19 and at least one pharmaceutically acceptable excipient, adjuvant or carrier.

In another aspect, the invention provides methods for treating type II diabetes mellitus, metabolic syndrome, dyslipidemia, or insulin resistance in a mammal or human patient comprising administering to the mammal or human patient in need of such treatment a therapeutically effective amount of one or more of compounds 1-19, as described above, or a pharmaceutical composition including one or more of compounds 1-19 and at least one pharmaceutically acceptable excipient, adjuvant or carrier.

In another aspect, the invention provides methods for reducing free fatty acids, triglycerides, advanced glycated end products, ROS, lipid peroxidation, tissue and plasma TNFalpha and IL6 levels, or for delaying or preventing cardiovascular complications associated with atherosclerosis in a mammal or human patient comprising administering to the mammal or human patient in need of such treatment a therapeutically effective amount of one or more of compounds 1-19, as described above, or a pharmaceutical composition including one or more of compounds 1-19 and at least one pharmaceutically acceptable excipient, adjuvant or carrier.

In another aspect, the invention provides methods for protecting pancreatic beta-cells, preventing their impairment or failure and subsequent lower insulin secretion, in a mammal or human patient comprising administering to the mammal or human patient in need of such treatment a therapeutically effective amount of one or more of compounds 1-19, as described above, or a pharmaceutical composition including one or more of compounds 1-19 and at least one pharmaceutically acceptable excipient, adjuvant or carrier.

In another aspect, the invention provides uses for compounds 1-19, or pharmaceutical compositions including one or more of compounds 1-19 and at least one pharmaceutically acceptable excipient, adjuvant or carrier, for preparing, or for the manufacture of, a medicament for treating atherosclerosis, neuropathy, nephropathy, retinopathy, inflammatory disorders, COPD, cardiovascular diseases, metabolic disorders, type I diabetes mellitus, type II diabetes mellitus, LADA, Wolfram Syndrome 1, Wolcott-Rallison syndrome, metabolic syndrome, dyslipidemia, hyperglycemia, or insulin resistance in a mammal or human patient. The invention also provides uses for compounds 1-19, or pharmaceutical compositions including one or more of compounds 1-19 and at least one pharmaceutically acceptable excipient, adjuvant or carrier, for preparing, or for the manufacture of, a medicament for reducing free fatty acids, triglycerides, advanced glycated end products, ROS, lipid peroxidation, tissue and plasma TNFalpha and IL6 levels, or for delaying or preventing cardiovascular complications associated with atherosclerosis in a mammal or human patient. The invention also provides uses for compounds 1-19, or pharmaceutical compositions including one or more of compounds 1-19 and at least one pharmaceutically acceptable excipient, adjuvant or carrier, for preparing, or for the manufacture of, a medicament for protecting pancreatic beta-cells, preventing their impairment or failure and subsequent lower insulin secretion, in a mammal or human patient.

DEFINITIONS

As used throughout this specification and the appended claims, the following terms have the following meanings:

Terms comprising ($C_x$–$C_y$), where x and y are integers, are intended to mean moieties having a number of carbon atoms between x and y in length (in which x is less than y).

The term "($C_1$-$C_6$)alkoxy" as used herein, means a ($C_1$-$C_6$) alkyl group, as defined herein, appended to the parent molecular moiety through an oxygen atom. Representative examples of ($C_1$-$C_6$)alkoxy include, but are not limited to, methoxy, ethoxy, propoxy, 2-propoxy, butoxy, tert-butoxy, pentyloxy, and hexyloxy.

The term "($C_1$-$C_6$)alkoxy($C_1$-$C_6$)alkyl" as used herein, means a ($C_1$-$C_6$)alkoxy group, as defined herein, appended to the parent molecular moiety through a ($C_1$-$C_6$)alkyl group, as defined herein. Representative examples of ($C_1$-$C_6$)alkoxy ($C_1$-$C_6$)alkyl include, but are not limited to, methoxymethyl, ethoxymethyl, and tert-butoxymethyl.

The term "($C_1$-$C_6$)alkoxycarbonyl" as used herein, means a ($C_1$-$C_6$)alkoxy group, as defined herein, appended to the parent molecular moiety through a carbonyl group, as defined herein. Representative examples of ($C_1$-$C_6$)alkoxycarbonyl include, but are not limited to, methoxycarbonyl, ethoxycarbonyl, and tert-butoxycarbonyl.

The term "($C_1$-$C_6$)alkyl" as used herein, means a straight or branched chain hydrocarbon containing from 1 to 6 carbon atoms. Representative examples of ($C_1$-$C_6$)alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, and hexyl.

The term "($C_1$-$C_8$)alkylthio" as used herein, means a ($C_1$-$C_8$)alkyl group, as defined herein, appended to the parent molecular moiety through a sulphur atom. Representative examples of ($C_1$-$C_8$)alkylthio include, but are not limited, methylthio, ethylthio, tert-butylthio, and hexylthio.

The term "carbonyl" as used herein, means a —C(O)— group.

The term "carboxy" as used herein, means a —$CO_2$H group.

The term "($C_3$-$C_8$)cycloalkyl" as used herein, means a saturated cyclic hydrocarbon group containing from 3 to 8 carbons, examples of ($C_3$-$C_8$)cycloalkyl include cyclopropyl, cyclobutyl, cyclopentyl, cyclohexyl, cycloheptyl, and cyclooctyl. The ($C_3$-$C_8$)cycloalkyl groups of the invention are optionally substituted with 1, 2, 3, or 4 substituents independently selected from ($C_1$-$C_6$)alkoxy, ($C_1$-$C_6$)alkoxy($C_1$-$C_6$) alkyl, ($C_1$-$C_6$)alkoxycarbonyl, ($C_1$-$C_6$)alkylthio, halogen, hydroxy, hydroxycarbonyl, $NZ_1Z_2$, and phenyl, wherein the phenyl is optionally substituted with 1, 2, 3, 4, or 5 halogens.

The term "($C_3$-$C_8$)cycloalkyl($C_1$-$C_6$)alkyl" as used herein, means a ($C_3$-$C_8$)cycloalkyl group, as defined herein, appended to the parent molecular moiety through a ($C_1$-$C_6$) alkyl group, as defined herein. Representative examples of ($C_3$-$C_8$)cycloalkyl($C_1$-$C_6$)alkyl include, but are not limited to, cyclopropylmethyl, 2-cyclobutylethyl, cyclopentylmethyl, cyclohexylmethyl, and 4-cycloheptylbutyl. The ($C_3$-$C_8$)cycloalkyl($C_1$-$C_6$)alkyl groups of the invention are optionally substituted with 1, 2, 3, or 4 substituents independently selected from ($C_1$-$C_6$)alkoxy, ($C_1$-$C_6$)alkoxy($C_1$-$C_6$) alkyl, ($C_1$-$C_6$)alkoxycarbonyl, ($C_1$-$C_6$)alkylthio, halogen, hydroxy, hydroxycarbonyl, $NZ_1Z_2$, and phenyl, wherein the phenyl is optionally substituted with 1, 2, 3, 4, or 5 halogens.

The term "halo" or "halogen" as used herein, means —Cl, —Br, —I or —F.

The term "hydroxy" as used herein, means an —OH group.

The term "hydroxycarbonyl" as used herein, means a carboxy group, i.e. a COOH group.

Compounds of the invention include the alpha-amino acid cysteine, or derivatives thereof such as esters or amides, that can exist as a single stereoisomer, wherein the asymmetric or chiral center is present at the alpha-carbon. The chiral center can be designated (L) or (D) based on the Fischer projections of (L) or (D) aldose. Ernest L. Eliel and Samuel H. Wilen, *Stereochemistry of Organic Compounds*, John Wiley & Sons, Inc., New York, page 112, 1994. The chiral center can alternatively be designated (R) or (S), depending on the configuration of substituents around the chiral carbon atom. Further, compounds of the invention may contain a stereocenter that is not an alpha-carbon of an alpha-amino acid (or derivative thereof), such as alpha-lipoic acid. This center is designated (R) or (S), depending on the configuration of substituents around the chiral carbon atom. The terms (R) and (S) used herein are configurations as defined in IUPAC 1974 Recommendations for Section E, Fundamental Stereochemistry, Pure Appl. Chem., (1976), 45: 13-30. Individual stereoisomers of compounds of the invention may be prepared synthetically from commercially available starting materials that contain asymmetric or chiral centers or by preparation of racemic mixtures followed by resolution, a technique well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) direct separation of the mixture of optical enantiomers on chiral chromatographic columns, or (3) formation of a diastereomeric salt followed by selective recrystallization of one of the diastereomeric salts.

The invention also provides pharmaceutical compositions that comprise one or more compounds of the invention formulated together with one or more non-toxic pharmaceutically acceptable excipients, adjuvants, or carriers. The pharmaceutical compositions may be specially formulated for oral administration in solid or liquid form, for parenteral injection, or for rectal administration.

The term "pharmaceutically acceptable excipient, adjuvant, or carrier" as used herein means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The invention provides pharmaceutical compositions that comprise one or more compounds of the invention formulated together with one or more non-toxic pharmaceutically acceptable excipients, adjuvants, or carriers. The pharmaceutical compositions can be formulated for oral administration in solid or liquid form, for parenteral injection or for rectal administration.

The pharmaceutical compositions of this invention can be administered to humans (patients) and other mammals orally, rectally, parenterally, intracisternally, intraperitoneally, topically (as by powders, ointments or drops), bucally or as an oral or nasal spray. The term "parenterally," as used herein, refers to modes of administration that include intravenous, intramuscular, intraperitoneal, intrasternal, subcutaneous, intraarticular injection and infusion.

Pharmaceutical compositions of this invention for parenteral injection comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity may be maintained, for example, by the use of a coating such as lecithin, by the maintenance of the required particle size in the case of dispersions, and by the use of surfactants.

These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Suspensions, in addition to the active compounds, may contain suspending agents, as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

The active compounds can also be in micro-encapsulated form, if appropriate, with one or more pharmaceutically acceptable carriers as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound can be admixed with at least one inert diluent such as sucrose, lactose, or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of such composition that they release the active ingredient(s) only, or preferentially, in a certain part of the intestinal tract in a delayed manner. Examples of embedding compositions that can be used include polymeric substances and waxes.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations are also prepared by entrapping the drug in liposomes or microemulsions that are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, free fatty acids such as oleic acid are used in the preparation of injectables.

Solid dosage forms for oral administration include capsules, tablets, pills, powders, and granules. In such solid dosage forms, the active compound is mixed with at least one inert pharmaceutically acceptable carrier such as sodium citrate or calcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner.

Examples of embedding compositions that can be used include polymeric substances and waxes.

Compositions for rectal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and free fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds of the invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The compositions in liposome form may contain, in addition to the compounds of the invention, stabilizers, preservatives, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

The phrase "therapeutically effective amount" of the compound of the invention means a sufficient amount of the compound to treat metabolic disorders, at a reasonable benefit/risk ratio applicable to any medical treatment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

Actual dosage levels of active ingredients in the pharmaceutical compositions of this invention can be varied so as to obtain an amount of the active compound(s) which is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated.

The total daily dose of the compounds of this invention administered to a mammal, and particularly a human, from about 0.03 to about 20 mg/kg/day. For purposes of oral administration, more preferable doses can be in the range of from about 0.1 to about 10 mg/kg/day. If desired, the effective daily dose can be divided into multiple doses for purposes of administration, e.g. two to four separate doses per day.

The term "pharmaceutically acceptable salt," as used herein, means a positively-charged inorganic or organic cation that is generally considered suitable for human consumption. Examples of pharmaceutically acceptable cations are alkali metals (lithium, sodium and potassium), magnesium, calcium, ferrous, ferric, ammonium, alkylammonium, dialkylammonium, trialkylammonium, tetraalkylammonium, diethanolammonium, and choline. Cations may be interchanged by methods known in the art, such as ion exchange. Where compounds of the invention are prepared in the carboxylic acid form, addition of a base (such as a hydroxide or a free amine such as an alpha amino acid) will yield the appropriate salt form, (L) lysine is a preferred free amine for preparing salts of the invention.

The invention contemplates pharmaceutically active metabolites formed by in vivo biotransformation of compounds of Formulae (I)-(III). The term pharmaceutically active metabolite, as used herein, means a compound formed by the in vivo biotransformation of compounds of Formulae (I)-(III). The invention contemplates compounds of Formulae (I)-(III) and metabolites thereof. A thorough discussion of biotransformation is provided in (Goodman and Gilman's, The Pharmacological Basis of Therapeutics, seventh edition).

All patents, patent applications, and literature references cited in the specification are herein incorporated by reference in their entirety for any purpose.

The following Schemes are provided for the purposes of illustration and are not intended to limit the scope of the invention. The invention is not limited in scope by the exemplified embodiments, which are intended as illustrations of individual aspects of the invention. Various modifications of the invention in addition to those shown and described herein will become apparent to those skilled in the art from the foregoing description and accompanying drawings. Such modifications are intended to fall within the scope of the appended claims.

Preparation of Compounds of the Invention

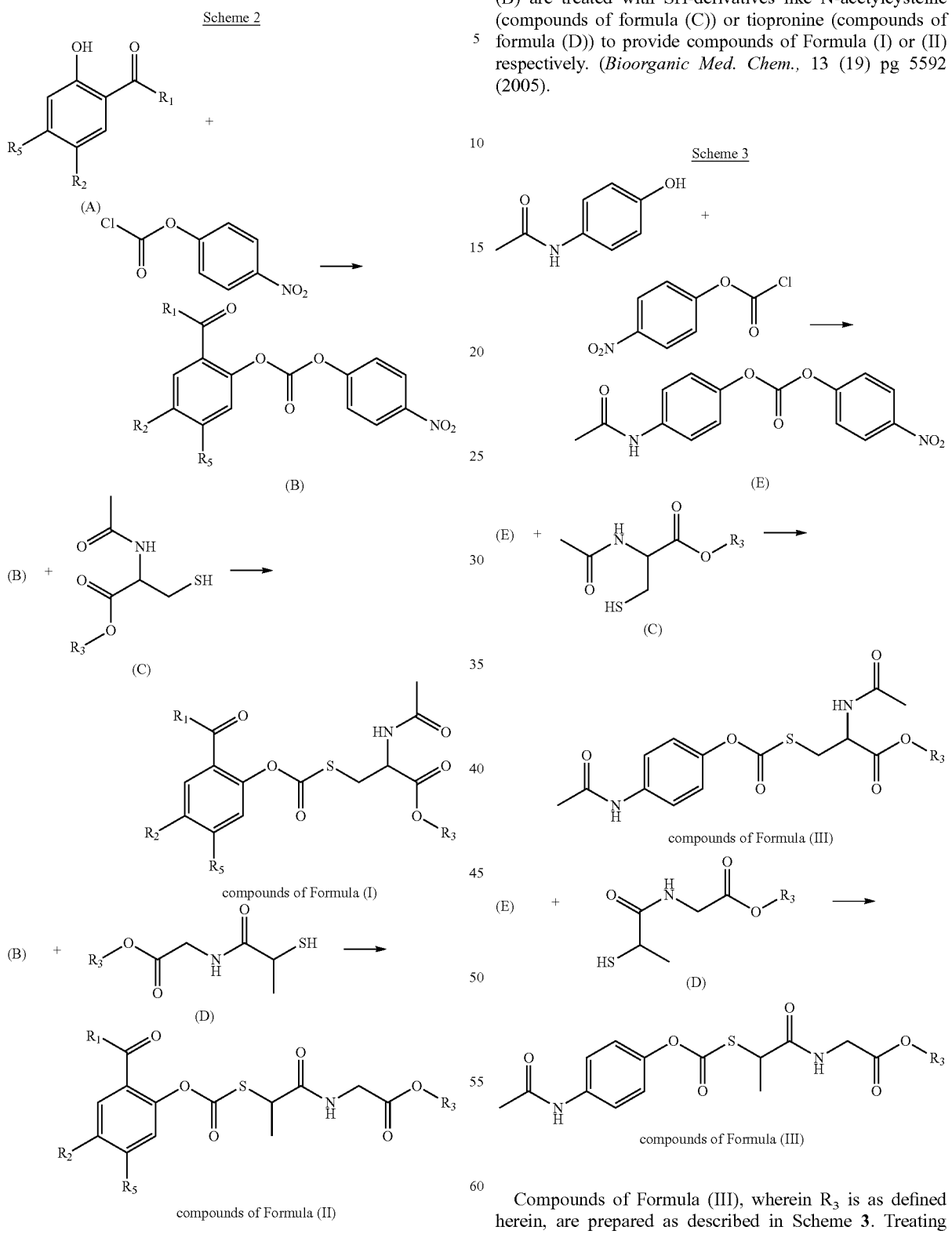

Compounds of Formula (I) and (II), wherein $R_2$ is H or 2,4-difluorophenyl, $R_5$ is H or trifluoromethyl and $R_1$ and $R_3$ are as defined herein, are prepared as described in Scheme 2. Compounds of Formula (I) or (II) are prepared by treating phenols of formula (A) with 4-nitrophenyl carbonochloridate to provide carbonates of formula (B). Carbonates of formula (B) are treated with SH-derivatives like N-acetylcysteine (compounds of formula (C)) or tiopronine (compounds of formula (D)) to provide compounds of Formula (I) or (II) respectively. (*Bioorganic Med. Chem.,* 13 (19) pg 5592 (2005).

Compounds of Formula (III), wherein $R_3$ is as defined herein, are prepared as described in Scheme 3. Treating paracetamol with 4-nitrophenyl carbonochloridate afford the carbonate of formula (E). Reacting compound of formula (E) with SH-derivatives like N-acetylcysteine (compounds of formula (C)) or tiopronine (compounds of formula (D) provide compounds of Formula (III).

EXPERIMENTAL EXAMPLES

Compounds described below were prepared from salicylic acid or diflunisal according to the following schemes: esterification of the acid group, phenol activation with 4-nitrophenyl chloroformate and thiocarbonate formation by reaction with a SH-derivative (N-acetylcysteine (NAC), N-acetylhomocysteine or tiopronine).

Example 1

(R)-2-Acetamido-3-((2',4'-difluoro-3-(methoxycarbonyl)biphenyl-4-yloxy) carbonylthio)propanoic acid

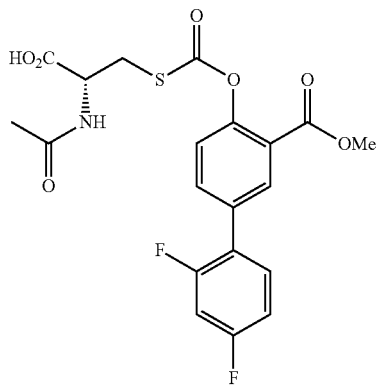 [SMILES: COC(=O)c1cc(-c2ccc(F)cc2F)ccc1OC(=O)SC[C@H](NC(C)=O)C(=O)O]

Step 1: (Methyl 2',4'-difluoro-4-hydroxybiphenyl)-3-carboxylate $H_2SO_4$ (9.6 mL, 179.12 mmol) was added to a solution of diflunisal (15.0 g, 59.95 mmol) in MeOH (200 mL). The reaction mixture was refluxed for 12 h and it was allowed to reach r.t. Solids were collected by filtration and washed with cold MeOH (20 mL) to furnish 13.42 g of methyl 2',4'-difluoro-4-hydroxybiphenyl-3-carboxylate (white solid, yield: 85%).

$^1$H NMR (CDCl$_3$, 250 MHz) δ ppm: 10.84 (s, 1H), 7.98 (s, 1H), 7.60 (d, J=8.4 Hz, 1H), 7.36 (c, J$_1$=8.8 Hz, J$_2$=6.8 Hz, 1H), 7.06 (d, J=8.8 Hz, 1H), 6.92 (m, 2H), 3.97 (s, 3H).

Step 2: (R)-2-Acetamido-3-(2',4'-difluoro-3-(methoxycarbonyl)biphenyl-4-yloxy) carbonylthio)propanoic acid (Method A)

4-Nitrophenyl chloroformate (300 mg, 1.488 mmol) was added to a solution of methyl 2',4'-difluoro-4-hydroxybiphenyl-3-carboxylate (600 mg, 2.27 mmol) and Et$_3$N (0.5 mL, 3.587 mmol) in CH$_2$Cl$_2$ (20 mL). The reaction mixture was refluxed for 4 h and allowed to reach r.t. It was diluted with CH$_2$Cl$_2$ (70 mL) and washed with NaHCO$_3$ (saturated aqueous solution, 100 mL). The organic layer was dried over Na$_2$SO$_4$ (anhydrous), filtered and concentrated. The crude residue was submitted to next step without further purification.

The crude residue from previous step was dissolved in DMF (16 mL) and NAC (360 mg, 2.20 mmol) was added. The reaction mixture was stirred at r.t. for 15 min and Et$_3$N (1.0 mL, 7.11 mmol) was added. The reaction was stirred at r.t. overnight (16 h). It was poured into H$_2$O (50 mL), taken up to pH=3 by adding HCl (5% aqueous solution) and it was extracted with CH$_2$Cl$_2$ (2×40 mL). The organic layer was dried over Na$_2$SO$_4$ (anhydrous), filtered and concentrated (DMF was concentrated off at high vacuum pump). The crude residue was flash chromatographed on SiO$_2$ (25% MeOH/CH$_2$Cl$_2$) to furnish a solid that was slurred with Et$_2$O (6 mL), to furnish 88 mg of (R)-2-acetamido-3-((2',4'-difluoro-3-(methoxycarbonyl)biphenyl-4-yloxy)carbonyl thio)propanoic acid (off-white solid, yield: 13%).

$^1$H NMR (CD$_3$OD, 250 MHz) δ ppm: 8.14 (s, 1H), 7.82 (d, J=8.5 Hz, 1H), 7.59 (m, 1H), 7.36 (d, J=8.5 Hz, 1H), 7.18-7.06 (m, 2H), 4.63 (bs, 1H), 3.94 (s, 3H), 3.66 (d, J=13.1 Hz, 1H), 3.30 (d, J=13.1 Hz, 1H), 2.0 (s, 3H).

EI MS: m/z=454 (M+1).

Example 2

(R)-2-Acetamido-3-((2-(methoxycarbonyl)phenoxy)carbonylthio)propanoic acid

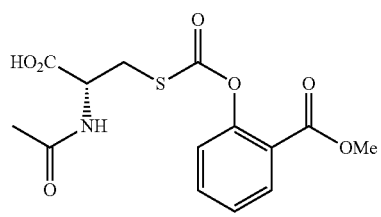 [SMILES: COC(=O)c1ccccc1OC(=O)SC[C@H](NC(C)=O)C(=O)O]

Step 1: Methyl 2-hydroxybenzoate $H_2SO_4$ (4.0 mL, 74.63 mmol) was added to a solution of salicylic acid (5.0 g, 36.20 mmol) in MeOH (60 mL). The reaction mixture was refluxed for 20 h, allowed to reach r.t., poured into H$_2$O (100 mL) and extracted with CH$_2$Cl$_2$ (120 mL). The organic layer was dried over Na$_2$SO$_4$ (anhydrous), filtered and concentrated. The crude residue was flash chromatographed on SiO$_2$ (5% EtOAc/hexanes) to furnish 5.44 g of methyl 2-hydroxybenzoate (colourless oil, yield: 98%).

$^1$H NMR (CDCl$_3$, 250 MHz) δ ppm: 10.75 (s, 1H), 7.84 (dt, J$_1$=6.6 Hz, J$_2$=8.2 Hz, 1H), 7.45 (m, 1H), 6.98 (d, J=8.2 Hz, 1H), 6.87 (m, 1H), 3.95 (s, 3H).

Step 2: (R)-2-Acetamido-3-((2-(methoxycarbonyl)phenoxy)carbonylthio) propanoic acid The compound was synthesized from methyl 2-hydroxybenzoate and NAC following the experimental procedure detailed in Method A. It was purified by flash chromatography on SiO$_2$ (5% MeOH/CH$_2$Cl$_2$) to furnish (R)-2-acetamido-3-((2-(methoxycarbonyl)phenoxy)carbonylthio)propanoic acid (white solid, yield: 68%).

$^1$H NMR (CD$_3$OD, 250 MHz) δ ppm: 7.98 (dd, J$_1$=8.0 Hz, J$_2$=7.7 Hz, 1H), 7.63 (t, J=8.0 Hz, 1H), 7.40 (t, J=7.7 Hz, 1H), 7.22 (d, J=8.2 Hz, 1H), 4.55 (m, 1H), 3.86 (s, 3H), 3.63 (d, J=13.7 Hz, 1H), 3.26 (d, J=13.7 Hz, 1H), 2.0 (s, 3H)

EI MS: m/z=342 (M+1). .

Example 3

(R)-2-Acetamido-3-((2',4'-difluoro-3-(benzyloxycarbonyl)biphenyl-4-yloxy)carbonylthio)propanoic acid

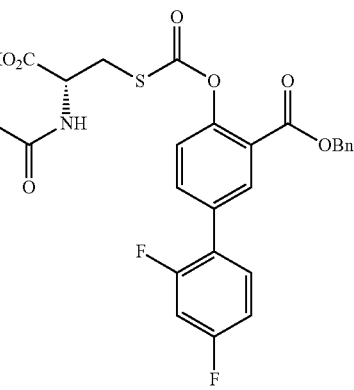

Step 1: Benzyl 2',4'-difluoro-4-hydroxybiphenyl-3-carboxylate

BnBr (1.35 mL, 11.286 mmol) was added to a solution of diflunisal (2.0 g, 7.99 mmol) in TBAF (10 mL, 1 M solution in THF) and the reaction mixture was stirred at r.t. overnight (18 h). The organic layer was poured into H$_2$O (15 mL) and extracted with EtOAc (40 mL). It was dried over Na$_2$SO$_4$ (anhydrous), filtered and concentrated. The crude residue was flash chromatographed on SiO$_2$ (hexanes) to furnish 2.09 g of benzyl 2',4'-difluoro-4-hydroxybiphenyl-3-carboxylate (white solid, yield: 77%).

$^1$H NMR (CDCl$_3$, 250 MHz) δ ppm: 10.84 (s, 1H), 8.00 (s, 1H), 7.60 (m, 1H), 7.29-7.47 (m, 6H), 7.06 (d, J=8.4 Hz, 1H), 6.91 (m, 2H), 5.42 (s, 2H).

Step 2: (R)-2-Acetamido-3-((2',4'-difluoro-3-(benzyloxycarbonyl)biphenyl-4-yloxy)carbonylthio)propanoic acid The compound was synthesized from benzyl 2',4'-difluoro-4-hydroxybiphenyl-3-carboxylate and NAC following the experimental procedure detailed in Method A. It was purified by flash chromatography on SiO$_2$ (7% MeOH/CH$_2$Cl$_2$) to furnish (R)-2-acetamido-3-((2',4'-difluoro-3-(benzyloxycarbonyl)biphenyl-4-yloxy)carbonylthio)propanoic acid (white solid, yield: 9%).

$^1$H NMR (CD$_3$OD, 250 MHz) δ ppm: 8.11 (s, 1H), 7.77 (m, 1H), 7.58-7.27 (m, 7H), 7.06 (m, 2H), 5.35 (s, 2H), 4.60 (m, 1H), 3.51 (m, 1H), 3.18 (m, 1H), 1.96 (s, 3H).

EI MS: m/z=530 (M+1).

Example 4

(R)-2-Acetamido-3-((2-(benzyloxycarbonyl)phenoxy)carbonylthio) propanoic acid

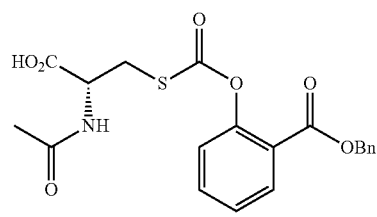 [SMILES: CC(=O)N[C@@H](CSC(=O)Oc1ccccc1C(=O)OCc1ccccc1)C(=O)O]

Step 1: Benzyl 2-hydroxybenzoate

BnBr (1.75 mL, 14.631 mmol) was added to a solution of salicylic acid (2.0 g, 14.625 mmol) in TBAF (17.5 mL, 1 M solution in THF) and the reaction mixture was stirred at r.t. overnight (16 h). The organic layer was poured into H$_2$O (100 mL) and extracted with EtOAc (70 mL). It was dried over Na$_2$SO$_4$ (anhydrous), filtered and concentrated. The crude residue was flash chromatographed on SiO$_2$ (2% EtOAc/hexanes) to furnish 2.53 g of benzyl 2-hydroxybenzoate (colourless oil, yield: 76%).

$^1$H NMR (CDCl$_3$, 250 MHz) δ ppm: 10.75 (s, 1H), 7.87 (t, J=7.1 Hz, 1H), 7.42 (m, 6H), 6.97 (t, J=7.4 Hz, 1H), 6.86 (c, J=7.1 Hz, 1H), 5.38 (s, 2H).

Step 2: (R)-2-Acetamido-3-((2-(benzyloxycarbonyl)phenoxy)carbonylthio) propanoic acid The compound was synthesized from benzyl 2-hydroxybenzoate and NAC following the experimental procedure detailed in Method A. It was purified by flash chromatography on SiO$_2$ (10% MeOH/CH$_2$Cl$_2$) to furnish (R)-2-acetamido-3-((2-(benzyloxycarbonyl)phenoxy) carbonylthio)propanoic acid (white solid, yield: 22%).

$^1$H NMR (CD$_3$OD, 250 MHz) δ ppm: 8.00 (d, J=7.4 Hz, 1H), 7.64 (t, J=7.4 Hz, 1H), 7.48-7.28 (m, 6H), 7.22 (d, J=8.8 Hz, 1H), 5.32 (s, 2H), 4.55 (m, 1H), 3.52 (d, J=13.7 Hz, 1H), 3.17 (d, J=13.7 Hz, 1H), 1.96 (s, 3H).

EI MS: m/z=418 (M+1).

Example 5

(+/−)-2-Acetamido-4-((2',4'-difluoro-3-(methoxycarbonyl)biphenyl-4-yloxy)carbonylthio)butanoic acid (GMC-300)

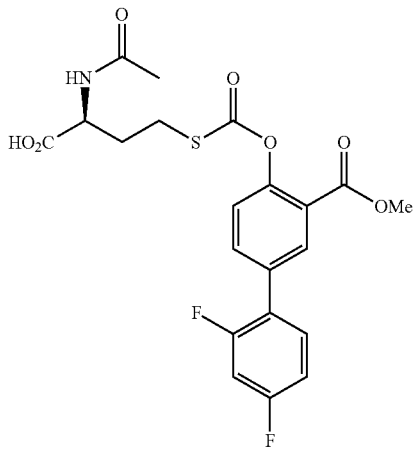 [SMILES: COC(=O)c1cc(-c2ccc(F)cc2F)ccc1OC(=O)SCC[C@H](NC(C)=O)C(=O)O]

Step 1: DL-N-Acetylhomocysteine

NaOH (1 M deoxygenated aqueous solution, 100 mL) was dropwise added to DL-N-acetylhomocysteine thiolactone (4.00 g, 25.124 mmol). Addition time: 15 min. The reaction mixture was warmed up to 50° C. and allowed to react for 30 min. The reaction was cooled down to 0° C., acidified with HCl (10% aqueous solution, 30 mL) and the product was extracted with nBuOH (4×70 mL). The organic layer was dried over $Na_2SO_4$ (anhydrous), filtered and concentrated. The crude residue was slurred with $Et_2O$/hexanes (1:3, 150 mL) to furnish 4.00 g of DL-N-acetylhomocysteine (white solid, yield: 90%).

$^1$H NMR ($D_2O$, 250 MHz) δ ppm: 6.04 (m, 1H), 4.05 (m, 2H), 3.44-3.60 (m, 5H).

Step 2: (+/−)-2-Acetamido-4-((2',4'-difluoro-3-(methoxycarbonyl)biphenyl-4-yloxy)carbonylthio) butanoic acid The compound was synthesized from methyl 2',4'-difluoro-4-hydroxybiphenyl-3-carboxylate and N-acetylhomocysteine following the experimental procedure detailed in Method A. It was purified by flash chromatography on $SiO_2$ (0.6% MeOH/$CH_2Cl_2$) to furnish (+/−)-2-acetamido-4-(2',4'-difluoro-3-(methoxycarbonyl)biphenyl-4-yloxy)carbonylthio)butanoic acid (off-white solid, yield: 15%).

$^1$H NMR ($CD_3OD$, 250 MHz) δ ppm: 8.10 (s, 1H), 7.77 (d, J=8.1 Hz, 1H), 7.56 (m, 1H), 7.32 (d, J=8.1 Hz, 1H), 7.10 (m, 2H), 4.52 (m, 1H), 3.90 (s, 3H), 3.04 (m, 2H), 2.30 (m, 1H), 2.10 (m, 1H), 2.00 (s, 3H).

EI MS: m/z=468 (M+1).

Example 6

(+/−)-2-Acetamido-4-((2-(methoxycarbonyl)phenoxy)carbonylthio) butanoic acid

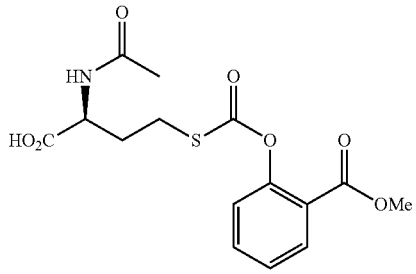 [SMILES: COC(=O)c1ccccc1OC(=O)SCC[C@H](NC(C)=O)C(=O)O]

The compound was synthesized from methyl 2-hydroxybenzoate and N-acetylhomocysteine following the experimental procedure detailed in Method A. It was purified by flash chromatography on $SiO_2$ (3→10% MeOH/$CH_2Cl_2$) to furnish (+/−)-2-acetamido-4-((2-(methoxycarbonyl)phenoxy)carbonylthio)butanoic acid (yellow-coloured oil, yield: 13%).

$^1$H NMR ($CDCl_3$, 250 MHz) δ ppm: 8.01 (d, J=8.0 Hz, 1H), 7.58 (t, J=7.7 Hz, 1H), 7.35 (t, J=7.7 Hz, 1H), 7.17 (d, J=8.0 Hz, 1H), 6.62 (s, 1H), 4.62 (m, 1H), 3.90 (s, 3H), 3.00 (m, 2H), 2.33 (m, 1H), 2.18 (m, 1H), 2.05 (s, 3H).

EI MS: m/z=356 (M+1).

Example 7

(R)-2-Acetamido-3-((2',4'-difluoro-3-(ethoxycarbonyl)biphenyl-4-yloxy)carbonylthio)propanoic acid

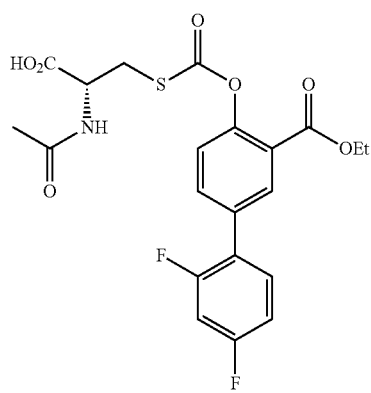 [SMILES: CCOC(=O)c1cc(-c2ccc(F)cc2F)ccc1OC(=O)SC[C@H](NC(C)=O)C(=O)O]

Step 1: Ethyl 2',4'-difluoro-4-hydroxybiphenyl-3-carboxylate $H_2SO_4$ (1 mL, 18.76 mmol) was added to a solution of diflunisal (1.50 g, 5.995 mmol) in EtOH (50 mL). The reaction mixture was refluxed for 2 days, allowed to reach r.t., and diluted with $CH_2Cl_2$ (200 mL). The organic layer was washed with $Na_2CO_3$ (1 M aqueous solution, 200 mL). It was dried over $Na_2SO_4$ (anhydrous), filtered and concentrated to furnish 1.30 g of ethyl 2',4'-difluoro-4-hydroxybiphenyl-3-carboxylate (white solid, yield: 78%).

$^1$H NMR (CDCl$_3$, 250 MHz) δ ppm: 10.92 (s, 1H), 7.97 (m, 1H), 7.59 (dt, J$_1$=6.6 Hz, J$_2$=8.5 Hz, 1H), 7.37 (m, 1H), 7.05 (d, J=8.5 Hz, 1H), 6.86-6.99 (m, 2H), 4.44 (c, J=7.1 Hz, 2H), 1.43 (t, J=7.1 Hz, 3H).

Step 2: (R)-2-Acetamido-3-(2',4'-difluoro-3-(ethoxycarbonyl)biphenyl-4-yloxy) carbonylthio)propanoic acid The compound was synthesized from ethyl 2',4'-difluoro-4-hydroxybiphenyl-3-carboxylate and NAC following the experimental procedure detailed in Method A. It was purified by flash chromatography on SiO$_2$ (3→7% MeOH/CH$_2$Cl$_2$) to furnish (R)-2-acetamido-3-((2',4'-difluoro-3-(ethoxycarbonyl)biphenyl-4-yloxy)carbonylthio)propanoic acid (off-white solid, yield: 28%).

$^1$H NMR (CD$_3$OD, 250 MHz) δ ppm: 8.09 (m, 1H), 7.76 (m, 1H), 7.55 (m, 1H), 7.32 (d, J=8.4 Hz, 1H), 7.05-7.16 (m, 2H), 4.58 (m, 1H), 4.35 (c, J=7.0 Hz, 1H), 3.66 (m, 1H), 3.25 (m, 1H), 2.01 (s, 3H), 1.38 (t, J=7.0 Hz, 3H).

EI MS: m/z=468 (M+1).

Example 8

(R)-2-Acetamido-3-((2',4'-difluoro-3-(propoxycarbonyl)biphenyl-4-yloxy) carbonylthio)propanoic acid (GMC-316)

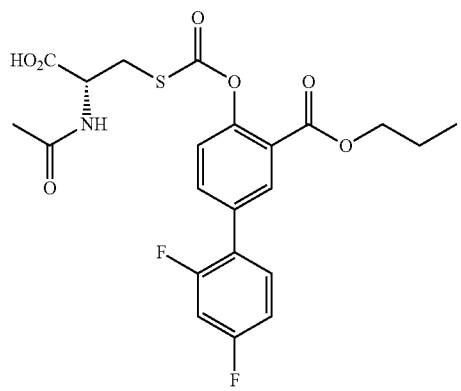 [SMILES: CCCOC(=O)c1cc(-c2ccc(F)cc2F)ccc1OC(=O)SC[C@H](NC(C)=O)C(=O)O]

Step 1: Propyl 2',4'-difluoro-4-hydroxybiphenyl-3-carboxylate

CDI (972 mg, 5.99 mmol) was added to a solution of diflunisal (1.50 g, 5.99 mmol) in DMF (30 mL). The reaction mixture was stirred at 50° C. for 2 h and n-PrOH (1.13 mL, 14.97 mmol) was dropwise added. The reaction mixture was stirred at 50° C. for 3 h and allowed to reach r.t. It was poured into H$_2$O (50 mL) and extracted with Et$_2$O (2×50 mL). The organic layer was washed with NaHCO$_3$ (20 mL, saturated aqueous solution), dried over Na$_2$SO$_4$ (anhydrous), filtered and concentrated. The crude residue was flash chromatographed on SiO$_2$ (2% EtOAc/hexanes) to furnish 1.33 g of propyl 2',4'-difluoro-4-hydroxybiphenyl-3-carboxylate (yellow-coloured oil, yield: 76%).

$^1$H NMR (CDCl$_3$, 250 MHz) δ ppm: 10.92 (s, 1H), 7.98 (m, 1H), 7.59 (dt, J$_1$=6.9 Hz, J$_2$=8.8 Hz, 1H), 7.36 (m, 1H), 7.05 (d, J=8.8 Hz, 1H), 6.86-7.00 (m, 2H), 4.33 (t, J=6.6 Hz, 2H), 1.82 (m, 2H), 1.04 (t, J=7.4 Hz, 3H).

Step 2: (R)-2-Acetamido-3-((2',4'-difluoro-3-(propoxycarbonyl)biphenyl-4-yloxy) carbonylthio)propanoic acid The compound was synthesized from propyl 2',4'-difluoro-4-hydroxybiphenyl-3-carboxylate and NAC following the experimental procedure detailed in Method A. It was purified by flash chromatography on SiO$_2$ (3→5% MeOH/CH$_2$Cl$_2$) to furnish (R)-2-acetamido-3-((2',4'-difluoro-3-(propoxycarbonyl)biphenyl-4-yloxy)carbonylthio)propanoic acid (off-white solid, yield: 16%).

$^1$H NMR (CD$_3$OD, 250 MHz) δ ppm: 8.10 (m, 1H), 7.77 (dt, J$_1$=8.6 Hz, J$_2$=6.5 Hz), 7.55 (m, 1H), 7.32 (d, J=8.6 Hz, 1H), 7.06-7.15 (m, 2H), 4.56 (m, 1H), 4.26 (t, J=6.5 Hz, 2H), 3.65 (dd, J$_1$=13.5 Hz, J$_2$=4.3 Hz, 1H), 3.26 (m, 1H), 2.01 (s, 3H), 1.79 (m, 2H), 1.01 (t, J=7.6 Hz, 3H).

EI MS: m/z=480 (M−1).

Example 9

(R)-2-Acetamido-3-((2',4'-difluoro-3-(isopropoxycarbonyl)biphenyl-4-yloxy) carbonylthio)propanoic acid

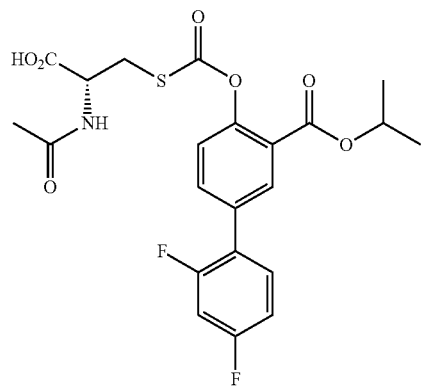 [SMILES: CC(=O)N[C@@H](CSC(=O)Oc1ccc(-c2ccc(F)cc2F)cc1C(=O)OC(C)C)C(=O)O]

Step 1: Isopropyl 2',4'-difluoro-4-hydroxybiphenyl-3-carboxylate

CDI (972 mg, 5.99 mmol) was added to a solution of diflunisal (1.50 g, 5.99 mmol) in DMF (30 mL). The reaction mixture was stirred at 50° C. for 2 h and isopropyl alcohol (1.15 mL, 14.97 mmol) was dropwise added. The reaction mixture was stirred at 50° C. for 3 h and allowed to reach r.t. It was poured into H$_2$O (50 mL) and extracted with Et$_2$O (2×60 mL). The organic layer was washed with NaHCO$_3$ (20 mL, saturated aqueous solution), dried over Na$_2$SO$_4$ (anhydrous), filtered and concentrated. The crude residue was flash chromatographed on SiO$_2$ (15% EtOAc/hexanes) to furnish 720 mg of isopropyl 2',4'-difluoro-4-hydroxybiphenyl-3-carboxylate (white solid, yield: 41%).

$^1$H NMR (CDCl$_3$, 250 MHz) δ ppm: 11.03 (s, 1H), 7.94 (m, 1H), 7.58 (dt, J$_1$=8.5 Hz, J$_2$=8.0 Hz, 1H), 7.37 (m, 1H), 7.05 (d, J=8.8 Hz, 1H), 6.93 (m, 2H), 5.31 (m, 1H), 1.41 (s, 3H), 1.39 (s, 3H).

Step 2: (R)-2-Acetamido-3-((2',4'-difluoro-3-(isopropoxycarbonyl)biphenyl-4-yloxy)carbonylthio)propanoic acid The compound was synthesized from isopropyl 2',4'-difluoro-4-hydroxybiphenyl-3-carboxylate and NAC following the experimental procedure detailed in Method A. It was purified by flash chromatography on SiO$_2$ (0→10% MeOH/CH$_2$Cl$_2$) to give a solid that was slurred with cold hexanes, to furnish (R)-2-acetamido-3-((2',4'-difluoro-3-(isopropoxycarbonyl)biphenyl-4-yloxy)carbonylthio)propanoic acid (off-white solid, yield: 38%).

$^1$H NMR (CD$_3$OD, 250 MHz) δ ppm: 8.07 (m, 1H), 7.76 (m, 1H), 7.55 (m, 1H), 7.32 (d, J=8.5 Hz, 1H), 7.05-7.14 (m, 2H), 5.21 (m, 1H), 4.60 (m, 1H), 3.64 (dd, J$_1$=13.4 Hz, J$_2$=4.1 Hz, 1H), 3.26 (m, 1H), 2.00 (s, 3H), 1.37 (s, 3H), 1.35 (s, 3H).

EI MS: m/z=499 (M+18).

Example 10

(R)-2-Acetamido-3-((2-(ethoxycarbonyl)phenoxy)carbonylthio) propanoic acid

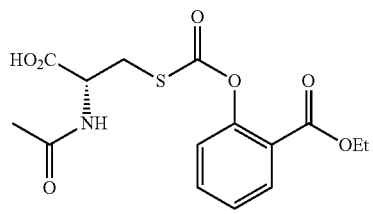 [SMILES: CCOC(=O)c1ccccc1OC(=O)SC[C@H](NC(C)=O)C(=O)O]

Step 1: Ethyl 2-hydroxybenzoate

H$_2$SO$_4$ (1.5 mL, 28.14 mmol) was added to a solution of salicylic acid (1.50 g, 10.860 mmol) in EtOH (50 mL). The reaction mixture was refluxed for 2 days, allowed to reach r.t., and it was diluted with CH$_2$Cl$_2$ (200 mL). The organic layer was washed with Na$_2$CO$_3$ (1 M aqueous solution, 200 mL). It was dried over Na$_2$SO$_4$ (anhydrous), filtered and concentrated to furnish 1.26 g of ethyl 2-hydroxybenzoate (yellow-coloured oil, yield: 70%).

$^1$H NMR (CDCl$_3$, 250 MHz) δ ppm: 10.89 (s, 1H), 7.84 (dd, J$_1$=8.5 Hz, J$_2$=8.0 Hz, 1H), 7.43 (t, J=8.5 Hz, 1H), 6.96 (d, J=8.5 Hz, 1H), 6.86 (t, J=7.3 Hz, 1H), 4.40 (c, J=7.1 Hz, 2H), 1.40 (t, J=7.1 Hz, 3H).

Step 2: (R)-2-Acetamido-3-((2-(ethoxycarbonyl)phenoxy)carbonylthio) propanoic acid The compound was synthesized from ethyl 2-hydroxybenzoate and NAC following the experimental procedure detailed in Method A. It was purified by flash chromatography on SiO$_2$ (0→10% MeOH/CH$_2$Cl$_2$) to give a solid that was slurred with cold Et$_2$O/hexanes (1:10), to furnish (R)-2-acetamido-3-((2-(ethoxycarbonyl)phenoxy)carbonylthio)propanoic acid (off-white solid, yield: 31%).

$^1$H NMR (CD$_3$OD, 250 MHz) δ ppm: 7.98 (dd, J$_1$=8.0 Hz, J$_2$=7.7 Hz, 1H), 7.63 (dt, J$_1$=8.0 Hz, J$_2$=7.4 Hz, 1H), 7.40 (dt, J$_1$=8.0 Hz, J$_2$=7.4 Hz, 1H), 7.23 (dd, J$_1$=8.0 Hz, J$_2$=7.7 Hz, 1H), 4.70 (m, 1H), 4.33 (c, J=7.1 Hz, 2H), 3.58 (m, 1H), 3.24 (m, 1H), 2.00 (s, 3H), 1.37 (t, J=7.1 Hz, 3H).

EI MS: m/z=356 (M+1).

Example 11

(R)-2-Acetamido-3-((2-(propoxycarbonyl)phenoxy) carbonylthio) propanoic acid

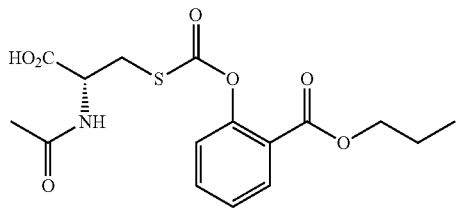 [SMILES: CCCOC(=O)c1ccccc1OC(=O)SC[C@H](NC(C)=O)C(=O)O]

Step 1: Propyl 2-hydroxybenzoate

CDI (2.34 g, 14.48 mmol) was added to a solution of salicylic acid (2.00 g, 14.48 mmol) in DMF (40 mL). The reaction mixture was stirred at 50° C. for 4 h and PrOH (2.72 mL, 36.20 mmol) was dropwise added. The reaction mixture was stirred at 50° C. for 16 h and allowed to reach r.t. It was poured into H$_2$O (20 mL) and extracted with Et$_2$O (2×40 mL). The organic layer was washed with NaHCO$_3$ (20 mL, saturated aqueous solution), dried over Na$_2$SO$_4$ (anhydrous), filtered and concentrated. The crude residue was flash chromatographed on SiO$_2$ (5% EtOAc/hexanes) to furnish 2.05 g of propyl 2-hydroxybenzoate (colourless oil, yield: 79%).

$^1$H NMR (CDCl$_3$, 250 MHz) δ ppm: 10.85 (s, 1H), 7.85 (dd, J$_1$=8.5 Hz, J$_2$=8.0 Hz, 1H), 7.45 (t, J=8.5 Hz, 1H), 6.97 (d, J=8.8 Hz, 1H), 6.88 (t, J=8.0 Hz, 1H), 4.31 (t, J=6.6 Hz, 2H), 1.81 (m, 2H), 1.04 (t, J=7.4 Hz, 3H).

Step 2: (R)-2-Acetamido-3-((2-(propoxycarbonyl)phenoxy)carbonylthio)propanoic acid The compound was synthesized from propyl 2-hydroxybenzoate and NAC following the experimental procedure detailed in Method A. It was purified by flash chromatography on SiO$_2$ (0→6% MeOH/CH$_2$Cl$_2$) to give a solid that was slurred with cold hexanes, to furnish (R)-2-acetamido-3-((2-(propoxycarbonyl)phenoxy)carbonylthio)propanoic acid (off-white solid, yield: 17%).

$^1$H NMR (CD$_3$OD, 250 MHz) δ ppm: 7.99 (m, 1H), 7.64 (m, 1H), 7.41 (m, 1H), 7.23 (m, 1H), 4.72 (m, 1H), 4.25 (t, J=6.6 Hz, 2H), 3.58 (m, 1H), 3.23 (m, 1H), 2.00 (s, 3H), 1.78 (m, 2H), 1.00 (t, J=7.4 Hz, 3H).

EI MS: m/z=370 (M+1).

Example 12

(R)-2-Acetamido-3-((2-(isopropoxycarbonyl)phenoxy)carbonylthio) propanoic acid

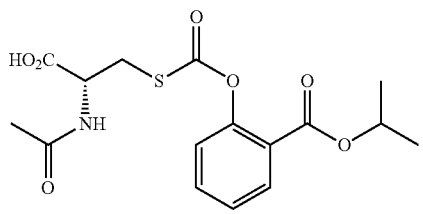 [SMILES: CC(=O)N[C@@H](CSC(=O)Oc1ccccc1C(=O)OC(C)C)C(=O)O]

Step 1: Isopropyl 2-hydroxybenzoate

CDI (2.34 g, 14.48 mmol) was added to a solution of salicylic acid (2.00 g, 14.48 mmol) in DMF (40 mL). The reaction mixture was stirred at 50° C. for 4 h and isopropyl alcohol (2.80 mL, 36.20 mmol) was dropwise added. The reaction mixture was stirred at 50° C. for 16 h and allowed to reach r.t. It was poured into $H_2O$ (50 mL) and extracted with $Et_2O$ (2×40 mL). The organic layer was washed with $NaHCO_3$ (20 mL, saturated aqueous solution), dried over $Na_2SO_4$ (anhydrous), filtered and concentrated. The crude residue was flash chromatographed on $SiO_2$ (5% EtOAc/hexanes) to furnish 1.395 g of isopropyl 2-hydroxybenzoate (colourless oil, yield: 54%).

$^1$H NMR (CDCl$_3$, 250 MHz) δ ppm: 10.94 (s, 1H), 7.84 (d, J=8.0 Hz, 1H), 7.44 (t, J=8.8 Hz, 1H), 6.97 (d, J=8.2 Hz, 1H), 6.87 (t, J=8.2 Hz, 1H), 5.28 (m, 1H), 1.40 (s, 3H), 1.37 (s, 3H).

Step 2: (R)-2-Acetamido-3-((2-(isopropoxycarbonyl)phenoxy)carbonylthio) propanoic acid The compound was synthesized from isopropyl 2-hydroxybenzoate and NAC following the experimental procedure detailed in Method A. It was purified by flash chromatography on $SiO_2$ (3% MeOH/$CH_2Cl_2$) to furnish (R)-2-acetamido-3-((2-(isopropoxycarbonyl)phenoxy)carbonylthio)propanoic acid (white solid, yield: 23%).

$^1$H NMR (CD$_3$OD, 250 MHz) δ ppm: 7.96 (dd, J$_1$=8.0 Hz, J$_2$=7.7 Hz, 1H), 7.63 (dt, J$_1$=7.7 Hz, J$_2$=7.4, 1H), 7.40 (dt, J$_1$=7.7 Hz, J$_2$=7.4, 1H), 7.23 (dd, J$_1$=8.0 Hz, J$_2$=7.7 Hz, 1H), 5.20 (m, 1H), 4.73 (m, 1H), 3.58 (dd, J=4.7 Hz, 1H), 3.25 (m, 1H), 2.00 (s, 3H), 1.36 (s, 3H), 1.34 (s, 3H).

EI MS: m/z=370 (M+1).

Example 13

(R)-2-Acetamido-3-((2-(tert-butoxycarbonyl)phenoxy)carbonylthio) propanoic acid

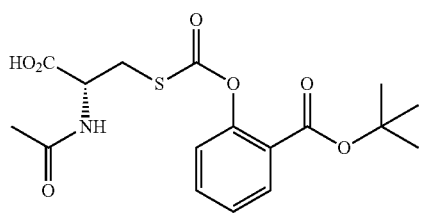 [SMILES: CC(=O)N[C@@H](CSC(=O)Oc1ccccc1C(=O)OC(C)(C)C)C(=O)O]

Step 1: tert-Butyl 2-hydroxybenzoate

CDI (2.40 g, 14.79 mmol) was added to a solution of salicylic acid (2.02 g, 14.62 mmol) in DMF (20 mL). The reaction mixture was stirred at 50° C. for 30 min and tert-butyl alcohol (2.80 mL, 29.84 mmol) and DBU (4.4 mL, 29.45 mmol) were dropwise added. The reaction mixture was stirred at 50° C. for 16 h and allowed to reach r.t. It was poured into $NaHCO_3$ (100 mL, saturated aqueous solution) and extracted with EtOAc (70 mL). The organic layer was dried over $Na_2SO_4$ (anhydrous), filtered and concentrated. The crude residue was flash chromatographed on $SiO_2$ (5% EtOAc/hexanes) to furnish 2.089 g of tert-butyl 2-hydroxybenzoate (colourless oil, yield: 73%).

$^1$H NMR (CDCl$_3$, 250 MHz) δ ppm: 7.78 (d, J=8.0 Hz, 1H), 7.41 (t, J=7.1 Hz, 1H), 6.95 (d, J=7.1 Hz, 1H), 6.84 (t, J=8.0 Hz, 1H), 1.61 (s, 9H).

Step 2: (R)-2-Acetamido-3-((2-(tert-butoxycarbonyl)phenoxy)carbonylthio)propanoic acid The compound was synthesized from tert-butyl 2-hydroxybenzoate and NAC following the experimental procedure detailed in Method A. It was purified by flash chromatography on $SiO_2$ (5% MeOH/$CH_2Cl_2$) to furnish (R)-2-acetamido-3-((2-(tert-butoxycarbonyl)phenoxy)carbonylthio)propanoic acid (white solid, yield: 40%).

$^1$H NMR (CD$_3$OD, 250 MHz) δ ppm: 7.85 (dd, J=7.7 Hz, 1H), 7.59 (dt, J=8.0 Hz, 1H), 7.38 (dt, J=7.7 Hz, 1H), 7.20 (d, J=8.0 Hz, 1H), 4.68 (m, 1H), 3.59 (dd, J$_1$=14.3 Hz, J$_2$=4.9 Hz, 1H), 3.23 (m, 1H), 1.98 (s, 3H), 1.57 (s, 9H).

Example 14

(R)-2-Acetamido-3-((3-(tert-butoxycarbonyl)-2',4'-difluorobiphenyl-4-yloxy)carbonylthio)propanoic acid

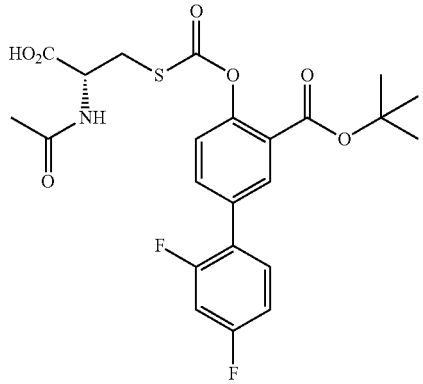 [SMILES: CC(=O)N[C@@H](CSC(=O)Oc1ccc(-c2ccc(F)cc2F)cc1C(=O)OC(C)(C)C)C(=O)O]

Step 1: tert-Butyl 2',4'-difluoro-4-hydroxybiphenyl-3-carboxylate

CDI (1.29 g, 7.99 mmol) was added to a solution of diflunisal (2.02 g, 8.07 mmol) in DMF (20 mL). The reaction mixture was stirred at 50° C. for 30 min and tert-butyl alcohol (1.50 mL, 14.97 mmol) and DBU (2.40 mL, 16.064 mmol) were dropwise added. The reaction mixture was stirred at 50° C. for 20 h and allowed to reach r.t. It was poured into NaHCO$_3$ (100 mL, saturated aqueous solution) and extracted with EtOAc (100 mL). The organic layer was dried over Na$_2$SO$_4$ (anhydrous), filtered and concentrated. The crude residue was flash chromatographed on SiO$_2$ (5% EtOAc/hexanes) to furnish 1.677 g of ten-butyl 2',4'-difluoro-4-hydroxybiphenyl-3-carboxylate (colourless oil, yield: 68%).

$^1$H NMR (CDCl$_3$, 250 MHz) δ ppm: 11.40 (s, 1H), 7.88 (m, 1H), 7.55 (dt, J=8.8 Hz, 1H), 7.36 (m, 1H), 6.86-7.04 (m, 3H), 1.62 (s, 9H).

Step 2: (R)-2-Acetamido-3-((3-(tert-butoxycarbonyl)-2',4'-difluorobiphenyl-4-yloxy) carbonylthio) propanoic acid The compound was synthesized from tert-butyl 2',4'-difluoro-4-hydroxybiphenyl-3-carboxylate and NAC following the experimental procedure detailed in Method A. It was purified by flash chromatography on SiO$_2$ (3→15% MeOH/CH$_2$Cl$_2$) to furnish (R)-2-acetamido-3-((3-(tert-butoxycarbonyl)-2',4'-difluorobiphenyl-4-yloxy)carbonylthio)propanoic acid (off-white solid, yield: 60%).

$^1$H NMR (CD$_3$OD, 250 MHz) δ ppm: 7.96 (m, 1H), 7.72 (d, J=7.9 Hz, 1H), 7.54 (q, J=8.7 Hz, 1H), 7.29 (d, J=8.7 Hz, 1H), 7.09 (m, 2H), 4.61 (m, 1H), 3.64 (dd, J$_1$=14.3 Hz, J$_2$=4.7 Hz, 1H), 3.26 (m, 1H), 2.00 (s, 3H), 1.59 (s, 9H).

Example 15

(R)-Benzyl 4-((2-acetamido-3-methoxy-3-oxopropylthio)carbonyloxy)-2',4'-difluorobiphenyl-3-carboxylate

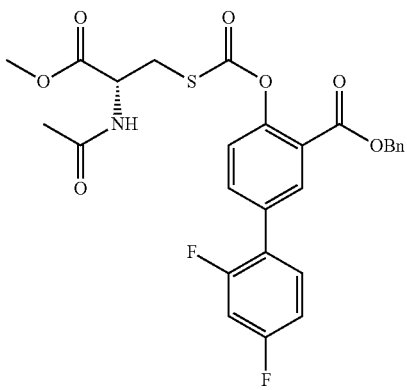 [SMILES: COC(=O)[C@H](CSC(=O)Oc1ccc(-c2ccc(F)cc2F)cc1C(=O)OCc1ccccc1)NC(C)=O]

H$_2$SO$_4$ (0.020 mL, 0.343 mmol) was added to a solution of (R)-2-acetamido-3-((2',4'-difluoro-3-(benzyloxycarbonyl)biphenyl-4-yloxy)carbonylthio)propanoic acid (54 mg, 0.102 mmol) in MeOH (10 mL). The reaction mixture was stirred at r.t. for 18 h, poured into H$_2$O (30 mL) and extracted with CH$_2$Cl$_2$ (20 mL). The organic layer was dried over Na$_2$SO$_4$ (anhydrous), filtered and concentrated. The crude residue was purified by flash chromatography on SiO$_2$ (3% MeOH/CH$_2$Cl$_2$) to furnish (R)-benzyl 4-((2-acetamido-3-methoxy-3-oxopropylthio)carbonyloxy)-2',4'-difluorobiphenyl-3-carboxylate (yellow-coloured solid, yield: 82%).

$^1$H NMR (CD$_3$OD, 250 MHz) δ ppm: 8.19 (s, 1H), 7.75 (d, J=8.4 Hz, 1H), 7.50-7.37 (m, 5H), 7.30 (m, 1H), 7.03 (d, J=8.4 Hz, 1H), 6.95 (d, J=8.4 Hz, 1H), 6.58 (d, J=7.2 Hz, 1H), 5.41 (s, 2H), 4.96 (m, 1H), 3.80 (s, 3H), 3.51 (dd, J$_1$=14.4 Hz, J$_2$=4.5 Hz, 1H), 3.38 (dd, J$_1$=14.4 Hz, J$_2$=5.2 Hz, 1H), 2.01 (s, 3H).

EI MS: m/z=544 (M+1).

Example 16

(R)-tert-Butyl 4-((2-acetamido-3-methoxy-3-oxopropylthio)carbonyloxy)-2',4'-difluorobiphenyl-3-carboxylate

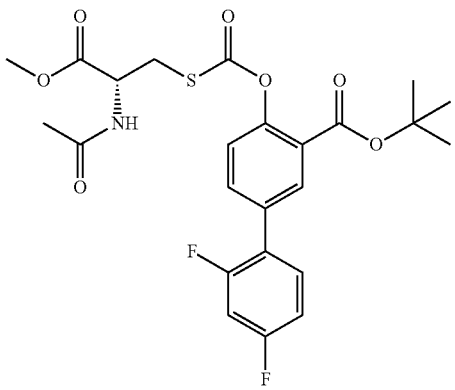 [SMILES: COC(=O)[C@H](CSC(=O)Oc1ccc(-c2ccc(F)cc2F)cc1C(=O)OC(C)(C)C)NC(C)=O]

H$_2$SO$_4$ (0.020 mL, 0.343 mmol) was added to a solution of (R)-2-acetamido-3-(3-(tert-butoxycarbonyl)-2',4'-difluorobiphenyl-4-yloxy)carbonylthio)propanoic acid (170 mg, 0.343 mmol) in MeOH (5 mL). The reaction mixture was stirred at r.t. for 16 h, poured into H$_2$O (50 mL) and extracted with CH$_2$Cl$_2$ (50 mL). The organic layer was dried over Na$_2$SO$_4$ (anhydrous), filtered and concentrated. The crude residue was purified by flash chromatography on SiO$_2$ (3% MeOH/CH$_2$Cl$_2$) to furnish (R)-tert-butyl 4-((2-acetamido-3-methoxy-3-oxopropylthio)carbonyloxy)-2',4'-difluorobiphenyl-3-carboxylate (yellow-coloured solid, yield: 53%).

$^1$H NMR (CD$_3$OD, 250 MHz) δ ppm: 7.99 (s, 1H), 7.65 (m, 1H), 7.40 (m, 1H), 7.19 (m, 1H), 6.89-7.02 (m, 2H), 4.95 (m, 1H), 3.77 (s, 3H), 3.42 (dd, J$_1$=14.4 Hz, J$_2$=4.6 Hz, 1H), 3.27 (dd, J$_1$=14.4 Hz, J$_2$=5.2 Hz, 1H), 2.02 (s, 3H), 1.59 (s, 9H).

EI MS: m/z=510 (M+1).

Example 17

(R)-2-Acetamido-3-((2',4'-difluoro-3-((4-methoxybenzyloxy)carbonyl) biphenyl-4-yloxy)carbonylthio)propanoic acid

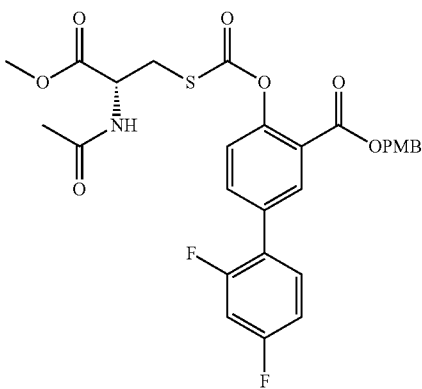

Step 1: 4-Methoxybenzyl 2',4'-difluoro-4-hydroxybiphenyl-3-carboxylate

PMBBr (1.20 mL, 8.325 mmol) was added to a solution of diflunisal (1.50 g, 5.995 mmol) in TBAF (7 mL, 1 M solution in THF) and the mixture was stirred at r.t. overnight (16 h). The reaction mixture was poured into H$_2$O (100 mL) and extracted with EtOAc (70 mL). It was dried over Na$_2$SO$_4$ (anhydrous), filtered and concentrated. The crude residue was flash chromatographed on SiO$_2$ (5→10% EtOAc/hexanes) to furnish 1.85 g of 4-methoxybenzyl 2',4'-difluoro-4-hydroxybiphenyl-3-carboxylate (white solid, yield: 83%).

$^1$H NMR (CDCl$_3$, 250 MHz) δ ppm: 10.89 (s, 1H), 7.96 (bs, 1H), 7.58 (dt, J$_1$=8.6 Hz, J$_2$=1.9 Hz, 1H), 7.39 (d, J=8.9 Hz, 2H), 7.33 (m, 1H), 7.05 (d, J=8.6 Hz, 1H) 6.98-6.83 (m, 4H), 5.34 (s, 2H), 3.81 (s, 3H).

Step 2: (R)-2-Acetamido-3-((2',4'-difluoro-3-((4-methoxybenzyloxy)carbonyl)biphenyl-4-yloxy)carbonylthio)propanoic acid The compound was synthesized from 4-methoxybenzyl 2',4'-difluoro-4-hydroxybiphenyl-3-carboxylate and NAC following the experimental procedure detailed in Method A. It was purified by flash chromatography on SiO$_2$ (0→20% MeOH/CH$_2$Cl$_2$) to furnish (R)-2-acetamido-3-((2',4'-difluoro-3-((4-methoxybenzyloxy)carbonyl)biphenyl-4-yloxy) carbonylthio)propanoic acid (off-white solid, yield: 18%).

The compound was submitted to next step without characterization.

Step 3: (R)-4-Methoxybenzyl 4-((2-acetamido-3-methoxy-3-oxopropylthio)carbonyloxy)-2',4'-difluorobiphenyl-3-carboxylate H$_2$SO$_4$ (0.04 mL, 0.750 mmol) was added to a solution of (R)-2-acetamido-3-((2',4'-difluoro-3-((4-methoxybenzyloxy)carbonyl)biphenyl-4-yloxy)carbonylthio)propanoic acid (160 mg, 0.286 mmol) in MeOH (25 mL). The reaction mixture was stirred at r.t. for 2 days, poured into H$_2$O (100 mL) and extracted with CH$_2$Cl$_2$ (100 mL). The organic layer was dried over Na$_2$SO$_4$ (anhydrous), filtered and concentrated. The crude residue was purified by flash chromatography on SiO$_2$ (5→80% EtOAc/hexanes) to furnish (R)-4-methoxybenzyl 4-((2-acetamido-3-methoxy-3-oxopropylthio)carbonyloxy)-2',4'-difluorobiphenyl-3-carboxylate (white solid, yield: 30%).

$^1$H NMR (CDCl$_3$, 250 MHz) δ ppm: 8.10 (bs, 1H), 7.68 (dt, J$_1$=8.5 Hz, J$_2$=1.6 Hz 1H), 7.37 (d, J=8.5 Hz, 2H), 7.33 (m, 1H), 7.22 (d, J=8.6 Hz, 1H) 7.01-6.85 (m, 4H), 6.56 (d, J=7.6 Hz, 1H), 5.30 (s, 2H), 4.92 (m, 1H), 3.81 (s, 3H), 3.77 (s, 3H), 3.48 (dd, J$_1$=14.5 Hz, J$_2$=4.7 Hz, 1H), 3.33 (dd, J$_1$=14.5 Hz, J$_2$=5.5 Hz, 1H), 1.99 (s, 3H).

EI MS: m/z=574 (M+1).

Example 18

2-(2-((2',4'-Difluoro-3-(methoxycarbonyl)biphenyl-4-yloxy)carbonylthio) propanamido)acetic acid

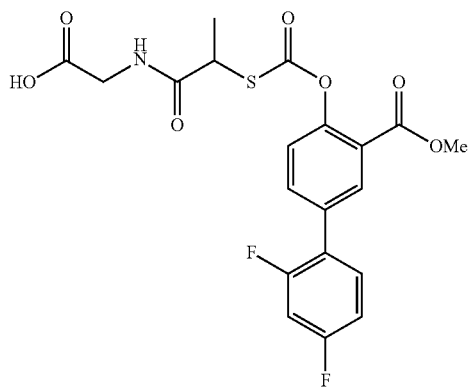 [SMILES: COC(=O)c1cc(-c2ccc(F)cc2F)ccc1OC(=O)SC(C)C(=O)NCC(=O)O]

The compound was synthesized from methyl 2',4'-difluoro-4-hydroxybiphenyl-3-carboxylate and N-(2-mercaptopropionyl)glycine following the experimental procedure detailed in Method A, avoiding the addition of Et$_3$N to the reaction medium. The crude residue was purified by flash chromatography on SiO$_2$ (2→10% MeOH/CH$_2$Cl$_2$) to give a colourless oil that was precipitated by stirring at −78° C. in the presence of hexanes, to furnish 2-(2-((2',4'-difluoro-3-(methoxycarbonyl)biphenyl-4-yloxy)carbonylthio)propanamido) acetic acid (white solid, yield: 19%).

$^1$H NMR (CD$_3$OD, 250 MHz) δ ppm: 8.11 (s, 1H), 7.78 (d, J=8.5 Hz, 1H), 7.55 (m, 1H), 7.34 (d, J=7.34 Hz, 1H), 7.05-7.14 (m, 2H), 4.24 (c, J=6.6 Hz, 1H), 3.85-3.99 (m, 5H), 1.61 (d, J=6.6 Hz, 3H).

EI MS: m/z=454 (M+1).

Example 19

(R)-2-Acetamido-3-(2-(benzyloxycarbonyl)-5-(trifluoromethyl)phenoxy) carbonylthio)propanoic acid

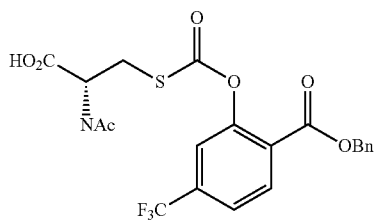

Step 1: Benzyl 2-hydroxy-4-(trifluoromethyl)benzoate

BnBr (1.20 mL, 8.325 mmol) was added to a solution of 2-hydroxy-4-(trifluoromethyl)benzoic acid (1.50 g, 7.277 mmol) in TBAF (10 mL, 1 M solution in THF) and the mixture was stirred at r.t. for 2 h. The reaction mixture was poured into NaHCO$_3$ (saturated aqueous solution, 100 mL) and extracted with EtOAc (100 mL). It was dried over Na$_2$SO$_4$ (anhydrous), filtered and concentrated. The crude residue was flash chromatographed on SiO$_2$ (5→30% EtOAc/hexanes) to furnish 2.18 g of benzyl 2-hydroxy-4-(trifluoromethyl)benzoate (colourless oil, yield: quantitative).

$^1$H NMR (CDCl$_3$, 250 MHz) δ ppm: 10.89 (s, 1H), 7.99 (d, J=8.5 Hz, 1H), 7.44 (m, 6H), 7.10 (d, J=8.5 Hz, 1H), 5.42 (s, 2H).

Step 2: (R)-2-Acetamido-3-((2-(benzyloxycarbonyl)-5-(trifluoromethyl)phenoxy) carbonylthio)propanoic acid The compound was synthesized from benzyl 2-hydroxy-4-(trifluoromethyl)benzoate and NAC following the experimental procedure detailed in Method A. The crude residue was purified by flash chromatography on SiO$_2$ (5→20% MeOH/CH$_2$Cl$_2$) to give (R)-2-acetamido-3-(2-(benzyloxycarbonyl)-5-(trifluoromethyl)phenoxy)carbonylthio)propanoic acid (white solid, yield: 18%).

$^1$H NMR (CD$_3$OD, 250 MHz) δ ppm: 8.17 (d, J=8.2 Hz, 1H), 7.72 (d, J=8.2 Hz, 1H), 7.61 (s, 1H), 7.33-7.48 (m, 5H), 5.36 (s, 2H), 4.54 (m, 1H), 3.54 (dd, J$_1$=4.1 Hz, J$_2$=13.7 Hz, 1H), 3.18 (m, 1H), 1.96 (s, 3H).

EI MS: m/z=486 (M+1).

Biological Data

The following biological data show the ability of the claimed compounds to be hydrolyzed under various biological conditions and release an anti-inflammatory and an antioxidant compound.

Example 20

Plasma Stability Studies

Table 1 and 2 summarize in vitro data showing that thiocarbonate compounds are hydrolyzed in the presence of human liver S9 fraction and release the NSAID component, Diflunisal (Table 1) or salicylate (Table 2). Most of the compounds release the NSAID when incubated in the presence of human liver S9 fraction, but some of them do not cleave properly: no diflunisal or salicylate has been detected after 1 h of incubation of a compound as described in Example 2 or a compound as described in Example 4 in the presence of S9 fraction.

TABLE 1

Detection of Diflunisal after 60 min of incubation of 2 μM of indicated compounds in the presence of human liver S9 fraction.

| Compound | % of Diflunisal (relative to total detected metabolites population) after incubation with human liver S9 fraction |
|---|---|
| Example 1 | 84.9% |
| Example 3 | >10% |
| Example 5 | 79.2% |
| Example 7 | 92.9% |
| Example 8 | 81.5% |
| Example 9 | 51.9% |
| Example 15 | 50.9% |
| Example 16 | 6.6% |

TABLE 2

Detection of Salicylate after 60 min of incubation of 2 μM of indicated compound in the presence of human liver S9 fraction.

| Compound | % of Salicylate (relative to total detected metabolites population) after incubation with human liver S9 fraction |
|---|---|
| Example 2 | 0% |
| Example 4 | 0% |
| Example 6 | 66.30% |
| Example 10 | 61.10% |
| Example 11 | 35.70% |
| Example 12 | 27.20% |

Example 21

Diflunisal Levels

Diflunisal is detected in plasma of mice orally dosed with the compound described in Example 5 or the compound described in Example 8 (0.05 mmol/kg) (table 3).

TABLE 3

Diflunisal levels in plasma 1 h and 2 h after oral administration of indicated compounds in mice (n = 3)

|  | Diflunisal, ng/mL | |
|---|---|---|
|  | 1 h | 2 h |
| Example 5 | 258 +/− 12 | 454 +/− 39 |
| Example 8 | 301 +/− 49 | 300 +/− 57 |

Example 22

Daily Glycemia and Body Weight; Fluid and Food Intake

Figure 2:
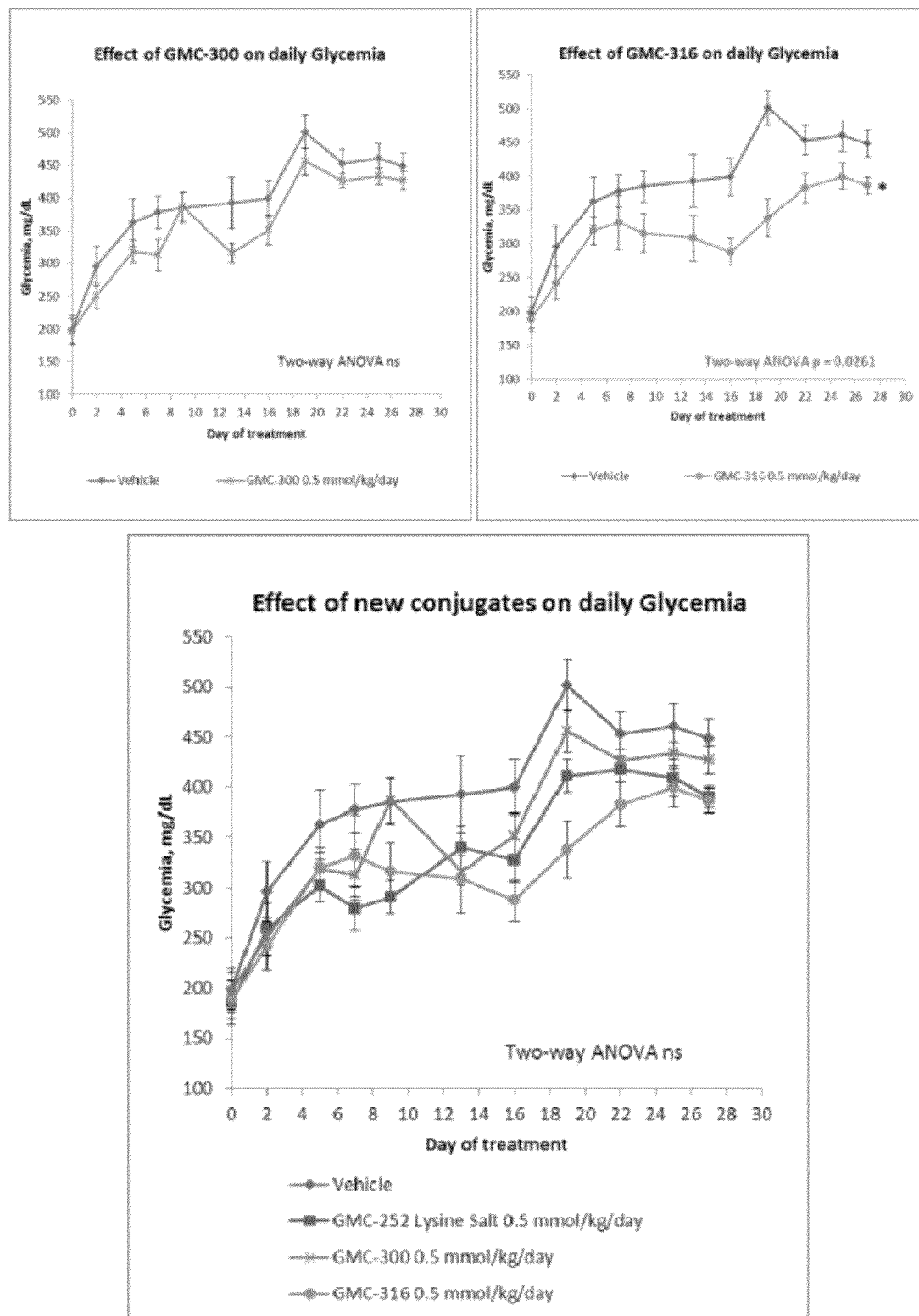
FIG. 2 shows the glycemia levels after treatment with the compounds according to certain embodiments of the invention identified in the figure legend in db/db mice.
Figure 3:
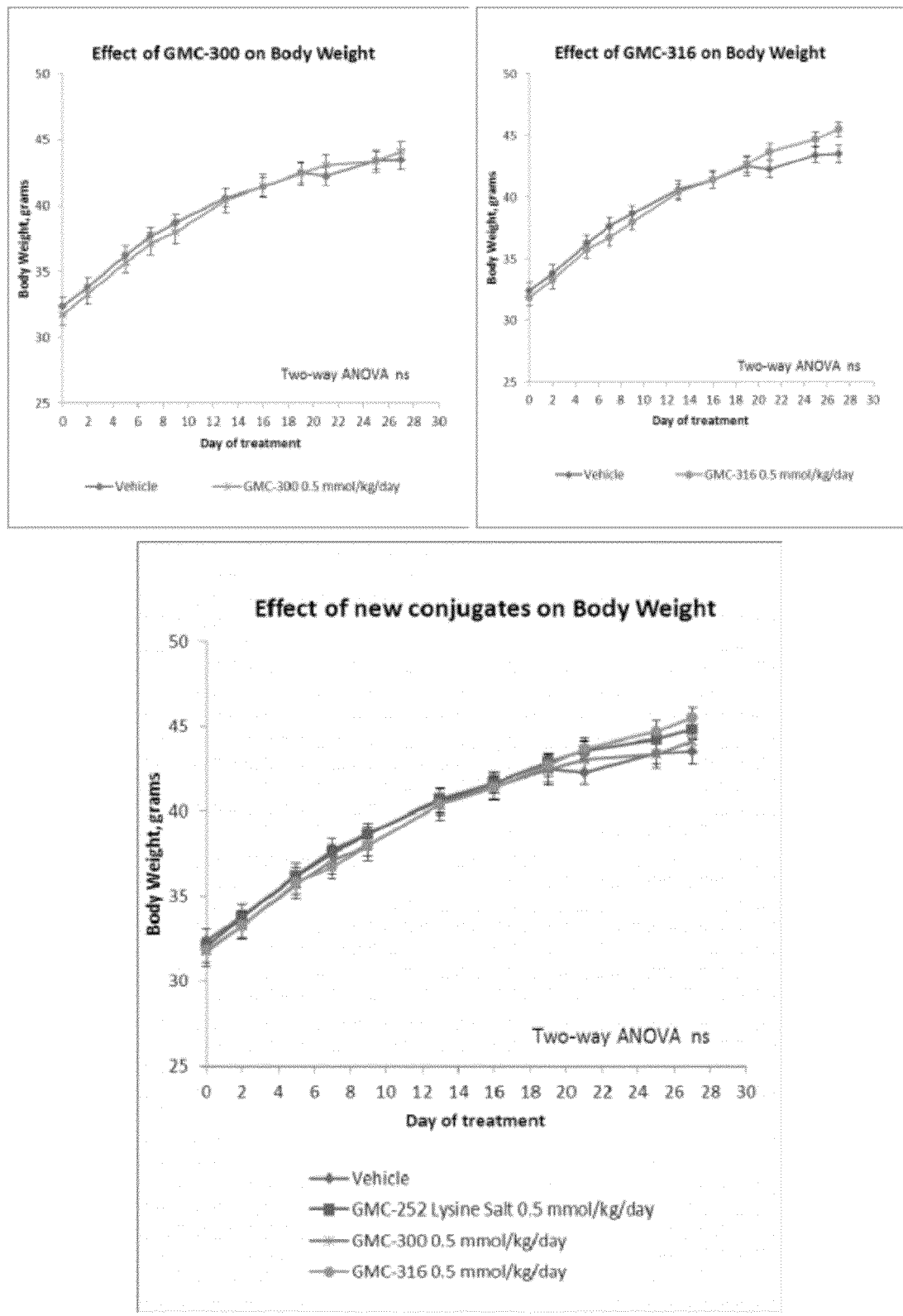
FIG. 3 shows the effect on body weight after treatment with the compounds according to certain embodiments of the invention identified in the figure legend in db/db mice.
Figure 4:
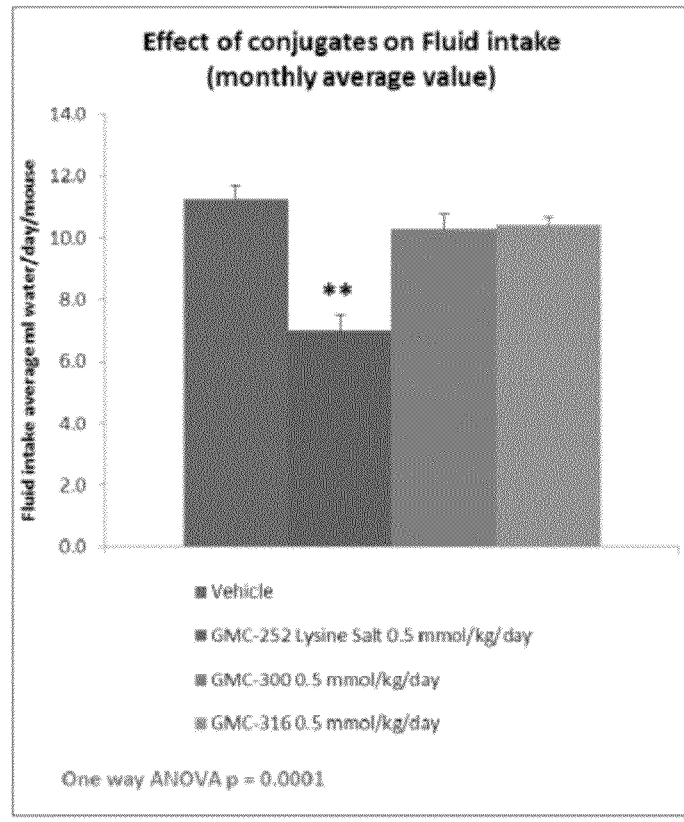
FIG. 4 illustrated the fluid and food intake of db/db mice after treatment with the compounds according to certain embodiments of the invention identified in the figure legend.
Figure 4:
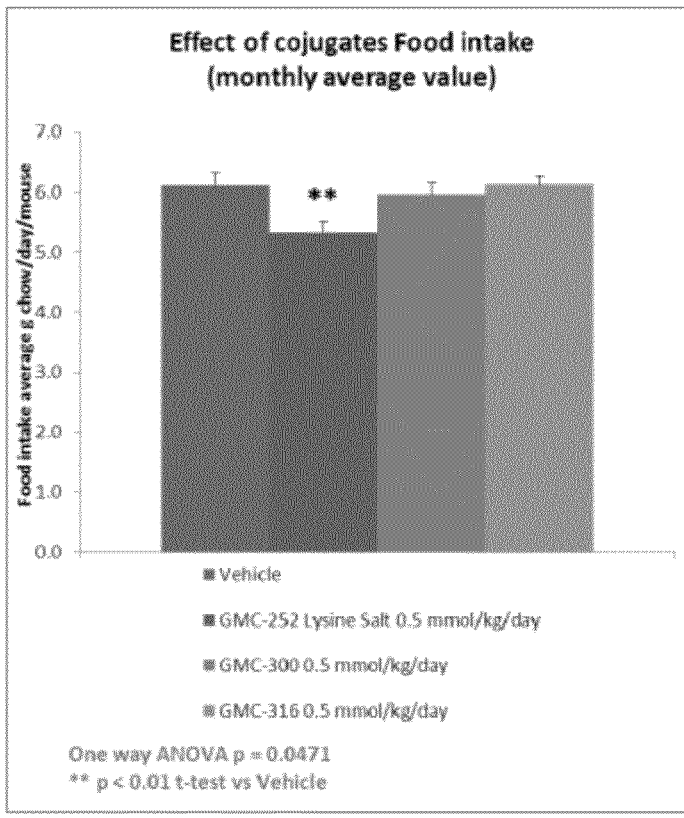

Daily glycemia levels and effect on body weight is evaluated in mice orally dosed with the compound described in Example 5 (GMC-300) and the compound described in Example 8 (GMC-316). Compound GMC-252, which has the following structure:

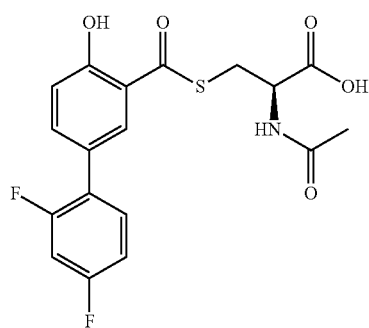 [SMILES: CC(=O)N[C@@H](CSC(=O)c1cc(-c2ccc(F)cc2F)ccc1O)C(=O)O]

is disclosed in WO/2010/106082 (Example 13, (R)-2-acetamido-3-(2',4'-difluoro-4-hydroxybiphenylcarbonylthio)propanoic acid), and was used as a positive control. The results on glycemia levels are disclosed in FIG. 2, and the results on body weight are disclosed in FIG. 3. The effect of these compounds on fluid and food intake is shown in FIG. 4.

Example 23

Pancreas Weight and White Adipose Tissue (WAT) Weight

Figure 5:
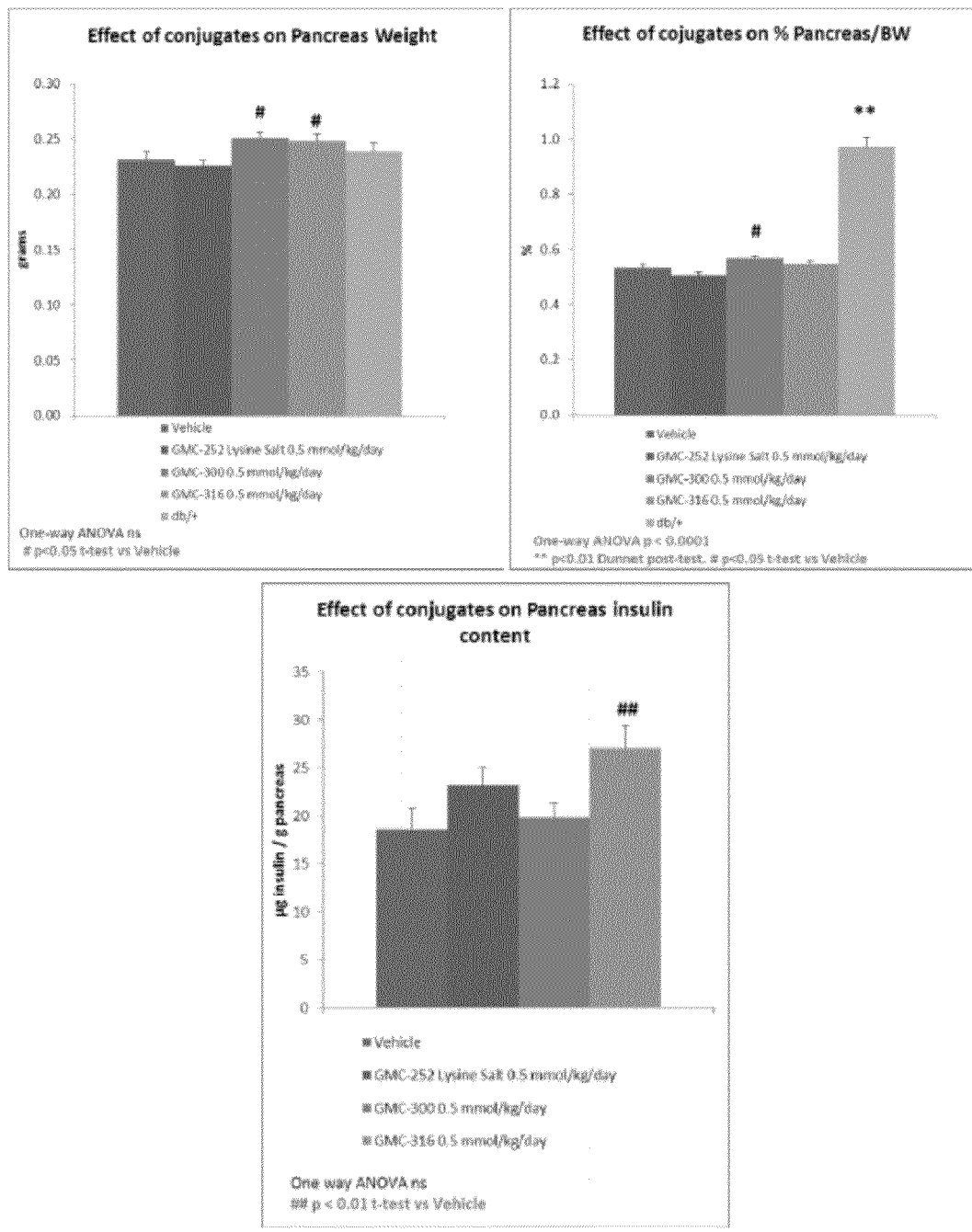
FIG. 5 shows the effect on the pancreas weight in db/db mice after treatment with the compounds according to certain embodiments of the invention identified in the figure legend. Also shown is the pancreas weight as a percentage of body weight, and the pancreas insulin level after treatment with the compounds of the invention identified in the figure legend.
Figure 6:
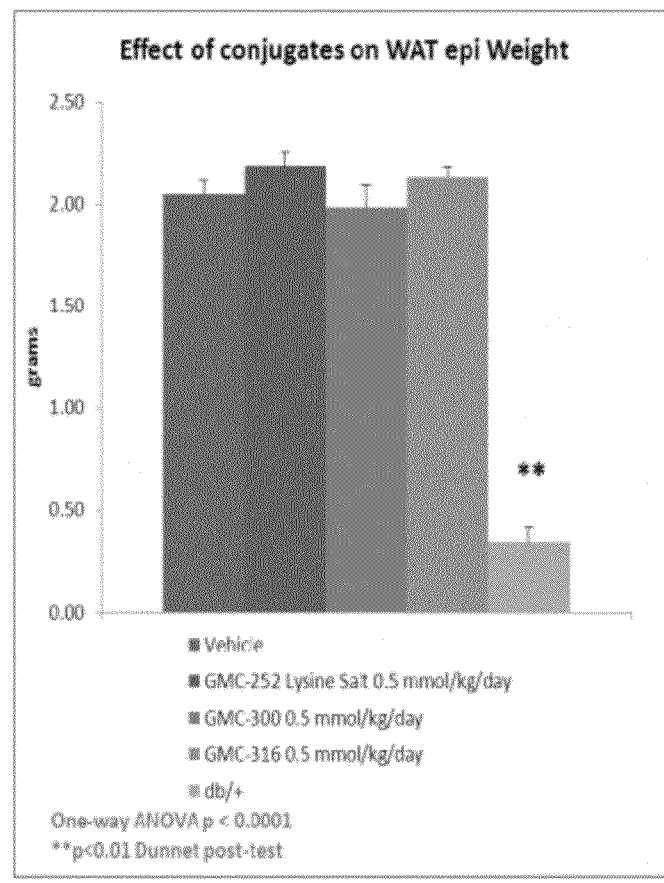
FIG. 6 shows the effect on the epididymal (epi) white adipose tissue (WAT) weight in db/db mice after treatment with the compounds according to certain embodiments of the invention identified in the figure legend. Also shown is epi WAT weight as a percentage of body weight.
Figure 6:
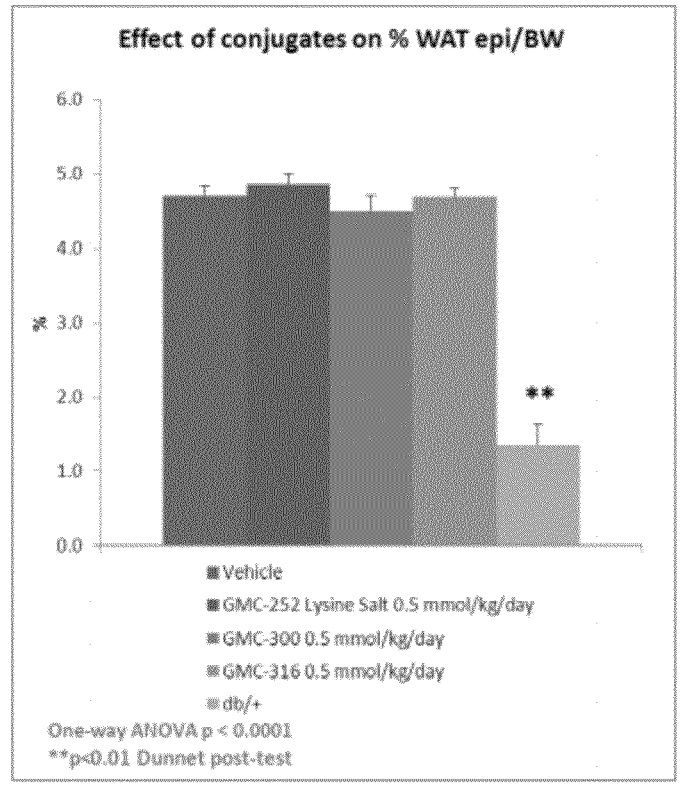

The weight of pancreas and white adipose tissue (WAT) were evaluated in in mice orally dosed with the compound described in Example 5 (GMC-300) and the compound described in Example 8 (GMC-316). The effect on the pancreas weight (also pancreas weight as a percentage of body weight) is disclosed in FIG. 5; the effect on the epididymal (epi) white adipose tissue (WAT) weight is disclosed in FIG. 6.

Example 24

Insulin Tolerance and Glucose Tolerance

Figure 7:
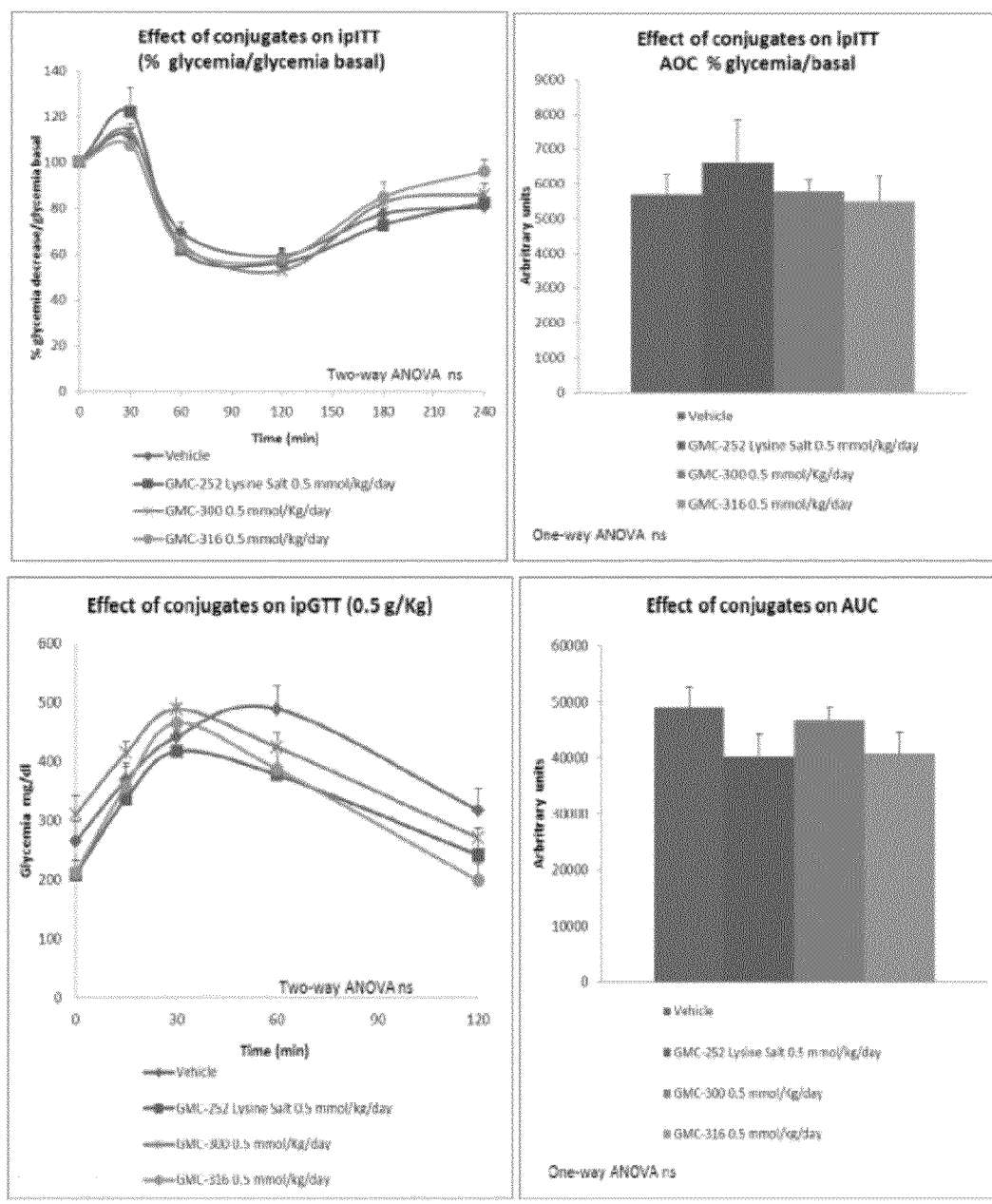
FIG. 7 illustrates the effect on intraperitoneal insulin tolerance (ipITT) and intraperitoneal glucose tolerance (ipGTT) in db/db mice after treatment with the compounds according to certain embodiments of the invention identified in the figure legend.

The compound described in Example 5 (GMC-300) and the compound described in Example 8 (GMC-316) were evaluated orally in mice for intraperitoneal insulin tolerance (ipITT) and intraperitoneal glucose tolerance (ipGTT) (FIG. 7)

Example 25

Glycemia and Insulinemia

Figure 9:
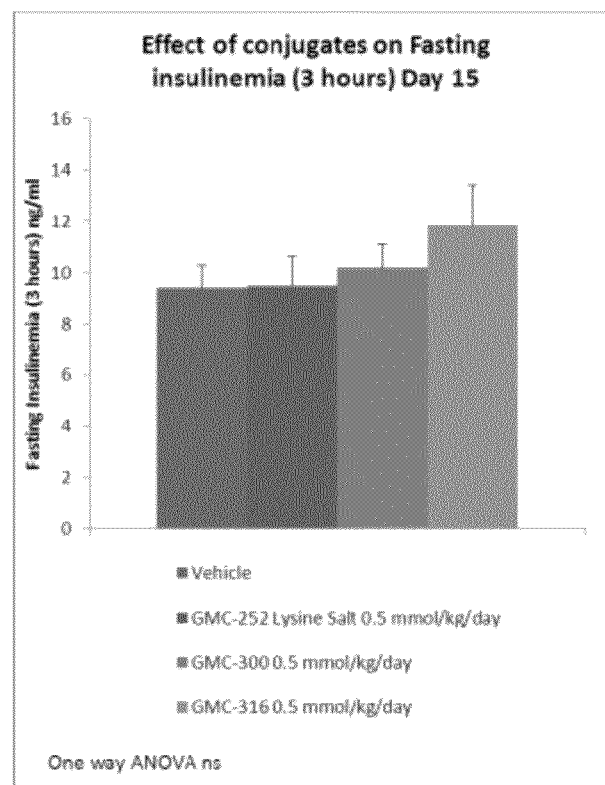
FIG. 9 shows the fasting insulinemia levels in db/db mice at day 15, and 23 after treatment with the compounds according to certain embodiments of the invention identified in the figure legend.
Figure 9:
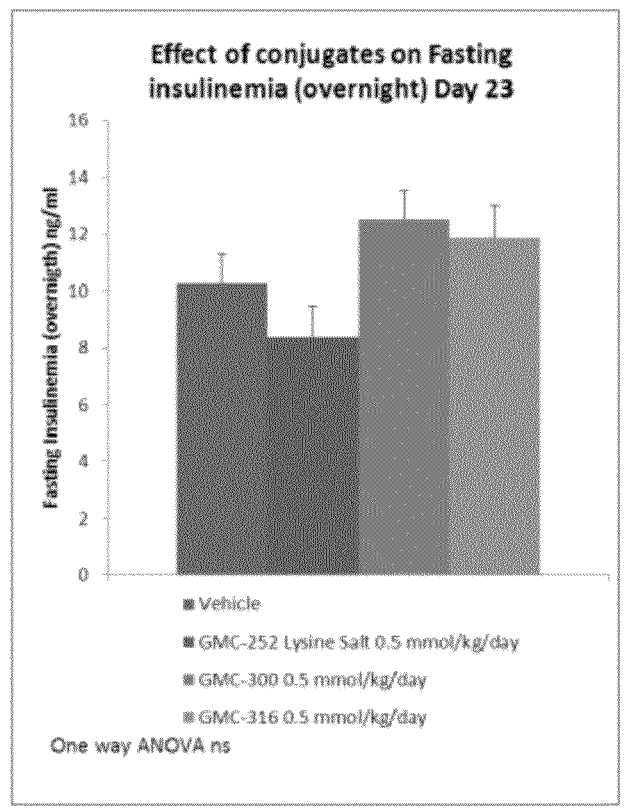
Figure 10:
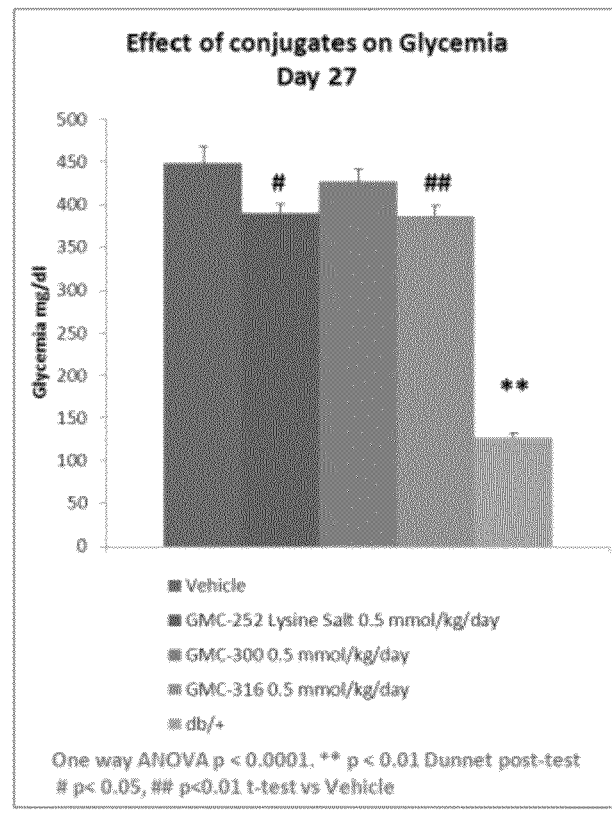
FIG. 10 illustrates the total glycemia and total insulinemia in db/db mice at day 27 after treatment with the compounds according to certain embodiments of the invention identified in the figure legend.
Figure 10:
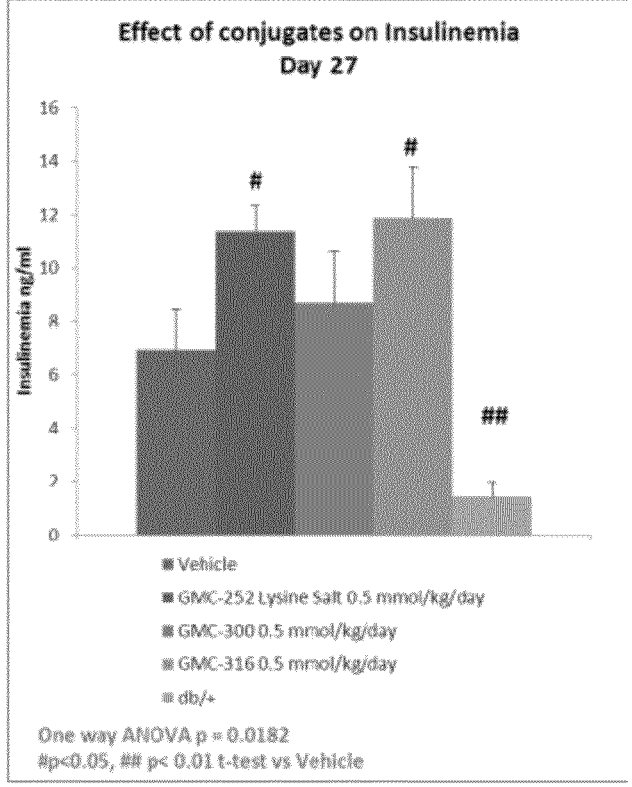

The compound described in Example 5 (GMC-300) and the compound described in Example 8 (GMC-316) were evaluated orally in mice for the fasting glycemia at day 15, 20 and 23 (FIG. 8), fasting insulinemia at day 15 and 23 (FIG. 9), and total glycemia and insulinemia at day 27 (FIG. 10).

Example 26

Various Markers in Plasma

Figure 11:
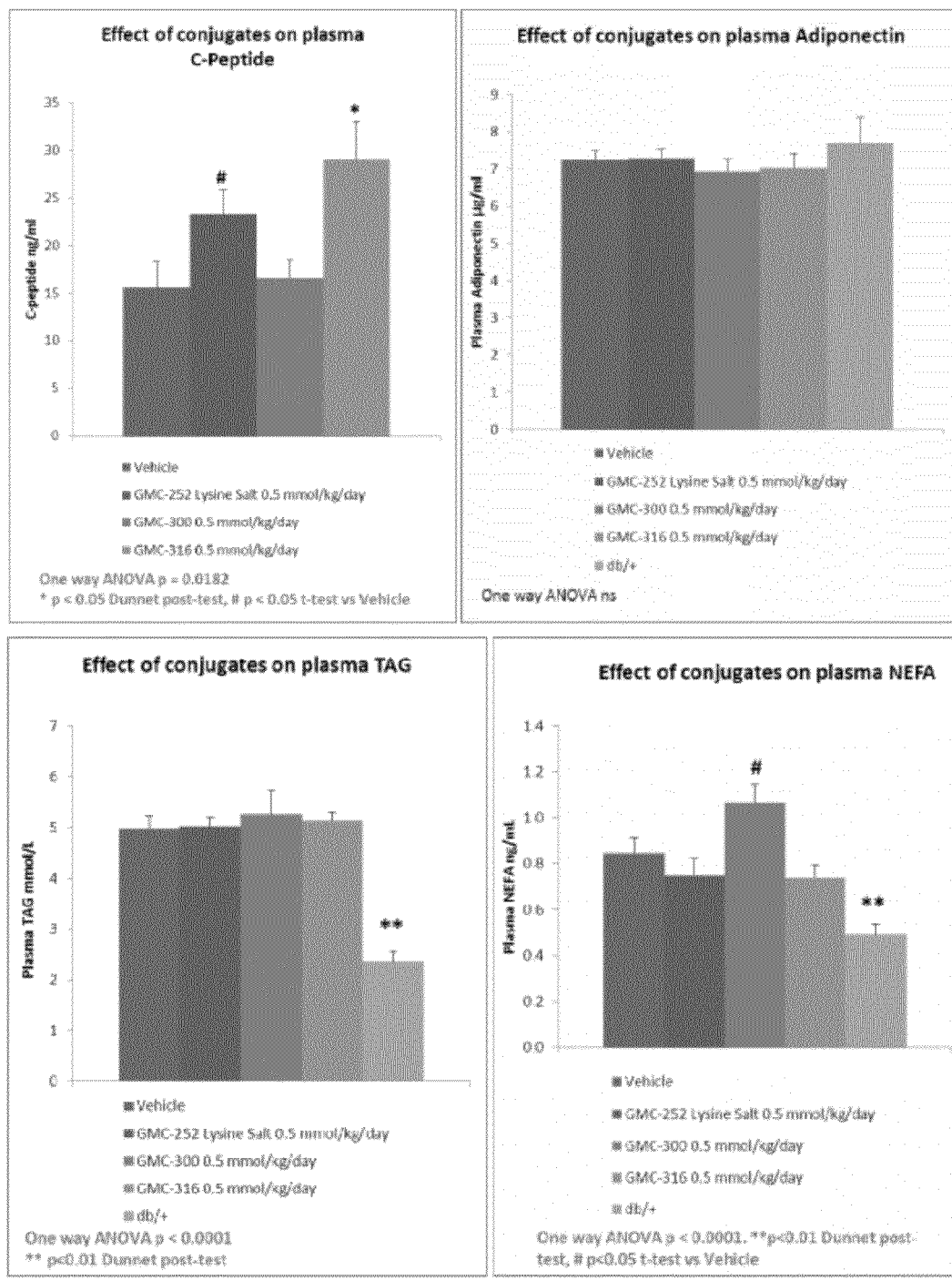
FIG. 11 shows the level of plasma C-peptide, plasma Adiponectin, plasma triacylglycerol (plasma TAG), and plasma non-esterified fatty acids (plasma NEFA) in db/db mice after treatment with the compounds according to certain embodiments of the invention identified in the figure legend.
Figure 12:
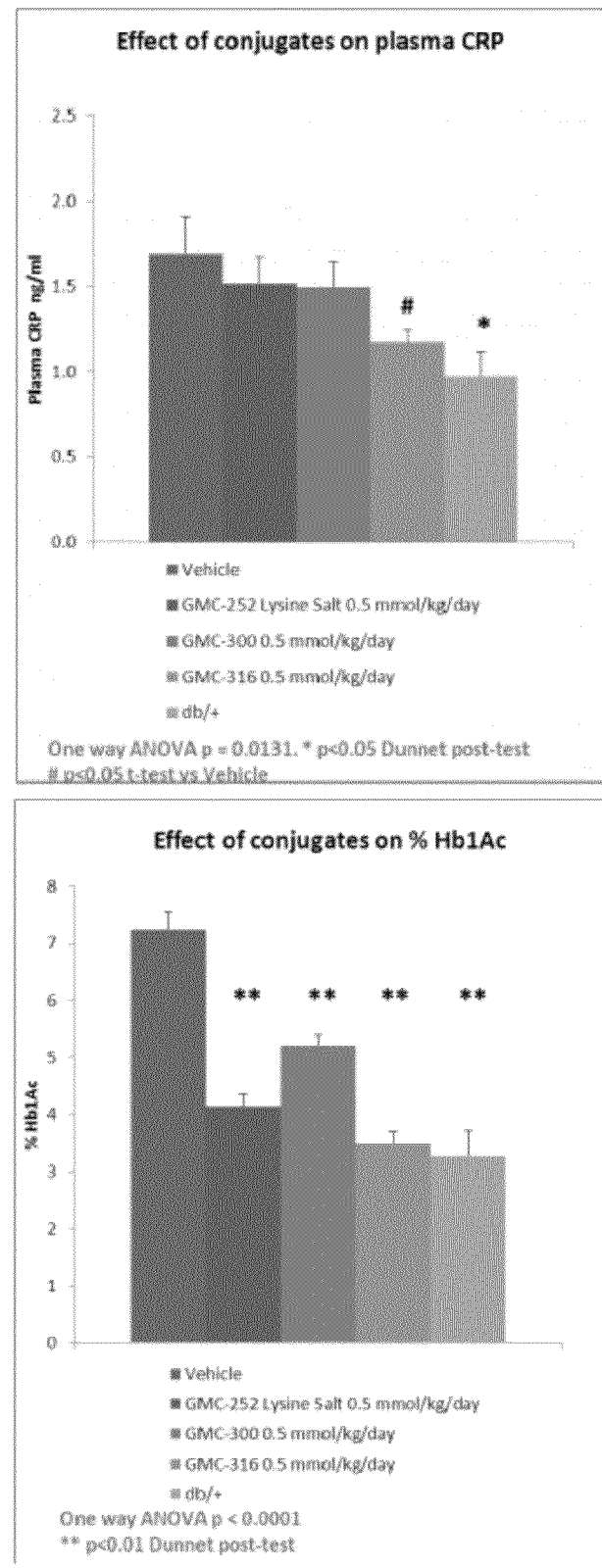
FIG. 12 shows the level of plasma C-Reactive Protein (plasma CRP) and percent of Hb1Ac in db/db mice after treatment with the compounds according to certain embodiments of the invention identified in the figure legend.

The compound described in Example 5 (GMC-300) and the compound described in Example 8 (GMC-316) were evaluated for various markers in plasma. FIG. 11 illustrates the level of plasma C-peptide, plasma Adiponectin, plasma triacylglycerol (plasma TAG), and plasma non-esterified fatty acids (plasma NEFA) in treated mice. FIG. 12 illustrates the level of plasma C-Reactive Protein (plasma CRP) and percent of Hb1Ac in treated mice.

Example 27

Plasma Cholesterol Levels

Figure 13:
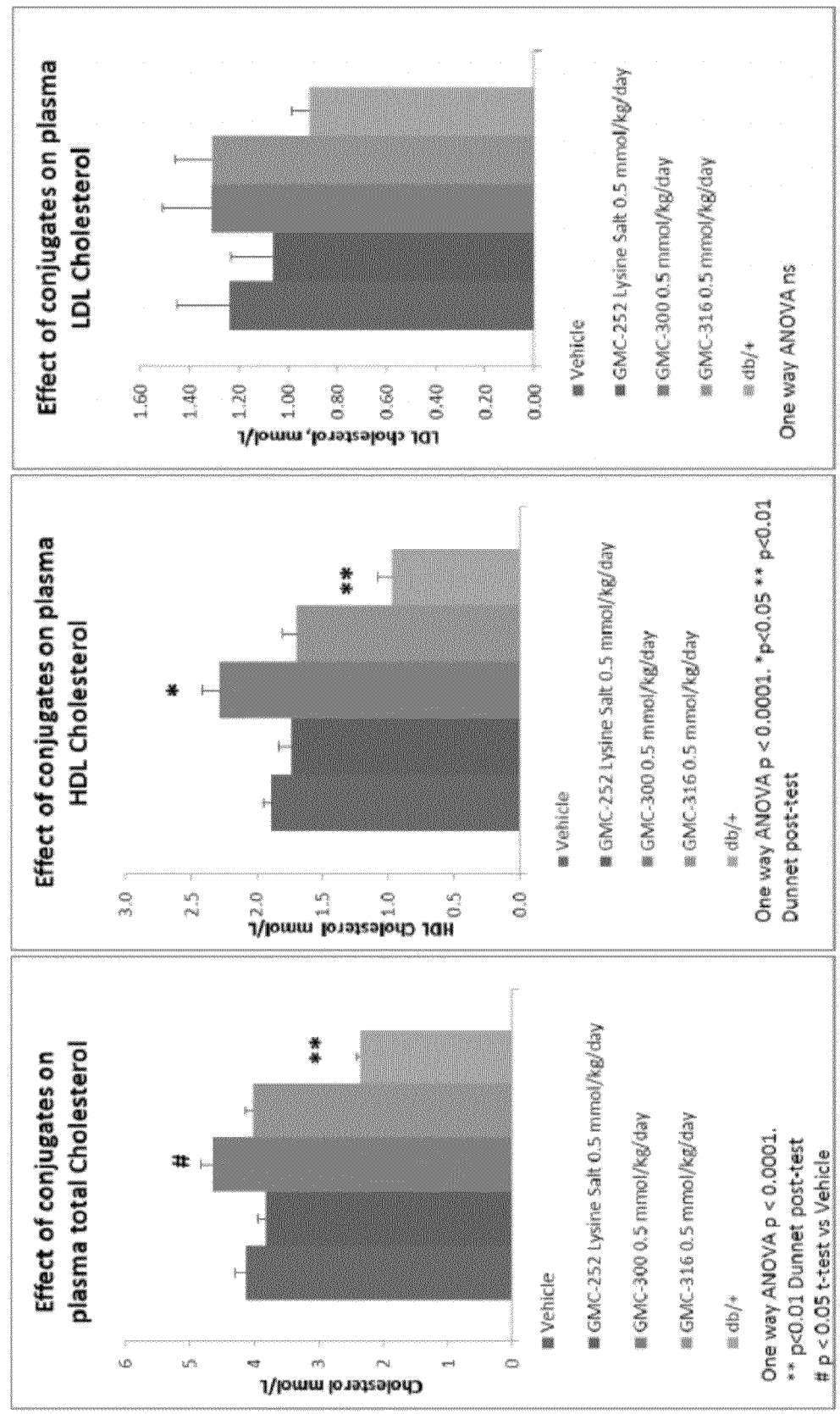
FIG. 13 shows the plasma cholesterol levels (total, HDL, and LDL) in db/db mice after treatment with the compounds according to certain embodiments of the invention identified in the figure legend.

The compound described in Example 5 (GMC-300) and the compound described in Example 8 (GMC-316) were evaluated for plasma cholesterol. FIG. 13 illustrates the level of total cholesterol, HLD cholesterol and LDL cholesterol in treated mice.

Methods

Pharmacokinetic Studies:

Male cd-1 mice weighing 25-30 g are purchased from Charles River Laboratories Spain. The animals are housed in animal quarters at 22° C. with a 12-h light/12-h dark cycle and fed ad libitum. O/N fasted animals are dosed at 9:00 pm with 0.05 mmol/kg of the indicated compound. Mice are sacrificed at the indicated time points, with $CO_2$ euthanasia, and blood is extracted from the inferior cava vein, using heparin as an anticoagulant, and maintained at 4° C. until the preparation of plasma. Plasma was separated after centrifugation of blood and kept at −20° C. until metabolites determination.

In Vitro Cleavage Studies:

The compounds are incubated with human liver S9 fraction to study its metabolic stability and to profile and identify the forming metabolites. The basic incubation mixture of 500 µl in volume consisted of the following components: 1.5 mg of protein per ml, substrate in DMSO, 1 mM NADPH, 1 mM UDPGA, 1 mM PAPS and 1 mM GSH. The substrate concentration used was 2 µM. The final amount of DMSO in the incubation was 1% (v/v). Each reaction mixture was preincubated for 2 minutes at +37° C. The reaction was started by addition of cofactors. After an incubation of 60 min, a 100 µl sample was collected and the reaction was terminated by adding an equal volume of ice-cold acetonitrile. Samples were subsequently cooled in an ice bath for 15 minutes and analyzed. The incubation samples were thawed at room temperature (RT), shaken and centrifuged for 10 min at 16100×g and pipetted to Maximum Recovery vials (Waters Corporation, Milford, Mass., USA). The samples are analyzed by HPLC/TOF-MS to monitor both the disappearance of the parent compound and formation of metabolites. The analytical method is optimised by using the parent compounds for fit-for-purpose chromatographic properties (peak shape and retention) and mass spectrometric ionisation. In addition to ion source conditions optimised to produce molecular ions with high abundance, the samples from last time point (60 min) are analysed also using another parameters (higher aperture voltage) to generate high-resolution in-source fragment ion data.

Parent disappearance is estimated based on relative LC/MS peak areas. The metabolites are mined from the data acquired from the 60 min point samples and the detected metabolites (biotransformations) are tentatively identified according to the accurate MS-data obtained. For the main metabolites also the in-source fragment ion data is used for elucidating the biotransformation sites.

Chemicals.

The chemicals were purchase from Sigma (Sigma Aldrich, St. Louis, Mo., USA) and PBS was purchase from Invitrogen. All the compounds were dissolved in PBS, with lysine salt when indicated, and the pH of the compounds without lysine was adjusted with NaOH 6N until pH 7.

Chronic Treatment in db/db Mice, ob/ob Mice and Zucker Diabetic Rats 5-weeks old male mice C57BL/Ks bearing the db/db mutation (The Jackson Laboratories) and 7-weeks old male mice C57BL/6 bearing the ob/ob mutation are purchased from Charles River Laboratories Spain (Sant Cugat del Vallès, Spain) are treated with compounds as disclosed herein for a month, administered by single oral injection. Glycemia levels are determined in blood from the Tail Vein, using a rapid glucose analyzer (Accu-Chek Aviva; Roche) 3 times per week, as well as body weight measure. The food and water intake is measured twice a week. At the end of the treatment, the mice are sacrificed, in feeding state, with $CO_2$ euthanasia, and the blood extracted from the Inferior Cave Vein, using heparin as an anticoagulant, and maintained at 4° C. until the preparation of plasma.

Intraperitoneal Insulin Tolerance Test (ipITT).

At the third week of treatment, an Insulin Tolerance Test (ITT) is performed as follows. Animals receive an ip injection of Insulin 2 UI/kg (Humulin®) and glycemia levels are determined at time zero (before the injection of insulin) and at different time points thereafter in blood from the Tail Vein, after the Insulin injection using a rapid glucose analyzer (Accu-Chek Aviva; Roche). FIG. 7 shows the insulin tolerance of the subject animals.

Intraperitoneal Glucose Tolerance Test (ipGTT)

At the fourth week of treatment, a Glucose Tolerance Test (GTT) is performed as follows. Overnight fasted animals receive an ip injection of Glucose 0.5 g/kg (Glucosmon 50®). Glycemic levels are determined, at time zero (before the injection of glucose) and at different time points thereafter, in blood from the Tail Vein using a rapid glucose analyzer (Accu-Chek Aviva; Roche). FIG. 7 shows the glucose tolerance of the subject animals.

Determination of Biochemical Parameters.

The circulating glucose concentration is determined by a rapid glucose analyzer (Accu-Chek Aviva; Roche). Plasma triglycerides and non esterified fatty acids are determined using conventional colorimetric methods (commercially available from Biosystems, Barcelona, Spain, and Wako Chemicals, Neuss, Germany, respectively). Plasma insulin concentration is determined by enzyme-linked immunosorbent assay method (CrystalChem, Downers Grove, Ill.).

Statistical Analysis.

Statistical comparisons between groups are established by two-way ANOVA using Prism 4 (GraphPad, San Diego, Calif.). A p value of less than 0.05 is considered to be statistically significant.

Figure 8:
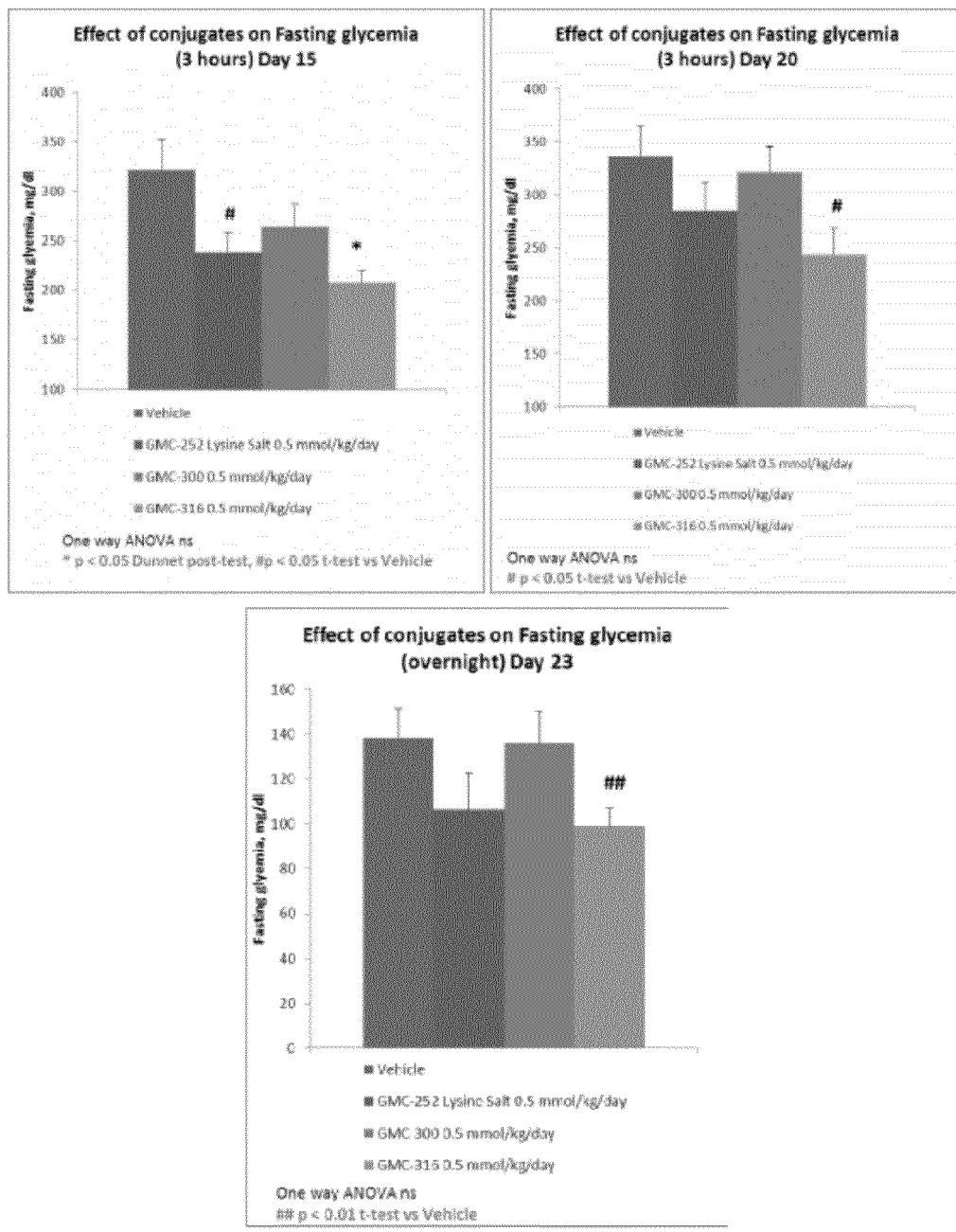
FIG. 8 shows the fasting glycemia levels in db/db mice at day 15, 20 and 23 after treatment with the compounds according to certain embodiments of the invention identified in the figure legend.

Reduction of Fasting Glycemia in db/db Mice db/db mice were treated for two weeks with a daily dose of the compound of Example 8, (R)-2-acetamido-3-((2',4'-difluoro-3-(propoxycarbonyl)biphenyl-4-yloxy)carbonylthio) propanoic acid, or with vehicle. FIG. 1 shows the fasting glycemia of the subject animals. Dosing with the compound of Example 8 significantly reduced the fasting glycemia of the animals. A t-test indicated that the value of p was less than 0.01. FIG. 8 shows the fasting glycemia of the subject animals for the compound of Example 5 and Example 8.

Protection of Beta-Cell Failure and Prevention of Hyperglycemia in Streptozotocin Treated Animals Diabetic mice or rats generated by streptozotocin administration exhibit an increase in levels of lipid peroxidation and a decrease in activity of antioxidant enzymes in the liver and kidneys as compared to control.

Conjugates of the invention administered orally and/or intraperitoneally (~250 mg/kg) prior to a single dose of streptozotocin (45 mg/kg i.p.) in rats followed by 4 additional treatment days can preserve beta-cells, reducing the development of hyperglycemia. The blood glucose level in pretreated animals is lower than the control group associated with a preserve capacity of beta-cell to secrete insulin measured in the blood.

Further, compounds of the invention are tested for their efficiency at preserving beta-cell function of mice challenged by one shot of streptozotocin (45 mg/kg i.p.). Oral or intraperitoneal administration of a conjugate of the invention, prior and during 5 days following streptozotocin exposure can protect beta-cells from oxidative stress and reduces the development of hyperglycemia over time compared to control.

Compounds of the invention can reduce levels of 8-hydroxy-deoxyguanosine (8OhdG) and malondialdehyde+4-hydroxy-2-nonenal (4HNE), markers for both oxidative stress and lipid peroxidation in the blood.

Type 1 Diabetic Model in Mice

Diabetic mice induced by streptozotocin injection (120 mg/kg i.p.) are treated for 4 weeks with 250 mg/kg/day (oral or i.p.) of a compound of the invention. At the end of the 4 week treatment, fasting glucose, fructosamine, triglycerides and cholesterol are measured. These biochemical parameters can be reduced in comparison to control group.

Further, oxidative stress and lipid peroxidation markers 8-hydroxy-deoxyguanosine (8OhdG), malondialdehyde and 4-hydroxy-2-nonenal (4HNE) are also reduced.

Still further, inflammatory cytokines, such as TNFalpha and IL-6, and glutathione (GSH) levels in the liver and the kidney can be reduced compared to non-treated animals.

In Vivo Beta Cell Protection Model

Beta-cell destruction is induced in cd-1 mice after 3 hours of fasting by a single intraperitoneal injection of a freshly prepared solution of alloxan 200 mg/kg (Sigma-Aldrich, San Luis, Mo.) that was dissolved in 0.9% NaCl. Compounds of the invention or vehicle control are administered intraperitoneally, 1 hour before alloxan administration. At the end of the treatment, at day 4, animals are killed and the plasma collected and kept at −20° C. until used. Conjugates of Formula (I, II and III) as disclosed herein can beneficially reduce plasma glucose levels in Alloxan-treated animals as compared to control animals.

Restoration of Insulin Sensibility in ob/ob and db/db Mice 5-8 week old ob/ob and db/db mice are treated for 3 to 4 weeks with a daily dose of 50 to 250 mg/kg of a compound of the invention by oral gavage or with drug mix with food or subcutaneously.

Glucose tolerance test (OGTT or IPTT) can detect reduction in glucose level elevation during the test compared to non-treated animals. The capacity of the beta-cells to secrete insulin can be improved in the group administered with a compound of the invention compared to control demonstrating the protective effects toward pancreatic beta-cells.

Further, compounds of the invention can improve insulin sensitivity as evidenced by a sustained and pronounced glucose lowering effect. Also, the compounds of the invention can provide reduction in oxidative stress and lipid peroxidation as determined by the level of associated biomarkers: 8-hydroxy-deoxyguanosine (8OhdG), malondialdehyde and 4-hydroxy-2-nonenal (4HNE). Finally, inflammatory cytokines, TNFα and IL-6, can be reduced while the levels of glutathione (GSH) in the liver and the kidney are restored.

Restoration of Insulin Sensitivity in Zucker Diabetic Fatty (ZDF) Rats

To assess whether conjugates comprising an antioxidant agent and an inflammatory agent would prevent glucose toxicity and progression of diabetes mellitus associated with beta-cell failure overtime, the capacity of conjugates of Formula (I, II and III) to alter development of disease in this Type 2 diabetic animal model is assessed.

Zucker diabetic rats from 6 to 12 weeks of age are treated daily with an oral dose of a compound of the invention. Blood levels of 8OhdG, malondialdehyde+4HNE, two markers of chronic oxidative stress and lipid peroxidation, can be reduced in comparison to control animals. Inflammatory cytokines, TNFalpha and IL6 can be blunted when measured at the end of the 6 week treatment. In comparison, placebo-treated or control animals can develop progressive obesity, hyperglycemia, abnormal glucose tolerance test, defective glucose insulin secretion as well decrease islet insulin content. Further, treatment with compounds of the invention can at least partially prevent worsening of hyperglycemia, improve results of the glucose tolerance test, and preserve insulin secretion from beta-cells. Fasting glucose, fructosamine, HblAc, triglycerides and cholesterol all can be reduced in comparison to the control group.

Conjugates of Formula (I, II and III) of the invention can have beneficial effects in Type 2 diabetic animal models as compared to control animals, including hypolipidemic and anti-diabetic effects as well as antioxidant properties in different animal models of diabetes useful in preventing the development of beta-cell failure and aggravation of the diabetic status leading to cardiovascular complications. Such effects support therapeutic utility of conjugates comprising an antioxidant agent and an anti-inflammatory agent such as the compounds of Formula I, II and III.

Moreover the additive and/or synergism effects of these conjugates allow for the decrease dosing of each independent active ingredient. These additive and/or synergistic effects reduce the liability of side effects associated with a salicylate agent, gastric bleeding, or an antioxidant, tinnitus, given to a patient alone.

We claim:

1. A compound of Formula (I)

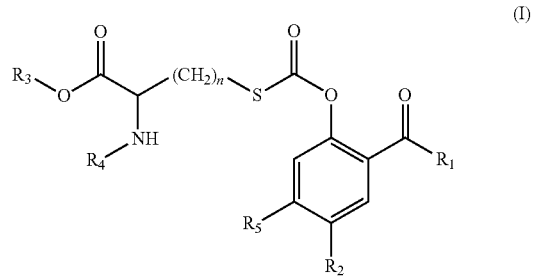

or a pharmaceutically acceptable salt thereof, wherein
n is 1 or 2;
$R_1$ is $OR_6$ or $NR_6R_7$;
$R_2$ is H or 2,4-difluorophenyl;
$R_3$ is H or $(C_1-C_6)$alkyl;
$R_4$ is H or acetyl;
$R_5$ is H or trifluoromethyl;
$R_6$ and $R_7$ are independently H, $(C_1-C_6)$alkyl, $(C_3-C_8)$cycloalkyl, or $(C_3-C_8)$cycloalkyl$(C_1-C_6)$alkyl, wherein the $(C_1-C_6)$alkyl, $(C_3-C_8)$cycloalkyl, and $(C_3-C_8)$cycloalkyl$(C_1-C_6)$alkyl are independently optionally substituted with 1, 2, 3, or 4 substituents that are independently $(C_1-C_6)$alkoxy, $(C_1-C_6)$alkoxy$(C_1-C_6)$alkyl, $(C_1-C_6)$alkoxycarbonyl, $(C_1-C_6)$alkylthio, halogen, hydroxy, hydroxycarbonyl, $NZ_1Z_2$, or phenyl, wherein the phenyl is optionally substituted with 1, 2, 3, 4, or 5 halogens and each $Z_1$ and $Z_2$ is independently H or $(C_1-C_6)$alkyl; or $R_6$ and $R_7$ together with the nitrogen atom to which they are attached form azetidine, pyrrolidine, piperidine, piperazine, N-methylpiperazine, morpholine, or azepane.

2. The compound of claim 1, wherein $R_6$ is H or $(C_1-C_6)$ alkyl.

3. The compound of claim 1, wherein $R_6$ is $(C_3-C_6)$ alkyl or optionally-substituted benzyl.

4. The compound of claim 1, wherein $R_1$ is methoxy, ethoxy or hydroxy.

5. The compound of claim 1, wherein $R_1$ is amino, methylamino, or dimethylamino.

6. The compound of claim 1, wherein $R_2$ is 2,4-difluorophenyl.

7. The compound of claim 1, wherein $R_3$ is hydrogen or methyl.

8. The compound of claim 1, wherein $R_4$ is acetyl.

9. The compound of claim 1, wherein $R_5$ is hydrogen.

10. A compound of Formula (III)

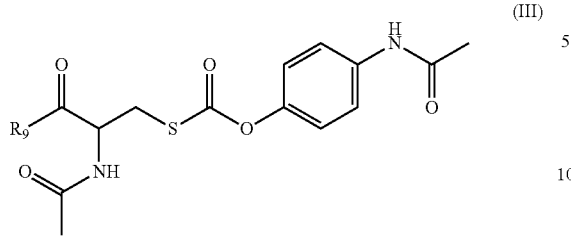

or a pharmaceutically acceptable salt thereof, wherein
$R_9$ is $OR_3$ or $NR_{10}R_{11}$;
$R_3$ is H, $(C_1-C_6)$alkyl, $(C_3-C_8)$cycloalkyl, or $(C_3-C_8)$cycloalkyl$(C_1-C_6)$alkyl, wherein the $(C_1-C_6)$alkyl, $(C_3-C_8)$cycloalkyl, and $(C_3-C_8)$cycloalkyl$(C_1-C_6)$alkyl are independently optionally substituted with 1, 2, 3, or 4 substituents that are independently $(C_1-C_6)$alkoxy, $(C_1-C_6)$alkoxy$(C_1-C_6)$alkyl, $(C_1-C_6)$alkoxycarbonyl, $(C_1-C_6)$alkylthio, halogen, hydroxy, hydroxycarbonyl, $NZ_1Z_2$, or phenyl, wherein the phenyl is optionally substituted with 1, 2, 3, 4, or 5 halogens;
$R_{10}$ and $R_{11}$ are independently H, $(C_1-C_6)$alkyl, $(C_3-C_8)$cycloalkyl, or $(C_3-C_8)$cycloalkyl$(C_1-C_6)$alkyl, wherein the $(C_1-C_6)$alkyl, $(C_3-C_8)$cycloalkyl, and $(C_3-C_8)$cycloalkyl$(C_1-C_6)$alkyl are independently optionally substituted with 1, 2, 3, or 4 substituents that are independently $(C_1-C_6)$alkoxy, $(C_1-C_6)$alkoxy$(C_1-C_6)$alkyl, $(C_1-C_6)$alkoxycarbonyl, $(C_1-C_6)$alkylthio, halogen, hydroxy, hydroxycarbonyl, $NZ_1Z_2$, or phenyl, wherein the phenyl is optionally substituted with 1, 2, 3, 4, or 5 halogens; or $R_4$ and $R_5$ together with the nitrogen atom to which they are attached form azetidine, pyrrolidine, piperidine, piperazine, N-methylpiperazine, morpholine, or azepane;
in which each $Z_1$ and $Z_2$ is independently H or $(C_1-C_6)$alkyl.

11. The compound of claim 10, wherein $R_9$ is $NR_{10}R_{11}$, $R_{10}$ is $(C_2-C_6)$alkyl and $R_{11}$ is H or $(C_1-C_6)$alkyl.

12. A compound of claim 1 that is
(R)-2-Acetamido-3-((2',4'-difluoro-3-(methoxycarbonyl)biphenyl-4-yloxy)carbonylthio)propanoic acid,
(R)-2-Acetamido-3-((2-(methoxycarbonyl)phenoxy)carbonylthio)propanoic acid,
(R)-2-Acetamido-3-((2',4'-difluoro-3-(benzyloxycarbonyl)biphenyl-4-yloxy)carbonylthio)propanoic acid,
(R)-2-Acetamido-3-((2-(benzyloxycarbonyl)phenoxy)carbonylthio)propanoic acid,
(+/−)-2-Acetamido-4-((2',4'-difluoro-3-(methoxycarbonyl)biphenyl-4-yloxy)carbonylthio)butanoic acid,
(+/−)-2-Acetamido-4-((2-(methoxycarbonyl)phenoxy)carbonylthio)butanoic acid,
(R)-2-Acetamido-3-((2',4'-difluoro-3-(ethoxycarbonyl)biphenyl-4-yloxy)carbonylthio)propanoic acid,
(R)-2-Acetamido-3-((2',4'-difluoro-3-(propoxycarbonyl)biphenyl-4-yloxy)carbonylthio) propanoic acid,
(R)-2-Acetamido-3-((2',4'-difluoro-3-(isopropoxycarbonyl)biphenyl-4-yloxy)carbonylthio)propanoic acid,
(R)-2-Acetamido-3-((2-(ethoxycarbonyl)phenoxy)carbonylthio)propanoic acid,
(R)-2-Acetamido-3-((2-(propoxycarbonyl)phenoxy)carbonylthio)propanoic acid,
(R)-2-Acetamido-3-((2-(isopropoxycarbonyl)phenoxy)carbonylthio)propanoic acid,
(R)-2-Acetamido-3-((2-(tert-butoxycarbonyl)phenoxy)carbonylthio)propanoic acid,
(R)-2-Acetamido-3-((3-(tert-butoxycarbonyl)-2',4'-difluorobiphenyl-4-yloxy)carbonylthio)propanoic acid,
(R)-Benzyl 4-((2-acetamido-3-methoxy-3-oxopropylthio)carbonyloxy)-2',4'-difluoro biphenyl-3-carboxylate,
(R)-tert-Butyl 4-((2-acetamido-3-methoxy-3-oxopropylthio)carbonyloxy)-2',4'-difluoro biphenyl-3-carboxylate,
(R)-2-Acetamido-3-((2-(benzyloxycarbonyl)-5-(trifluoromethyl)phenoxy)carbonylthio)propanoic acid,
or a pharmaceutically acceptable salt thereof.

13. A pharmaceutical composition comprising a compound according to claim 1 and at least one pharmaceutically acceptable excipient, adjuvant, or carrier.

14. A method of treating metabolic disorders selected from the group consisting of type I diabetes, type II diabetes, Latent Autoimmune Diabetes of Adulthood (LADA), Wolfram Syndrome 1, Wolcott-Rallison syndrome, hyperglycemia, elevated free fatty acids, elevated triglycerides, insulin resistance, and beta cell protection in a mammal or patient comprising administering to the mammal or patient in need of such treatment a therapeutically effective amount of a compound according to claim 1.

15. A method of treating metabolic disorders selected from the group consisting of type I diabetes, type II diabetes, Latent Autoimmune Diabetes of Adulthood (LADA), Wolfram Syndrome 1, Wolcott-Rallison syndrome, hyperglycemia, elevated free fatty acids, elevated triglycerides, insulin resistance, and beta cell protection in a mammal or patient comprising administering to the mammal or patient in need of such treatment a therapeutically effective amount of a pharmaceutical composition according to claim 13.

16. A pharmaceutical composition comprising a compound according to claim 10 and at least one pharmaceutically acceptable excipient, adjuvant, or carrier.

17. A method of treating metabolic disorders selected from the group consisting of type I diabetes, type II diabetes, Latent Autoimmune Diabetes of Adulthood (LADA), Wolfram Syndrome 1, Wolcott-Rallison syndrome, hyperglycemia, elevated free fatty acids, elevated triglycerides, insulin resistance, and beta cell protection in a mammal or patient comprising administering to the mammal or patient in need of such treatment a therapeutically effective amount of a compound according to claim 10.

18. A method of treating metabolic disorders selected from the group consisting of type I diabetes, type II diabetes, Latent Autoimmune Diabetes of Adulthood (LADA), Wolfram Syndrome 1, Wolcott-Rallison syndrome, hyperglycemia, elevated free fatty acids, elevated triglycerides, insulin resistance, and beta cell protection in a mammal or patient comprising administering to the mammal or patient in need of such treatment a therapeutically effective amount of a pharmaceutical composition according to claim 16.

19. The compound of claim 2, wherein $R_1$ is methoxy, ethoxy, hydroxy, amino, methylamino, or dimethylamino.

20. The compound of claim 2, wherein $R_2$ is 2,4-difluorophenyl.

21. The compound of claim 2, wherein $R_3$ is hydrogen or methyl.

22. The compound of claim 2, wherein $R_4$ is acetyl.

23. The compound of claim 2, wherein $R_5$ is hydrogen.

24. The compound of claim 19, wherein $R_2$ is 2,4-difluorophenyl.

25. The compound of claim 19, wherein $R_3$ is hydrogen or methyl.

26. The compound of claim 19, wherein $R_4$ is acetyl.

27. The compound of claim 19, wherein $R_5$ is hydrogen.

28. The compound of claim 24, wherein $R_3$ is hydrogen or methyl.

29. The compound of claim 24, wherein $R_4$ is acetyl.

30. The compound of claim 24, wherein $R_5$ is hydrogen.

31. The compound of claim 28, wherein $R_4$ is acetyl.

32. The compound of claim 28, wherein $R_5$ is hydrogen.

33. The compound of claim 31, wherein $R_5$ is hydrogen.

34. A method of treating type II diabetes in a mammal or patient comprising administering to the mammal or patient in need of such treatment a therapeutically effective amount of a compound according to claim 1.

35. A method of treating type II diabetes in a mammal or patient comprising administering to the mammal or patient in need of such treatment a therapeutically effective amount of a compound according to claim 10.

36. A method of treating hyperglycemia in a mammal or patient comprising administering to the mammal or patient in need of such treatment a therapeutically effective amount of a compound according to claim 1.

37. A method of treating hyperglycemia in a mammal or patient comprising administering to the mammal or patient in need of such treatment a therapeutically effective amount of a compound according to claim 10.

38. A method of treating elevated triglycerides in a mammal or patient comprising administering to the mammal or patient in need of such treatment a therapeutically effective amount of a compound according to claim 1.

39. A method of treating elevated triglycerides in a mammal or patient comprising administering to the mammal or patient in need of such treatment a therapeutically effective amount of a compound according to claim 10.

40. A method of treating insulin resistance in a mammal or patient comprising administering to the mammal or patient in need of such treatment a therapeutically effective amount of a compound according to claim 1.

41. A method of treating insulin resistance in a mammal or patient comprising administering to the mammal or patient in need of such treatment a therapeutically effective amount of a compound according to claim 10.

\* \* \* \* \*